(12) United States Patent
Grillo-Lopez

(10) Patent No.: US 10,113,000 B2
(45) Date of Patent: *Oct. 30, 2018

(54) COMBINATION THERAPIES FOR B-CELL LYMPHOMAS COMPRISING ADMINISTRATION OF ANTI-CD20 ANTIBODY

(71) Applicant: BIOGEN INC., Cambridge, MA (US)

(72) Inventor: Antonio J. Grillo-Lopez, South San Francisco, CA (US)

(73) Assignee: Biogen Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,594

(22) Filed: Aug. 1, 2016

(65) Prior Publication Data

US 2016/0333106 A1  Nov. 17, 2016

Related U.S. Application Data

(60) Division of application No. 13/524,837, filed on Jun. 15, 2012, which is a division of application No. 11/840,956, filed on Aug. 18, 2007, now Pat. No. 8,329,172, which is a continuation of application No. 10/196,732, filed on Jul. 17, 2002, now abandoned, which is a continuation of application No. 09/372,202, filed on Aug. 11, 1999, now Pat. No. 6,455,043.

(60) Provisional application No. 60/096,180, filed on Aug. 11, 1998.

(51) Int. Cl.

| | |
|---|---|
| *A61K 39/395* | (2006.01) |
| *C07K 16/28* | (2006.01) |
| *A61K 51/10* | (2006.01) |
| *C02F 1/00* | (2006.01) |
| *C07K 16/30* | (2006.01) |
| *A61K 31/475* | (2006.01) |
| *A61K 31/573* | (2006.01) |
| *A61K 31/675* | (2006.01) |
| *A61K 31/704* | (2006.01) |
| *A61K 38/19* | (2006.01) |
| *A61K 38/20* | (2006.01) |
| *A61K 38/21* | (2006.01) |
| *A61K 39/00* | (2006.01) |

(52) U.S. Cl.
CPC ........ *C07K 16/2887* (2013.01); *A61K 31/475* (2013.01); *A61K 31/573* (2013.01); *A61K 31/675* (2013.01); *A61K 31/704* (2013.01); *A61K 38/193* (2013.01); *A61K 38/2013* (2013.01); *A61K 38/212* (2013.01); *A61K 38/217* (2013.01); *A61K 39/39541* (2013.01); *A61K 39/39558* (2013.01); *A61K 51/1027* (2013.01); *A61K 51/1069* (2013.01); *C02F 1/003* (2013.01); *C07K 16/3061* (2013.01); *A61K 2039/505* (2013.01); *A61K 2039/545* (2013.01); *C02F 2307/02* (2013.01); *C07K 2317/24* (2013.01); *C07K 2317/56* (2013.01); *C07K 2317/77* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,831,175 A | 5/1989 | Gansow et al. |
| 4,975,278 A | 12/1990 | Senter et al. |
| 5,099,069 A | 3/1992 | Gansow et al. |
| 5,124,471 A | 6/1992 | Gansow et al. |
| 5,145,677 A | 9/1992 | von Eichborn et al. |
| 5,165,922 A | 11/1992 | Hellstrom et al. |
| 5,225,535 A | 7/1993 | De Freitas et al. |
| 5,225,539 A | 7/1993 | Winter |
| 5,246,692 A | 9/1993 | Gansow et al. |
| 5,250,732 A | 10/1993 | Kogan et al. |
| 5,286,850 A | 2/1994 | Gansow et al. |
| 5,439,665 A | 8/1995 | Hansen et al. |
| 5,460,785 A | 10/1995 | Rhodes et al. |
| 5,500,362 A | 3/1996 | Robinson et al. |
| 5,530,101 A | 6/1996 | Queen et al. |
| 5,595,721 A | 1/1997 | Kaminski et al. |
| 5,633,425 A | 5/1997 | Lonberg et al. |
| 5,648,267 A | 7/1997 | Reff |
| 5,677,171 A | 10/1997 | Hudziak et al. |
| 5,677,180 A | 10/1997 | Robinson et al. |
| 5,686,072 A | 11/1997 | Uhr et al. |
| 5,691,135 A | 11/1997 | Braun et al. |
| 5,691,320 A | 11/1997 | Von Borstel et al. |
| 5,693,780 A | 12/1997 | Newman et al. |
| 5,721,108 A | 2/1998 | Robinson et al. |
| 5,726,023 A | 3/1998 | Cheever et al. |
| 5,736,137 A | 4/1998 | Anderson et al. |
| 5,776,456 A | 7/1998 | Anderson et al. |
| 5,843,398 A | 12/1998 | Kaminski et al. |

(Continued)

FOREIGN PATENT DOCUMENTS

| | | |
|---|---|---|
| AU | 56032/94 A1 | 6/1994 |
| EP | 0 125 023 A1 | 11/1984 |

(Continued)

OTHER PUBLICATIONS

Public Hearing Transcript, Biological Response Modifiers Advisory Committee, Center for Biological Evaluation and Research, Food and Drug Administration, nineteenth meeting Jul. 25, 1997, pp. 1-201 (Miller Reporting Company, Inc.), Aug. 8, 1997.*

(Continued)

*Primary Examiner* — Maher M Haddad
(74) *Attorney, Agent, or Firm* — Ginger R. Dreger

(57) ABSTRACT

New combined therapeutic regimens for treatment of B-cell lymphomas are disclosed which comprise, in particular, administration of anti-CD20 antibodies to patients having low-, intermediate- or high-grade non-Hodgkin's lymphomas.

8 Claims, 4 Drawing Sheets
Specification includes a Sequence Listing.

(56) References Cited

U.S. PATENT DOCUMENTS

| | | | |
|---|---|---|---|
| 5,843,439 A | 12/1998 | Anderson et al. |
| 6,015,542 A | 1/2000 | Kaminski et al. |
| 6,090,365 A | 7/2000 | Kaminski et al. |
| 6,111,166 A | 8/2000 | van de Winkel |
| 6,120,767 A | 9/2000 | Robinson et al. |
| 6,183,744 B1 | 2/2001 | Goldenberg |
| 6,287,537 B1 | 9/2001 | Kaminski et al. |
| 6,306,393 B1 | 10/2001 | Goldenberg |
| 6,399,061 B1 | 6/2002 | Anderson et al. |
| 6,399,649 B1 | 6/2002 | Lerner |
| 6,455,043 B1 | 9/2002 | Grillo-Lopez |
| RE38,088 E | 4/2003 | Larka |
| 6,565,827 B1 | 5/2003 | Kaminski et al. |
| 6,652,852 B1 | 11/2003 | Robinson et al. |
| 6,682,734 B1 | 1/2004 | Anderson et al. |
| 6,893,625 B1 | 5/2005 | Robinson et al. |
| 7,381,560 B2 | 6/2008 | Anderson et al. |
| 7,422,739 B2 | 9/2008 | Anderson et al. |
| 7,682,612 B1 | 3/2010 | White et al. |
| 7,744,877 B2 | 6/2010 | Anderson et al. |
| 8,206,711 B2 | 6/2012 | White et al. |
| 8,329,172 B2 | 12/2012 | Grillo-Lopez |
| 8,557,244 B1 | 10/2013 | White et al. |
| 8,821,873 B2 | 9/2014 | White et al. |
| 9,296,821 B2 | 3/2016 | Grillo-Lopez |
| 9,504,744 B2 | 11/2016 | White et al. |
| 2002/0009444 A1 | 4/2002 | Grillo-Lopez |
| 2002/0197255 A1 | 12/2002 | Anderson et al. |
| 2003/0018014 A1 | 1/2003 | Lerner |
| 2003/0021781 A1 | 1/2003 | Anderson et al. |
| 2003/0026804 A1 | 2/2003 | Grillo-Lopez |
| 2003/0082172 A1 | 5/2003 | Anderson et al. |
| 2003/0095963 A1 | 5/2003 | Anderson et al. |
| 2003/0147885 A1 | 8/2003 | Anderson et al. |
| 2003/0206903 A1 | 11/2003 | Grillo-Lopez |
| 2004/0167319 A1 | 8/2004 | Teeling et al. |
| 2004/0213784 A1 | 10/2004 | Grillo-Lopez et al. |
| 2005/0163708 A1 | 7/2005 | Robinson et al. |
| 2005/0186205 A1 | 8/2005 | Anderson et al. |
| 2006/0034835 A1 | 2/2006 | Adams et al. |
| 2008/0038261 A1 | 2/2008 | Grillo-Lopez et al. |
| 2009/0074760 A1 | 3/2009 | Grillo-Lopez et al. |
| 2010/0080769 A1 | 4/2010 | Grillo-Lopez et al. |
| 2011/0165159 A1 | 7/2011 | Grillo-Lopez et al. |
| 2012/0251534 A1 | 10/2012 | Grillo-Lopez |
| 2012/0251535 A1 | 10/2012 | Grillo-Lopez |
| 2012/0258101 A1 | 10/2012 | Grillo-Lopez |
| 2012/0258102 A1 | 10/2012 | Grillo-Lopez |
| 2013/0273039 A1 | 10/2013 | Grillo-Lopez |
| 2013/0273041 A1 | 10/2013 | Grillo-Lopez et al. |
| 2014/0030263 A1 | 1/2014 | White et al. |
| 2014/0056887 A1 | 2/2014 | Grillo-Lopez |
| 2014/0302018 A1 | 10/2014 | White et al. |
| 2014/0363424 A1 | 12/2014 | Grillo-Lopez et al. |
| 2015/0183882 A1 | 7/2015 | Grillo-Lopez |
| 2016/0333106 A1 | 11/2016 | Grillo-Lopez |
| 2017/0037139 A1 | 2/2017 | White et al. |
| 2017/0037140 A1 | 2/2017 | Grillo-Lopez |

FOREIGN PATENT DOCUMENTS

| | | |
|---|---|---|
| EP | 0 173 494 A2 | 5/1986 |
| EP | 0 274 394 A2 | 7/1988 |
| EP | 0 274 394 A3 | 1/1990 |
| EP | 0 125 023 B1 | 6/1991 |
| EP | 0 510 949 A2 | 10/1992 |
| EP | 0 682 040 A1 | 11/1995 |
| EP | 0 669 836 B1 | 3/1996 |
| EP | 0451216 B1 | 11/1996 |
| EP | 0 752 248 A1 | 1/1997 |
| EP | 0 682 040 B1 | 8/1999 |
| EP | 0 125 023 B2 | 3/2002 |
| EP | 2000149 B1 | 5/2009 |
| EP | 1 974 747 B1 | 6/2012 |
| WO | WO 1987/02671 A1 | 5/1987 |
| WO | WO 1988/04936 A1 | 7/1988 |
| WO | WO 1989/00999 A1 | 2/1989 |
| WO | WO 1991/04320 A1 | 4/1991 |
| WO | WO 1991/17770 A1 | 11/1991 |
| WO | WO 1992/07466 A1 | 5/1992 |
| WO | WO 1993/02108 A1 | 2/1993 |
| WO | WO 1994/08601 A1 | 4/1994 |
| WO | WO 1994/011007 A1 | 5/1994 |
| WO | WO 1994/11026 A2 | 5/1994 |
| WO | WO 1996/018413 A1 | 6/1996 |
| WO | WO 1998/42378 A1 | 10/1998 |
| WO | WO 2000/09160 A1 | 2/2000 |
| WO | WO 2000/27428 A1 | 5/2000 |
| WO | WO 2000/27433 A1 | 5/2000 |
| WO | WO 2001/10460 A1 | 2/2001 |
| WO | WO 2004/ 056312 A2 | 7/2004 |

OTHER PUBLICATIONS

[unknown author] "IDEC Pharmaceuticals Announces Positive Preliminary Results for Pivotal Trial of IDEC-C2B8" *The Free Library* May 21, 1996. pp. 1-3 Retrieved from http://www.thefreelibrary.com/IDEC+PHARMACEUTICALS+ANNOUNCES+POSITIVE+PRELIMINARY+RESULTS+FOR...-a018307934 as retrieved on Aug. 2. 2010.

"Biological Therapy for Cancer Treatment", Stanford Cancer Center, I https://web.archive.org/web/20131617382400/http://cancer.stanford.edu/information/cancerTreatment/methods/biological.html, 2009, pp. 1-8 (Retrieved Dec. 2, 2014).

"Lymphomas: New Recognitions and Therapy Strategies", Wolfgang Hiddemann, Martin Dreyling, Harald Stein editors, Georg Thieme Verlag, Stuttgart, New York, pp. 78-81 (2005), English translation and original in German.

"NCI—Cooperative Group—Industry Relationship Guidelines", updated May 29, 2008 http://ctep.cancer.gov/industrycollaborations2/guidelines.htm, retrieved Aug. 25, 2015, pp. 1-3.

2011 RITUXAN (Rituximab) full prescribing information, pp. 1-8 (Initial US Approval Nov. 1997, Revised Jan. 2011).

Adams R.A.. "Formal discussion: the role of transplantation in the experimental investigation of human leukemia and lymphoma.", Cancer Res, 1967.vol. 27, pp. 2479-2482.

Adams R.A. et al.,"Direct implantation and serial transplantation of human acute lymphoblastic leukemia in hamsters, SB-2", Cancer Res., 1968, vol. 28, No. 6, pp. 1121-1125.

Aisenberg AC, "Coherent view of non-Hodgkin's lymphoma." J Clin Oncol., 1995, vol. 13, pp. 2656-2675.

Alas S. et al., "Potentiation of fludarabine cytotoxicity on non-Hodgkin's lymphoma by pentoxifylline and rituximab", Anticancer Res., 2000, vol. 20, No. 5A, pp. 2961-2966.

Alas S. et al., "Inhibition of interleukin 10 by rituximab results in down-regulation of bcl-2 and sensitization of B-cell non-Hodgkin's lymphoma to apoptosis", Clin. Cancer Res., 2001, vol. 7, No. 3, pp. 709-723.

Alas S. et al., "Rituximab modifies the cisplatinmitochondrial signaling pathway, resulting in apoptosis in cisplatin-resistant non-Hodgkin's lymphoma", Clin. Cancer Res., 2002, vol. 8, No. 3, pp. 836-845.

Al-Ismail, "Combination chemotherapy Including Epirubicin for the Management of Non-Hodgkin's Lymphoma", European J. Cancer and Clinical Oncology, 1987, vol. 23, pp. 1379-1384.

Almasri N.M. et al., "Reduced expression of CD20 antigen as a characteristic marker for chronic lymphocytic leukemia", Am. J Hematol., 1992, vol. 40, pp. 259-263.

Amendment and Reply under 35 CFR §1.111 filed Aug. 25, 2010, in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-16.

Amendment and Response to Restriction Requirement filed Jan. 29, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-9.

Amendment Responsive to Examiner's Request filed Oct. 28, 2011 in U.S. Appl. No. 11/840,956 (Antonio J. Grillo-Lopez, Combina-

(56) References Cited

OTHER PUBLICATIONS tion Therapies for B-Cell Lymphomas Comprising Administration of Anti-CD20 Antibody, filed Aug. 18, 2007), pp. 1-8.
Amit a.G. et al., "Three-dimensional structure of an antigen-antibody complex at 2.8 A resolution," Science, 1986, vol. 233, No. 4765, pp. 747-53 (1986).
Anderson D.R. et al. *Biochem. Soc. Trans.* 25(2): 705-08, 1997. Targeted anti-cancer therapy using rituximab, a chimaeric anti-CD20 antibody (IDEC-C2B8) in the treatment of non-Hodgkin's B-cell lymphoma.
Anderson K.C. et al. *Blood* 63(6): 1424-33, 1984. Expression of human B cell-associated antigens on leukemias and lymphomas: a model of human B cell differentiation.
Anderson K.C. et al. *Blood* 69(2): 597-604, 1987. Hematologic engraftment and immune reconstitution posttransplantation with anti-B 1 purged autologous bone marrow.
Appelbaum F.R. *Hem. Onc. Clin. N Amer.* 5(5): 1013-25, 1991. Radiolabeled monoclonal antibodies in the treatment of non-Hodgkin's lymphoma.
Applicant's Remarks/ Arguments filed Jun. 6, 2011 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 19-35.
Applicant's Remarks/Arguments filed May 22, 2012 with USPTO in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Arber, et. al., "Bone marrow biopsy involvement by non-Hodgkin's lymphoma: frequency of lymphoma types, patterns, blood involvement, and discordance with other sites in 450 specimens", Am. Journ. Surg. Pathol., Dec. 2005, vol. 29, No. 12, pp. 1549-1557.
Archived ECOG website, Jun. 8, 1998, retrieved from parent URL http://web.archive.org/web/19981212013740/http:/ecog.dfci.harvard.edu on Mar. 19, 2015 and Mar. 20, 2015, pp. 1-109.
Arico et al., "Long term survival after heart transplantation for doxorubicin induced cardiomyopathy", *Arch Dis Child 66*, 1991, pp. 985-986.
Armitage J.O. et al. *Cancer* 50: 1695-1702, 1982. Predicting therapeutic outcome in patients with diffuse histiocytic lymphoma treated with cyclophosphamide, adriamycin, vincristine and prednisone (CHOP).
Armitage J.O. et al. *J. Clin. Oncol.* 16(8): 2780-95, 1998. New approach to classifying non-Hodgkin's lymphomas: clinical features of the major histologic subtypes. Non-Hodgkin's Lymphoma Classification Project.
Armitage J.O., "Treatment of Non-Hodgkin's Lymphoma." N Engl. J. Med. 328(14): 1023-30 (Apr. 1993).
Arranz R. et al. *I Clin. Oncol.* 16(4): 1538-46, 1998. Role of interferon alfa-2b in the induction and maintenance treatment of low-grade non-Hodgkin's lymphoma: results from a prospective, multicenter trial with double randomization.
Aviles et al., "Interferon Alpha 2b as Maintenance Therapy in Low Grade Malignant Lymphoma Improves Duration of Remission and Survival", Leukemia and Lymphoma, 1996, vol. 20, pp. 495-499.
Aviles et al., "Maintenance therapy with interferon alfa 2b in patients with diffuse large cell lymphoma", Investigational New Drugs, 1992, vol. 10, pp. 351-355.
Aviles, A., "The role of Interferon as Maintenance Therapy in Malignant Lymphoma", Medical Oncology, 1997, vol. 14, pp. 153-157.
Azogui O. et al. *J. Immunol.* 131: 1205-08, 1983. Inhibition of IL-2 production after human allogeneic bone marrow transplantation.
Badger C.C. et al. *Cancer Res.* 46: 6223-28, 1986. Experimental radioimmunotherapy of murine lymphoma with $^{131}$I-labeled anti-T-cell antibodies.
Belhadj K. et al. *Ann. Oncol.* 15: 504-10, 2004. Efficiency of in vivo purging with rituximab prior to autologous peripheral blood progenitor cell transplantation in B-cell non-Hodgkin's lymphoma: a single institution study.
Bentley, M. and Taylor, K., "Low-grade non-Hodgkin's lymphoma—Biology and therapeutic approaches", *Australian and New Zealand Journal of Medicine* 27, 1997, pp. 150-155.
Berinstein N. et al. *Proc. Amer. Assn. Cancer Res.* 38: 85, abst. No. 567, Mar. 1997. IDEC-C2B8 (rituximab) levels correlate with response in low-grade or follicular non-Hodgkin's lymphoma (LG-F-NHL).
Berinstein N.L. et al. *Ann. Oncol.* 9: 995-1001, 1998. Association of serum rituximab (IDEC-C2B8) concentration and anti-tumor response in the treatment of recurrent low-grade or follicular non-Hodgkin's lymphoma.
Berinstein, "Principles of maintenance therapy," *Leukemia Res.* 30 Suppl. 1: S3-10 (2006).
Berkahn et al., "In vivo purging with rituximab prior to collection of stem cells for autologous transplantation in chronic lymphocytic leukemia," *J. Hematother. Stem Cell Res.* 11(2): 315-20 (2002).
Beychok S. (in) *Cells of Immunoglobulin Synthesis*, B. Pernis et al., eds. New York: Academic Press, 1979, pp. 69-88. Comparative aspects of in vitro and cellular assembly of immunoglobulins.
Bhan A.K. et al. *J. Exp. Med.* 154: 737-49, 1981. Stages of B cell differentiation in human lymphoid tissue.
Bierman et al., "High-dose therapy with autologous hematopoietic rescue for follicular low-grade non-Hodgkin's lymphoma," J. Clin. Oncol. 15(2):445-50 (1997).
Bierman P.J. et al. (in) Hoffman, R., ed., *Hematology*, 2d. ed., Churchill Livingstone, 1995, Chapter 81, pp. 1278-98. Clinical manifestations and staging of and therapy for non-Hodgkin's lymphomas.
*Biogen Idec Inc. v. Corixa Corp.*, Case No. 01-CV-1637 IEG (RBB), Order Granting Patentees' Motion for Reconsideration, etc. (S.D.Cal., Jan. 22, 2004).
*Biogen Idec Inc. v. Corixa Corp.*, Case No. 01-CV-1637 IEG[Doc. Nos. 635, 552, 486] (S.D. Cal. Jan 22, 2004).
*Biogen Idec Inc. v. Corixa Corp.*, Case No. 01-CV-1637 TEG (RBB), Stipulation of Dismissal of Claims and Counterclaims with Prejudice and Order (S.D.Cal., May 13, 2004).
Biogen's Patent Owner Preliminary Response filed Apr. 15, 2015 in Response to Petition Inter Partes Review of U.S. Pat. No. 8,329,172 dated Dec. 15, 2014 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-69.
Biological Therapies: Using the Immune System to Treat Cancer, National Cancer Institute, http://web.archive.org/web/19980216091909/http://cancernet.nci.nih.gov/clinpdq/therapy/Biological_Therapies:_Using_the_Immune_System_To_Treat_Cancer.html (last modified Sep. 1995, archived Feb. 16, 1998) pp. 1-5 (retrieved Apr. 8, 2014).
Blackwelder, William C., "'Proving the Null Hypothesis' in Clinical Trials", Controlled Clinical Trials, 1982, vol. 3, pp. 345-353.
Bodkin et al., "Pharmacokinetic analysis of serum concentrations of the chimeric anti-CD20 antibody IDEC-C2B8 in patients with relapsed B cell lymphoma", Proc Annu Meet Am Assoc Cancer Res 36:365 (#2175), Mar. 1995.
Boon, "Toward a genetic analysis of tumor rejection antigens," *Adv. Cancer Res.* 58: 177-210 (1992).
Bosly A. et al. *Nouv. Rev. Fr. Hematol.* 32(1): 13-16, 1990. Interleukin-2 after autologous bone marrow transplantation as consolidative immunotherapy against minimal residual disease.
Boulianne G.L. et al. *Nature* 312: 643-46, 1984. Production of functional chimaeric mouse/human antibody.
Brown S.L. et al., "Treatment of B-cell lymphomas with anti-idiotype antibodies alone and in combination with alpha interferon"; *Blood* 73:651-661, 1989.
Brunner K.T. et al. *Immunology* 14(2): 181-96, 1968. Quantitative assay of the lytic action of immune lymphoid cells on Cr-labelled allogeneic target cells in vitro; inhibition by isoantibody and by drugs.
Buchsbaum D.J. et al. *IJ Rad. Oncol. Biol. Phys.* 18: 1033-41, 1990. A comparison of $^{131}$I labeled monoclonal antibody 17-1A treatment to external beam irradiation on the growth of LS174T human colon carcinoma xenografts.

(56) References Cited

OTHER PUBLICATIONS

Buchsbaum D.J. et al. *Cancer Res.* 50: 993s-999s, 1990. Comparative binding and preclinical localization and therapy studies with radiolabeled human chimeric and murine 17-1A monoclonal antibodies.

Buchsbaum D.J. et al. *Cancer Res.* 52: 637-642, 1992. Improved delivery of radiolabeled anti-B1 monoclonal antibody to Raji lymphoma xenografts by predosing with unlabeled anti-B1 monoclonal antibody.

Buchsbaum D.J. et al. *Cancer Res.* 52: 6476-81, 1992. Therapy with unlabeled and $^{131}$Ilabeled pan-B-cell monoclonal antibodies in nude mice bearing Raji Burkitt's lymphoma xenografts.

Buchsbaum D.J. et al., "Comparison of 131Iand Y-labeled monoclonal antibody 17-1A for treatment of human colon cancer xenografts", Int. J. Rad. Oncol. Biol. Phys., 1993, vol. 25, No. 4, pp. 629-638.

Buske et al., "Monoclonal Antibody Therapy for B Cell Non-Hodgkin's Lymphomas: Emerging Concepts of a Tumour-targeted Strategy", *European Journal of Cancer*, vol. 35(4), 1999, pp. 549-557.

Byrd et al., "Old and New Therapies in Chronic Lymphocytic Leukemia: Now Is the Time for a Reassessment of Therapeutic Goals", Seminars in Oncology, vol. 25, No. 1 Feb. 1998; pp. 65-74.

Byrd J.C. *Cancer Biother. Radiopharm.* 14(4)L 323, 1999. Rituximab therapy in patients with chronic lymphocytic leukemia.

Byrd J.C. et al. *Blood* 92(10 Suppl. 1): 106a, abst. No. 432 Nov. 1998. Rituximab therapy in hematologic malignancy patients with circulating blood tumor cells: association with increased infusion-related side effects and rapid tumor lysis.

Byrd J.C. et al. *Blood* 92(10 Suppl. 1): 106a, abst. No. 433 Nov. 1998. Rituximab therapy in previously treated Waldenstrom's Macroglobulinemia: Preliminary evidence of activity.

Byrd J.C. et al. *J Clin. Oncol.* 17(3): 791-795, Mar. 1999. Rituximab therapy in hematologic malignancy patients with circulating blood tumor cells: association with increased infusion-related side effects and rapid blood tumor clearance.

Byrd J.C. et al. *J. Clin. Oncol.* 19(8): 2153-64, 2001. Rituximab using a thrice weekly dosing schedule in B-cell chronic lymphocytic leukemia and small lymphocytic lymphoma demonstrates clinical activity and acceptable toxicity.

Cabanillas et. al., "Clinical, Biologic, and Histologic Features of Late Relapses in Diffuse Large Cell Lymphoma", Blood, Feb. 1992, vol. 79, No. 4, pp. 1024-1028.

Cabanillas, F. et al., "Anti-CD20 Antibody (MAB), IDEC-C2B8: Clearance of BCL-2 t(14;18) positive cells from peripheral blood (PB) and bone marrow (BM) in patients (PTS) with relapsed low-grade or follicular lymphoma (LG/F NHL)" BLOOD 88(10):91a (#351), Nov. 1996.

Caligiuri M.A. et al. *J. Clin. Invest.* 91(1): 123-32, 1993. Selective modulation of human natural killer cells in vivo after prolonged infusion of low dose recombinant interleukin 2.

Caligiuri M.A. et al., "Extended continuous infusion low-dose recombinant interleukin-2 in advanced cancer: prolonged immunomodulation without significant toxicity", J. Clin. Oncol., Dec. 1991, vol. 9, No. 12, pp. 2110-2119.

Caligiuri M.A. *Semin. Oncol.*20(6 Suppl 9): 3-10, 1993. Low-dose interleukin-2 therapy: rationale and potential clinical applications.

Calvert J.E. et al. *Semin. Hematol.* 21(4): 226-243, 1984. Cellular events in the differentiation of antibody-secreting cells.

Cancer.Net,"Lymphoma—Non-Hodgkin", www.cancer.net/cancer-types/lymphoma-non-hodgkin/subtypes; Reviewed and approved by the Cancer.Net Editorial Board May 2012; pp. 1-6 (Retrieved Mar. 17, 2013).

CancerNetwork, "Rituximab Effective in Patients with Bulky NHL", Feb. 1, 1999, www.cancernetwork.com/display/article/10165/86193, retrieved Feb. 23, 2011 (3 pages).

Carlson, R. "Rituximab plus CHOP: a new approach for non-Hodgkin's lymphoma?" Inpharma No. 1116:7-8 (Dec. 6, 1997) (Chemotherapy Foundation Symposium XV, New York, US, Nov. 1997).

Carrasquillo J.A. et al., "Improved imaging of metastatic melanoma with high dose 9.2.27 In-111 monoclonal antibody" J. Nucl. Med., 1985, vol. 26, No. 67, Abst. No. 276 (1 page).

Catovsky D. et al. *Eur J. Cancer* 31A(13/14): 2146-54, 1995. Key issues in the treatment of chronic lymphocytic leukaemia (CLL).

Cayeux S. et al. *Blood* 74(6): 2270-77, 1989. T-cell ontogeny after autologous bone marrow transplantation: failure to synthesize interleukin-2 (IL-2) and lack of CD2- and CD3-mediated proliferation by both CD4- and CD8+ cells even in the presence of exogenous IL-2.

Chemocare.com, "Oncovin", www.chemocare.com/chemotherapy/drug-info/Oncovin.aspx; pp. 1-6 (Mar. 2013) (Retrieved Mar. 25, 2013).

Chen J.J. et al., "Tumor idiotype vaccines. VI. Synergistic antitumor effects with combined internal image anti-idiotypes and chemotherapy.", J Immunol., Aug. 1989, vol. 143, No. 3, pp. 1053-1057.

Cheson B.D. et al. *Blood* 87: 4990-97, 1996. National Cancer Institute-specified working group guidelines for chronic lymphocytic leukemia: revised guidelines for diagnosis and treatment.

Cheson, "Radioimmunotherapy of non-Hodgkin lymphomas," *Blood* 101(2): 391-8 (2003), Epub Sep. 19, 2002.

Cheson, B. et al., "Report of an International Workshop to Standardize Response Criteria for Non-Hodgkin's Lymphomas", J Clin Oncol 17(4):1244-53, Apr. 1999.

Chinn P. et al. *Proc. Ann. Mtg. Am. Assn. Cancer Res.* 33: 337, abst. No. 2012, 1992. Production and monoclonal antibody: potential application to treatment of characterization of radiolabeled anti-CD20 B-cell lymphoma.

Chinn P.C. et al. *Int. J. Oncol.* 15(5):1017-25, Nov. 1999. Preclinical evaluation of 90Y-labeled anti-CD20 monoclonal antibody for treatment of non-Hodgkin's lymphoma.

Chinn P.C. et al., "Preclinical evaluation of 90Y-labeled anti-CD20 monoclonal antibody for treatment of non-Hodgkin's lymphoma.", Int J Oncol., Nov. 1999, vol. 15, No. 5, pp. 1017-1025.

Chisesi et. al., "Randomized Study of Chlorambucil (CB) Compared to Interferon (Alfa-2b) Combined with CB in Low-Grade Non-Hodgkin's Lymphoma: An interim report of a randomized study", Eur. J. Cancer, 1991, vol. 27, Supp. 4, pp. S31-S33.

Chomczynki P. et al. *Anal. Biochem.* 162: 156-59, 1987. Single-step method of RNA isolation by acid guanidinium thiocyanate-phenol-chloroform extraction.

Chow K.U. et al. *Haematologica* 87:33-43, 2002. Anti-CD20 antibody (IDEC-C2B8, rituximab) enhances efficacy of cytotoxic drugs on neoplastic lymphocytes in vitro: role of cytokines, complement, and caspases.

Clark E.A. et al. "Anti-Bp35 antibody induces human B cell proliferation: implications for in vivo immunotherapy.", J Cell. Biochem., 1985, Suppl. 9A, p. 63.

Clark E.A. et al. *Proc. Nat'l Acad. Sci. USA* 82(6): 1766-70, 1985. Role of the Bp35 cell surface polypeptide in human B-cell activation.

Classon B.J. et al. *J. Exp. Med.* 169(4): 1497-1502, 1989. The primary structure of the human leukocyte antigen CD37, a species homologue of the rat MRC OC-44 antigen.

Clendeninn, N.J., et. al., "Phase I/II trials of CAMPATH-1H, a humanized anti-lymphocyte monoclonal antibody (MoAb), in non-Hodgkin's lymphoma (NHL) and chronic lymphocytic leukemia (CLL).", Blood, Nov. 1992, vol. 80, No. 10, Supplement 1, Abstract #624, p. 158a.

Clinical Trials (PDQ®); "Phase III randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma"; First Published: Jan. 1, 1998; Last Modified: Aug. 27, 2010; http://www.cancer.gov/clinicaltrials/search/view?cdrid=65935&version=HealthProfessional; pp. 1-7 (Retrieved Jan. 17, 2013).

ClinicalTrials.gov report on the NCT00003204 (ECOG 1496) Clinical Trial (Jan. 27, 2014) http://clinicaltrials.gov/show/NCT00003204 pp. 1-5 (retrieved Dec. 2, 2014).

Cogliatti S.B. et al. *Sw. Med. Weekly* 192: 607-17, 2002. Who is *WHO* and what was *REAL*.

(56) References Cited

OTHER PUBLICATIONS

Cohen et al., "Retreatment with rituximab alone induces sustained remission in a patient with follicular lymphoma with multiple extranodal sites of involvement, relapsing soon after primary treatment with fludarabine-rituximab," Hematol. J. 4(2): 151-3 (2003).
Cohen Y. et al. Leuk. Lymphoma 43(7): 1485-87, 2002. Large B-cell lymphoma manifesting as an invasive cardiac mass: sustained local remission after combination of methotrexate and rituximab.
Coiffier B. Ann. Oncol. 83(Suppl 1): S73-S74, 2004. New treatment strategies in lymphomas: aggressive lymphomas.
Coiffier B. et al. Blood 92(6): 1927-32, 1998. Rituximab (anti-CD20 monoclonal antibody) for the treatment of patients with relapsing or refractory aggressive lymphoma: a multicenter phase II study.
Coiffier B. et al. N Engl. J. Med. 346(4): 235-42, 2002. CHOP chemotherapy plus rituximab compared with CHOP alone in elderly patients with diffuse large-B-cell lymphoma.
Coiffier, "Rituximab in combination with CHOP improves survival in elderly patients with aggressive non-Hodgkin's lymphoma," Semin. Oncol. 29(2 Suppl. 6): 18-22 (2002).
Coiffier, B., "What treatment for elderly patients with aggressive lymphoma?", Annals of Oncology, 1994, vol. 5, pp. 873-875.
Coleman M. et al. Blood 102(11 pt.1): 29a, abst. No. 29, 2003. The BEXXAR® therapeutic regimen (tositumomab and Iodine 1-131 tositumomab) produced durable complete remissions in heavily pretreated patients with non-Hodgkin's lymphoma (NHL), rituximabrelapsed/ refractory disease, and rituximab-naive disease.
Colombat P. et al. Blood 97: 101-06, 2001. Rituximab (anti-CD20 monoclonal antibody) as single first-line therapy for patients with follicular lymphoma with a low tumor burden: clinical and molecular evaluation.
Comella, et al., "Combination chemotherapy (CVP or CHOP)-radiotherapy approach in early stage non-Hodgkin's lymphomas", Tumori, Apr. 1982, vol. 68, No. 2, pp. 137-142.
Cope. Oncology 8(4): 100, 1994. Antibody shows promise in treating B-cell lymphoma.
Curti B.D. Crit. Rev. Oncol. Hematol. 14(1): 29-39, 1993. Physical barriers to drug delivery in tumors.
Czuczman et al., "Chemoimmunotherapy of Low-Grade Lymphoma with the Anti-CD20 Antibody IDEC-C2B8 in Combination with Chop Chemotherapy", Cancer Investigation (abstract 53) 14(Suppl. 1):59-61 (1996).
Czuczman et al., "IDEC-C2B8/CHOP chemoimmunotherapy in patients with low-grade lymphoma: Interim clinical and bcl-2 (PCR) results", Annals of Oncology, vol. 7, Suppl. 1, pp. 56-57, (1996).
Czuczman et al., "IDEC-C2B8/CHOP chemoimmunotherapy in patients with low grade lymphoma: Clinical and bcl-2 (PCR) results," J Mol. Med.. 1997, vol. 75, No. 7, abstract #258, p. B231.
Czuczman M. et al. Blood 94(10 Supp. 1): 99a, abst. No. 432, 1999. Rituximab/CHOP chemoimmunotherapy in patients (PTS) with low grade lymphoma (LG/F NHL): progression free survival (PFS) after three years (median) follow-up.
Czuczman M.S. et al. J. Clin. Oncol. 17(1): 268-76, Jan. 1999. Treatment of patients with low-grade B-cell lymphoma with the combination of chimeric anti-CD20 monoclonal antibody and CHOP chemotherapy.
Czuczman M.S. et al., "IDEC-C2B8 (Rituximab) alone and in combination with CHOP in the treatment of low-grade B-cell lymphoma", Cancer Invest 16 (1 Suppl):21-22 (#17), 1998.
Czuczman M.S. et al., "IDEC-C2B8 and CHOP chemoimmunotherapy of low-grade lymphoma", Blood 86(10 suppl 1):55a (#206), Nov. 1995.
Czuczman M.S. et al., "IDEC-C2B8/CHOP Chemoimmunotherapy in Patients with Low-Grade Lymphoma: Clinical Bcl-2 (PCR) Final Results", Nov. 1996, Blood 88, vol. 10, abstract 1799, pp. 453a, Nov. 1996.
Czuczman, M.S. et al., "Rituxan™/CHOP Chemo immunotherapy in patients with low-grade or follicular (LG/F) non-Hodgkin's lymphoma (NHL)", J Immunother 20(5):401, Sep. 1997.
Czuczman, M.S. et al., "IDEC-C2B8 clears bcl-2 (t14;18) in patients (pts) with relapsed low grade or follicular lymphoma (LG/F NHL)", Proc Annu Meet Am Assoc Cancer Res 38:84 (#565), Mar. 1997.
Czuczman, M.S. et al., "Phase II Clinical Trial of IDEC-C2B8/ CHOP Combination Therapy in Low Grade Lymphoma: Preliminary Results", Proc Am Soc Clin Oncol 14:401 (#1261), Mar. 1995.
Czuczman, M.S. et al., "The Anti-CD20 Antibody (MAB) IDEC-C2B8 Clears Lymphoma Cells Bearing the t(14;18) Translocation (bcl-2) from the Peripheral Blood (PB) and Bone Marrow (BM) of a Proportion of Patients (PTS) with Low-Grade or Follicular (LG/F) Non-Hodgkin's Lymphoma (NHL)", J. Ann Oncol 7(5 Suppl):111 (#532P), Nov. 1996.
Dallaire, B.K. et al., "IDEC-C2B8 (RITUXIMAB): Biology and preclinical studies", J Mol Med, Jul. 1997, vol. 75, No. 7, abstract #256, pp. B230-B231.
Dana et al., "Long-Term Follow-Up of Patients With Low-Grade Malignant Lymphomas Treated With Doxorubicin-Based Chemotherapy or Chemoimmunotherapy" J. Clinical Oncology, vol. 11, No. 4 Apr. 1993, pp. 644-651.
Dana et. al., "A Randomized Study of Alpha-Interferon Consolidation in Patients with Low-Grade Lymphoma Who Have Responded to Pro-Mace-Mopp (Day 1-8) (SWOG 8809)", Proceedings of ASCO, May 16-19, 1998, vol. 17, Abstract 10, p. 3a.
Davis et al., "Retreatments with Rituxan (rituximab, IDEC-C2B8) have significant efficacy, do not cause HAMA, and are a viable minimally toxic alternative in relapsed or refractory non-Hodgkin's lymphoma (abstract)," Blood 90(10 Suppl. 1 Part 1): 509a (1997).
Davis et al., "Rituximab Anti-CD20 Monoclonal Antibody Therapy in Non-Hodgkin's Lymphoma: Safety and Efficacy of Re-Treatment," J. Clin. Oncol. 18: 3135-3143 (2000).
Davis et al., "Anti-Idiotype Antibodies Can Induce Long-Term Complete Remissions in Non-Hodgkin's Lymphoma Without Eradicating the Malignant Clone", Blood, vol. 92, No. 4 Aug. 15, 1998: pp. 1184-1190.
Davis T. et al. Blood 90(10 Suppl. 1): 509a, abst No. 2269, Nov. 1997. Retreatments with RITUXAN™ (Rituximab, Idec-C2B8) have significant efficacy, do not cause HAMA, and are a viable minimally toxic alternative in relapsed or refractory non-Hodgkin's lymphoma (NHL).
Davis T. et al.. Proc. Amer. Soc. Clin. Oncol. 17: abst. No. 39, May 1998. Combination immunotherapy of low grade or follicular (LG/F) non-Hodgkin's lymphoma (NHL) with rituximab and alpha interferon: interim analysis.
Davis T.A. et al. Blood 86(10 Suppl. 1): 273a, abst. No. 1080, 1995. Yttrium labeled antiCD20 therapy for recurrent B cell lymphoma.
Davis T.A. et al. Blood 92(10 Suppl. 1): 414a, abst. No. 1710, Nov. 1998. Rituximab: phase II (PII) retreatment (ReRx) study in patients (PTS) with low grade or follicular (LG/F) NHL.
Davis T.A. et al. Blood 92(10 Suppl. 1): 414a, abst. No. 1711, Nov. 1998. Rituximab: first report of a phase II (PII) trial in NHL patients (PTS) with bulky disease.
Davis T.A. et al. Clin. Cancer Res. 5(3): 611-15, 1999. Therapy of B-cell lymphoma with anti-CD20 antibodies can result in the loss of CD20 antigen expression.
Davis T.A. et al. I Clin. Oncol. 17(6): 1851-57, 1999. Single-agent monoclonal antibody efficacy in bulky non-Hodgkin's lymphoma: results of a phase IiItrial of rituximab.
Davis T.A. et al. Proc. Amer. Assn. Cancer Res. 39: 435, abst. No. 2964, 1998. Therapy of B cell lymphoma with anti-CD20 can result in relapse with loss of CD20 expression.
Decision Denying Institution of Inter Partes Review of U.S. Pat. No. 8,329,172 dated Jul. 13, 2015 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-35.
Declaration of Michael J. Grossbard, M.D., in Support of the Petition for Inter Partes Review of U.S. Pat. No. 8,329,172 (U.S. Appl. No. 11/840,956, Antonio J. Grillo-Lopez, Combination Therapies for B-Cell Lymphomas Comprising Administration of Anti-CD20 Antibody, filed Aug. 18, 2007), dated Dec. 5, 2014 pp. 1-107.

(56) References Cited

OTHER PUBLICATIONS

Demidem A. et al. *Cancer Biother. Radiopharm.* 12(3): 177-86, 1997. Chimeric anti-CD20 (IDEC-C2B8) monoclonal antibody sensitizes a B cell lymphoma cell line to cell killing by cytotoxic drugs.

Demidem et al., Chimeric anti-CD20 antibody (IDEC-C2B8) is apoptotic and sensitizes drug resistant human B cell lymphomas and AIDS related lymphomas to the cytotoxic effect of CDDP, VP-16 and toxins *FASEB* J9(3):A206, Abstract #1197, 1995.

DeNardo G.L. et al. *Cancer Res.* 50(3 Suppl.): 1014s-1016s, 1990. Fractionated radioimmunotherapy of B-cell malignancies with $^{131}$I-Lym-1.

DeNardo G.L. et al. *I.J. Rad. Oncol. Biol.Phys.* 11(2): 335-48, 1985. Requirements for a treatment plan in system for radioimmunotherapy.

DeNardo S.J. et al. *Antibody Immunoconj. Radiopharm.* 1(1): 17-33, 1988. Pilot studies of radioimmunotherapy of B cell lymphoma and leukemia using 1-131 Lym-1 monoclonal antibody.

DeNardo S.J. et al. *Cancer* 3(3 Suppl.): 1023-32, 1994. The biologic window for chimeric L6 radioimmunotherapy.

Di Gaetano N. et al., "Synergism between fludarabine and rituximab revealed in a follicular lymphoma cell line resistant to the cytotoxic activity of either drug alone", Br. J Haematol, 2001, vol. 114, No. 4, pp. 800-809.

Dickson S. *Gen. Engr. News* 5(3): 1, Mar. 1985. Scientists produce chimeric monoclonal Abs.

Dillman R.O, "Antibodies as cytotoxic therapy.", J. Clin. Oncol., Jul. 1994, vol. 12, No. 7, pp. 1497-1515.

Dillman RO et al., "Therapy of chronic lymphocytic leukemia and cutaneous T-cell lymphoma with T101 monoclonal antibody." J Clin Oncol 1984, vol. 2, pp. 881-891.

Dixon, et. al., "Effect of Age on Therapeutic Outcome in Advanced Diffuse Histiocytic Lymphoma: The Southwest Oncology Group Experience", Mar. 1986, vol. 4, No. 3, pp. 295-305.

Documents from European Oppositions pertaining to EP Application No. 08005921.5 (Antonio J. Grillo-Lopez, Combination Therapies for B-Cell Lymphomas Comprising Administration of Anti-CD20 Antibody, filed Aug. 11, 1999) (Patent No. EP 1974747), pp. 1-52.

Eary J.F. et al. *J Nucl. Med.* 31(8): 1257-68, 1990. Imaging and treatment of B-cell lymphoma.

ECOG E1496 Trial Results "Non-Progressing Low-grade NHL after CVP-RITUXAN® (Rituximab)", Internet Archive, Wayback Machine, Originally Posted Sep. 25, 2008, pp. 1-5, (Retrieved Oct. 14, 2014) https://web.archive.org/web/20080925225303/http://www.rituxan.com/lymphoma/hcp/indications/E1496/index.m.

ECOG E1496 Trial Results "Non-Progressing Low-grade NHL after CVP-RITUXAN® (Rituximab)", Study date Mar. 9, 2009, pp. 1-7, (Retrieved Dec. 2, 2010) http://www.rituxan.com/lymphoma/hcp/indications/E1496/index.m.

ECOG E1496, Activation of Protocol E1496, Randomized Phase III Study in Low Grade Lymphoma Comparing Cyclphosphamide/Fludarabine to Standard Therapy Followed by Maintenance Anti-CD20 Antibody, Activation Date: Mar. 19, 1998 pp. 1-47.

ECOG E4494, Activation of Protocol E4494, A Phase III Trial of CHOP versus CHOP and Chimeric Anti-CD20 Monoclonal Antibody (IDEC-C2B8) in Older Patients with Diffuse Mixed, Diffuse Large Cell and Immunoblastic Large Cell Histology Non-Hodgkin's Lymphoma, Activation Date: Dec. 12, 1997 pp. 1-61.

ECOG Institutions by Name, http://web.archive.org/web/19980519084032/http://ecog.dfci.haryard.edu/~ecogdba/general/insts_byname.html (archived May 19, 1998) pp. 1-10 (retrieved Dec. 4, 2014).

ECOG's Active Protocols: ECOG Protocols Active as of May 19, 1998, Internet Archive, Wayback Machine, http://web.archive.org/web/19980519084342/http://ecog.dfci.haryard.edu/~ecogdba/active_reports/Lymphoma.html; Revised: May 19, 1998; 1 page (Retrieved Mar. 4, 2013).

Einfeld D.A. et al. *EMBO J.* 7: 711-17, 1988. Molecular cloning of the human B cell CD20 receptor predicts a hydrophobic protein with multiple transmembrane domains.

Eisenbeis C.F. et al. *Clin. Cancer Res.* 10: 6101-10, 2004. Combination immunotherapy of B-cell non-Hodgkin's lymphoma with rituximab and interleukin-2: a preclinical and phase I study.

Endo K. *Jpn. J. Cancer Chemother.* 26: 744-48, 1999. Current status of nuclear medicine in Japan.

Engel, A. et al. *Ann. Hematol.* 77(suppl. 2): S180, abst. No. 717, 1998. Multicenter phase II study of the monoclonal anti-CD20 antibody rituximab (IDEC-C2B8) in patients with intermediate/high grade non-Hodgkin's lymphoma.

FDA Clinical Review of Rituximab dated Sep. 29, 2006, pp. 1-110.

FDA label of Doxorubicin Hydrochloride for injection USP, pp. 1-22, 2010.

Feugier et al., "Long-Term Results of the R-CHOP Study in the Treatment of Elderly Patients With Diffuse Large B-Cell Lymphoma: A Study by the Groupe d'Etude des Lymphomes de l'Adult"; *Journal of Clinical Oncology*, vol. 23, No. 18, Jun. 20, 2005, pp. 4117-4126.

Fisher D.C. et al. *Blood* 92: 247a, abst. No. 1010, 1998. Phase 1 trial with CD40-activated follicular lymphoma cells: a novel cellular vaccine strategy for B cell malignancies.

Fisher, et. al., "Comparison of a Standard Regimen (CHOP) with Three Intensive Chemotherapy Regimens for Advanced Non-Hodgkin's Lymphoma", New England Journal of Medicine, Apr. 1993, vol. 328, No. 14, pp. 1002-1006.

Flinn I.W. et al. *Blood* 92(10 Suppl. 1): 648a, abst. No. 2678, Nov. 1998. In vivo purging and adjuvant immunotherapy with rituximab during PBSC transplant for NHM [sic].

Flinn, I.W., et al., "Immunotherapy with rituximab during peripheral blood stem cell transplantation for non-Hodgkin's lymphoma." Biol Blood Marrow Transplant. 2000;6(6):628-32.

Foon et. al., "Lymphomas", Williams Hematology, 5th edition, Ch. 111, Part ix, Beutler, Lichtman, Coller, & Kipps, McGraw-Hill, Inc., 1995, pp. 1076-1096.

Foon KA et al., "Effects of monoclonal antibody therapy in patients with chronic lymphocytic leukemia." Blood, 1984, vol. 64, pp. 1085-1093.

Foon KA, "Laboratory and Clinical Applications of Monoclonal Antibodies for Leukemias and Non-Hodgkin's Lymphomas." Curr. Probl. Cancer 13(2): 57-128 (Mar./Apr. 1989).

Foran J.M. et al. *Br. I Haematol.* 102(1): 149, 1998. Immunotherapy of mantle cell lymphoma (MCL), lymphoplasmacytoid lymphoma (LPC) and Waldentrom's macroglobulinemia (WW), and small lymphocytic leukemia (SLL) with rituximab (IDECC2B8): preliminary results of an ongoing international multicentre trial.

Foran J.M. et al., "European phase Ii study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma", J Clin Oncol., Jan. 2000, vol. 18, No. 2, pp. 317-324.

Foran, et al., "Immunotherapy of recurrent follicular lymphoma (FL) with Rituximab (IDECCB8): Preliminary results of an ongoing UK multicentre trial", British Journal of Haematology, vol. 102, No. 1, p. 243, (1998).

Ford B. *The CALGB: Quarterly Newsletter of the Cancer and Leukemia Group B* 7(1): 4-5, Spring 1998. Rituxan (Rituximab).

Ford S.M. et al. *Highlights in Oncology Practice* 16(2): 40-50, 1998. Immunotherapeutic approaches to treatment of B-cell neoplasms: focus on unconjugated antibodies.

Freedman A.S. et al., "Autologous bone marrow transplantation in B-cell non-Hodgkin's lymphoma: very low treatment-related mortality in 100 patients in sensitive relapse", J. Clin Oncol., May 1990, vol. 8, No. 5, pp. 784-791.

Fridik M.A. et al. *Ann. Hematol.* 74(1): 7-10, 1997. First-line treatment of Waldenstrom's disease with cladribine.

Friedberg J.W. et al. *Expert Rev. Anticancer Ther.* 4(1): 18-26, 2004. Iodine-131 tositumomab (Bexxar): radioimmunoconjugate therapy for indolent and transformed B-cell non-Hodgkin's lymphoma.

Full prescribing information for Rituxan (rituximab). Revised Feb. 2010, pp. 1-35.

(56) References Cited

OTHER PUBLICATIONS

Gallagher CJ et al., "Follicular lymphoma: Prognostic factors for response and survival.", 1986, J Clin Oncol, vol. 4, pp. 1470-1480.
Garcia-Conde J et al: "Study to Evaluate the Efficacy and Safety of Rituximab (IDEC-C2B8) and CVP Chemotherapy in Low-Grade or Follicular B-Cell Lymphoma After Relapse. Preliminary Results at a Follow Up Period of 3 Months," BLOOD, vol. 94, No. 10 Suppl. 1 Part 2, p. 261 b Nov. 15, 1999.
Ghielmini et al., "Prolonged treatment with rituximab in patients with follicular lymphoma significantly increases event-free survival and response duration compared with the standard weekly X4 schedule", Blood, 2004, vol. 103, No. 12, pp. 4416-4423.
Gianni A.M. et al. *Blood* 102: 749-55, 2003. Long-term remission in mantle cell lymphoma following high-dose sequential chemotherapy and in vivo rituximab-purged stem cell autografting (R-HDS regimen).
Ginaldi L. et al. *J. Clin. Pathol.* 51: 364-69, 1998. Levels of expression of CD19 and CD20 in chronic B leukaemias.
Gisselbrecht. al., "Treatment of low-grade non-Hodgkin's lymphomas", Non-Hodgkin's Lymphoma, Solal-Celigny, Brousse, Reyes, Gisselbrecht & Coiffier, Manson Publishing Ltd., 1993, pp. 317-336.
Gisselbrecht, et. al., "Rituximab maintenance therapy after autologous stem-cell transplantation in patients with relapsed CD20(+) diffuse large B-cell lymphoma: final analysis of the collaborative trial in relapsed aggressive lymphoma", J. Clin. Oncol, Dec. 2012, vol. 30, No. 36, pp. 4462-4469.
Gladstone, D.E. et al, "High-dose cyclophosphamide and rituximab without stem cell transplant: a feasibility study for low grade B-cell, transformed and mantle cell lymphomas." Leuk Lymphoma. Nov. 2011;52(11):2076-81.
Golay J. et al. *Haematologica* 88: 1002-12, 2003. Rituximab-mediated antibody-dependent cellular cytotoxicity against neoplastic B cells is stimulated strongly by interleukin-2.
Golay J.T. et al. *J. Immunol.* 135(6): 3795-801, 1985. The CD20 (Bp35) antigen is involved in activation of B cells from the G0 to the 01 phase of the cell cycle.
Goldenberg D.M. et al. *J. Clin. Oncol.* 9(4): 548-64, 1991. Imaging and therapy of gastrointestinal cancers with radiolabeled antibodies.
Goldenberg DM, et al. "Characterization of New, Chimeric and Humanized, Anti-CD20 Monoclonal Antibodies, cA20 and hA20, with Equivalent Efficacy to Rituximab in-vitro and in Xenografted Human Non-Hodgkin's lymphoma." (Abstract #2260) Poster Session: Biologic Therapy of Lymphomas: Laboratory Investigations held on Dec. 8, 2002, 1 page. (Retrieved Sep. 30, 2004) http://www.abstracts2view.com/hemphiladelphia02/view.php?nu=HEM2L_1183.
Gonzalez-Barca et al., "Low-dose subcutaneous interleukin-2 in patients with minimal residual lymphoid neoplasm disease," *Eur. J. Hemat6.* 62(4): 231-238 (1999).
Gopal et al., "Clinical applications of anti-CD20 antibodies", J. Lab Clin Med; 134:, 1999, pp. 445-450.
Gordon L.I. et al. *Blood* 94(10 Suppl. 1): 91a, abst. No. 396, 1999. ZEVALIN™ (IDECY2B8) radioimmunotherapy of rituximab refractory follicular non-Hodgkin's lymphoma (NHL): interim results.
Gordon L.I. et al. *J Immunother* 22(5): 459, 1999. Update on IDEC-Y2B8 (ZEVALINTM) radioimmunotherapy of B-cell NHL.
Gottlieb et al. "Chemotherapy of malignant lymphoma with adriamycin", Cancer Research 33:3024-3028 (Nov. 1973).
Greenberger J.S. et al. *Cancer Res.* 45(2): 758-67, 1985. Effects of monoclonal antibody and complement treatment of human marrow on hematopoiesis in continuous bone marrow culture.
Greiner J.W. et al. *Science* 235(4791): 895-98, 1987. Recombinant interferon enhances monoclonal antibody-targeting of carcinoma lesions in vivo.
Gribben J.G. et al. *N Engl. I Med.* 325(22): 1525-32, 1991. Immunologic purging of marrow assessed by PCR before autologous bone marrow transplantation for B-cell lymphoma.

Gribben J.G. et al., "Detection of residual lymphoma cells by polymerase chain reaction in peripheral blood is significantly less predictive for relapse than detection in bone marrow." Blood, 1994, vol. 83, pp. 3800-3807.
Grillo-Lopez A.J. et al. *Ann. Oncol.* 7(3 Suppl.): 57, abst. No. 195, 1996. Treatment (rx) of relapsed non-Hodgkin's lymphoma (NHL) using the 90-yttrium (90-Y) labeled anti-CD20 monoclonal antibody (MAB) IDEC-Y2B8: a phase I clinical trial (PI CT).
Grillo-Lopez A.J. et al. *Antibody Immunoconj. Radiopharm.* 8: 60, abst. No. 10, 1995. Treatment options for patients with relapsed low-grade or follicular lymphoma: the role of IDEC-C2B8.
Grillo-Lopez A.J. et al. *Blood* 86(10 Suppl. 1): 55a, abst. No. 207, 1995. Phase I study of IDEC-Y2B8: 90-yttrium labeled anti-CD20 monoclonal antibody therapy of relapsed non-Hodgkin's lymphoma.
Grillo-Lopez A.J. et al. *Br. J. Haematol.* 93(Suppl. 2): 283, abst. No. 1072, 1996. IDECC2B8 chimeric anti-CD20 antibody (MAB): safety and clinical activity in the treatment of patients (PTS) with relapsed low-grade or follicular (IWF:A-D) non-Hodgkin's lymphoma (NHL).
Grillo-Lopez A.J. IBC Int'l. Conference on Antibody Engineering, La Jolla, Dec. 1994. IDEC-C2B8 chimeric antibody and IDEC-Y2B8 radiolabeled antibody phase I and II studies in patients with non-Hodgkin's lymphoma (abstract of presentation).
Grillo-López, A.J. et al., Anti-CD20 Chimeric Antibody, IDEC-C2B8: Safety and Clinical Activity in the Treatment of Relapsed Low Grade or Follicular (IWF: A-D) Lymphomas (LG-F/NHL), 25th Annual Meeting of the International Society for Experimental Hematology, Exp Hematol Abstract 691, vol. 24, No. 9, Aug. 1996, pp. 1150.
Grillo-López, A.J. et al., "Development of Response Criteria (RC) for Low-Grade or Follicular Lymphomas (LG/F NHL) and Application in a 166 Patient Study", 26th Annual Meeting of the International Society for Experimental Hematology, Exp Hematol, Aug. 1997, vol. 25, No. 8, Abstract 17, p. 732.
Grillo-López, .J. et al., "IDEC-C2B8 (RITUXIMAB): Clinical Activity in Poor Prognosis Subgroups of Relapsed Low-Grade or Follicular Lymphoma", 26th Annual Meeting of the International Society for Experimental Hematology, Exp Hematol Abstract 406, vol. 25, No. 8, Aug. 1997, pp. 846.
Grillo-López, A.J. et al., "IDEC-C2B8: Clinical development of a chimeric anti-CD20 antibody for the treatment of patients (pts) with relapsed low-grade or follicular NHL", Abstract 190, Ann Oncol 7(1 Suppl):56, Mar. 1996.
Grillo-López, A.J. et al., "Monoclonal Anti-CD20 Antibody (IDEC-C2B8) Therapy of B-Cell Non-Hodgkin's Lymphoma—Pre Clinical Development and Early Clinical Results", Proc Eighth NCI/EORTC Symposium on New Drugs in Cancer Therapy, p. 112 (#175) Mar. 1994.
Grillo-López, A.J. et al., "Overview of the Clinical Development of Rituximab: First Monoclonal Antibody Approved for the Treatment of Lymphoma", Seminars in Oncology, vol. 26, No. 5, Suppl 14 (Oct. 1999); pp. 66-73.
Grillo-López, A.J. et al., "Overview of the safety and efficacy of IDEC-C2B8 including activity in patient populations with poor prognosis low grade or follicular NHL (LG/F NHL)", J. Mol. Med. Abstract 259, vol. 75, No. 7, Jul. 1997, pp. B231-B232.
Grillo-López, A.J. et al., "Preclinical and Early Clinical Development of the Anti-CD20 Monoclonal Antibody IDEC-C2B8", Ninth International Conference on Monoclonal Antibody Immunoconjugates for Cancer, Antibody Immunoconjugates, and Radiopharmaceuticals, vol. 7, No. 1, Abstract 64, Spring 1994.
Grillo-López, A.J. et al., "Response criteria (RC) for NHL: Importance of "normal" lymph node (LN) size and correlations with response." Blood 92(10 Suppl 1):412a (#1701), Nov. 1998.
Grillo-López, A.J. et al., "Rituxan™: Anti CD20 monoclonal antibody for the treatment of lymphoma." Exp Hematol 26(8):746 (#233), Aug. 1998.
Grillo-López, A.J., "IDEC-C2B8: Initial Phase II Results in Patients with B-Cell Lymphoma", Journal of Immunotherapy with Emphasis on Tumor Immunology, vol. 16, No. 3, Oct. 1994, pp. 236.

(56) References Cited

OTHER PUBLICATIONS

Grillo-López, A.J., "Rituximab (IDEC-C2B8): Development of an anti-CD20 monoclonal antibody (MAB) for the treatment of non-Hodgkin's lymphoma." Ann Hematol 77(Suppl 1):A7 (#26), 1998.
Grillo-López, A.J., "Rituximab: An Insider's Historical Perspective", Seminars in Oncology, vol. 27, No. 6, Suppl 12 (Dec. 2000); pp. 9-16.
Grillo-López, A.J., et al., "Clinical activity of the monoclonal antibody (MAB) IDEC-C2B8 in patients (pts) with relapsed low-grade or follicular NHL (R-LG/F NHL)", Eur J Cancer 33(58):S260-S261 (#1179), Sep. 1997.
Grillo-López, AJ "The First Antibody Therapy for Cancer: a Personal Experience", Expert Review of Anticancer Therapy Retrospective, 2013, vol. 13, No. 4, pp. 399-406.
Grossbard M.L. and Multani, P.S. "The McLaughlin et al Article Reviewed", Dec. 1998, Oncology, 12(12):1769-1770.
Grossbard M.L. and Multani, P.S., "Clinical Status and Optimal Use of Rituximab for B-Cell Lymphomas", Oncology vol. 12(12); 1998, pp. 1-2, as published online by www.cancernetwork.com on Dec. 1, 1998 (Retrieved Feb. 4, 2013) http://www.cancernetwork.com/print/article/10165/66803?printable=true.
Grossbard M.L. et al. Blood 80(4): 863-78, 1992. Monoclonal antibody-based therapies of leukemia and lymphoma.
Guan, et al., "Rituximab in combination with CHOP, an effective and well-tolerated salvage regimen for diffuse large B-Cell Lymphoma", Chinese Journal of Clinical Oncology, vol. 4, No. 4, pp. 264-267, (2007).
Gupta and Lister, "Current Management of Follicular Lymphoma", Current Opinion in Oncology, 1996, vol. 8, pp. 360-365.
Gura T. Science 278: 1041-42, 1997. Systems for identifying new drugs are often faulty.
Habermann, et al., "Rituximab-CHOP versus CHOP alone or with maintenance rituximab in older patients with diffuse large B-cell lymphoma", [PUBMED Abstract] J Clin Oncol 24 (19): 3121-7, 2006.
Habermann, et al., "Rituximab-CHOP versus CHOP with or without maintenance rituximab in patients 60 years of age or older with diffuse large B-cell lymphoma (DLBCL): an update" Blood (ASH Annual Meeting Abstracts) 104 (11): A-127, 2004. (Retrieved Oct. 14, 2011) (2 pages).
Hagenbeek A. et al. J. Clin. Oncol. 16(1): 41-47, 1998. Maintenance of remission with human recombinant interferon alfa-2a in patients with stages III and IV low-grade malignant non-Hodgkin's lymphoma. European Organization for Research and Treatment of Cancer Lymphoma Cooperative Group.
Hainsworth et al. "Rituximab as First-Line and Maintenance Therapy for Patients With Indolent Non-Hodgkin's Lymphoma", J. Clinical Oncology, 2002, vol. 20, pp. 4261-4267.
Hainsworth et al., "Rituximab Induction and Maintenance Therapy in Patients (pts) with Previously Untreated Low-Grade Non-Hodgkin's Lymphoma (NHL): Preliminary Results of a Minnie Pearl Cancer Research Network Phase II Trial" Proceedings of the ASCO, vol. 18 (Abstract #105) 1999, p. 29a ; with e-mail from Ascopubs [ascopubs@asco.org] dated Mar. 11, 2013, 1 pg, stating that the 1999 Program Proceedings vol. 18 was made available to the public on May 15, 1999.
Hainsworth J.D. et al. Blood 95: 3052-56, 2000. Rituximab monoclonal antibody as initial systemic therapy for patients with low-grade non-Hodgkin lymphoma.
Haioun, et. al., "Survival Benefit of High-Dose Therapy in Poor-Risk Aggressive Non-Hodgkin's LymphomaL Final Analysis of the Prospective LNH87-2 Protocol—A Groupe d'Etude des Lymphomes de l'Adute Study", Aug. 2000, vol. 18, No. 16, pp. 3025-3030.
Hancock et al., "A monoclonal antibody against the c-erbB-2 protein enhances the cytotoxicity of cis-diamrninedichloroplatinum against human breast and ovarian tumor cell lines," Cancer Res. 51(17): 4575-80 (1991).
Harris N.L. et al. Blood 54(5): 1361-92, 1994. A revised European-American classification of lymphoid neoplasms: a proposal from the International Lymphoma Study Group.
Harris N.L. et al. J. Clin. Oncol. 17(12): 3835-49, 1999. World Health Organization classification of neoplastic diseases of the hematopoietic and lymphoid tissues: report of the Clinical Advisory Committee meeting—Airlie House, Virginia, Nov. 1997.
Hartwell L.H. et al. Science 278: 1064-68, 1997. Integrating genetic approaches into the discovery of anticancer drugs.
Herold M. et al. Ann. Hematol. 79: 332-335, 2000. Successful treatment and re-treatment of resistant B-cell chronic lymphocytic leukemia with the monoclonal anti-CD20 antibody rituximab.
Hickish et al., "Molecular monitoring of low grade non-Hodgkin's lymphoma by gene amplification", Br. J. Cancer, 1991, vol. 64, pp. 1161-1163.
Hiddemann et al., "New Aspects in the Treatment of Advanced Low-Grade Non-Hodgkin's Lymphomas: Prednimustine/Mitoxantrone Versus Cyclophosphamide/Vincristine/Prednisone Followed by Interferon Alfa Versus Observation Only—A Preliminary Update of the German Low-Grade Lymphoma Study Group", Seminars in Hematology, 1994, vol. 31, No. 2, Suppl 3, pp. 32-35.
Hiddemann W. Blood 88(11): 4085-89, 1996. Lymphoma between et al. classification—the gap biology and clinical management is closing.
Hiddemann, "Non-Hodgkin's Lymphomas—Current Status of Therapy and Future Perspectives", European Journal of Cancer vol. 31A (13/14) 1995, pp. 2141-2145.
Hiddemann, et al. "Lymphomas: New Recognitions and Therapy Strategies", Ch. 11, C.H. Beck, Thieme Georg Verlag, 2005, pp. 78-81 (Translated).
Hillmen P. et al. Semin. Oncol. 31(1 suppl. 2): 22-26, 2004. Advancing therapy for chronic lymphocytic leukemia—the role of rituximab.
Hochster et al., "Maintenance rituximab after cyclophosphamide, vincristine, and prednisone prolongs progression-free survival in advanced indolent lymphoma: Results of the randomized phase III ECOG1496 Study," J. Clin. Oncol. 27(10): 1607-1614 (2009).
Hochster et al.: "Maintenance Rituximab After CVP Results in Superior Clinical Outcome in Advanced Follicular Lymphoma (FL) : Results of the E1496 Phase III Trial From the Eastern Cooperative Oncology Group and The Cancer and Leukemia Group," Blood, vol. 106, No. 11, pt. 1, Nov. 1, 2005 (Nov. 1, 2005), p. 106A.
Hochster, H.S., et al., "Results of E1496: A phase III trial of CVP with or without maintenance rituximab in advanced indolent lymphoma (NHL)", Journal of Clinical Oncology, 2004 ASCO Annual Meeting, vol. 22, No. 14S (Jul. 15 Supplemental), 2004: 6502, pp. 1-2.
Hoerni et al., "Maintenance Immunotherapy with BCG in Non-Hodgkin's Malignant Lymphomas: a Progress Report of a Randomized Trial", Recent Results in Cancer Research, 1980, vol. 80, pp. 92-97.
Hoerni et al., "Successful Maintenance Immunotherapy by BCG of Non-Hodgkin's Malignant Lymphomas: Results of a Controlled Trial", British J. Haematology, 1979, vol. 42, pp. 507-514.
Hooijberg E. et al. Cancer Res. 55: 2627-34, 1995. Eradication of large human B cell tumors in nude mice with unconjugated CD20 monoclonal antibodies and interleukin 2.
Horning S.J. et al. Blood 100(11 part 1): 357a, abst. No. 1385, 2002. Rituximab treatment failures: tositumomab and Iodine I 131 tositumomab (Bexxar®) can produce meaningful durable responses.
Horning, S. et al., "Response criteria (RC) and quality assurance (QA) of responses in the evaluation of new therapies for patients (pts) with low-grade lymphoma (LG NHL)", Proc Am Soc Clin Oncol 16:18a (#62), May 1997.
Hultin et al., "CD20 (pan-B cell) antigen is expressed at a low level on a subpopulation of human T lymphocytes", Cytometry 1993; 14(2):196-204 (Abstract only—1 page), www.ncbi.nlm.nih.gov/pubmed/7679964 (Retrieved Mar. 26, 2013).
Hurwitz et al., "A Synergistic Effect Between Anti-Idiotype Antibodies and Antineoplastic Drugs in the Therapy of a Murine B-Cell Tumor." Intl. J. Cancer 37(5): 739-45 (May 1986).
IDEC Pharmaceuticals Corp. and Genentech, Inc., Product insert for RITUXAN® approved by U.S. Food and Drug Administration on Nov. 26, 1997.

(56) References Cited

OTHER PUBLICATIONS

IDEC Pharmaceuticals Corp., press release dated Dec. 9, 1996. IDEC Pharmaceuticals and Genentech announce positive final results for pivotal phase III trial of IDEC-C2B8 as single agent. (3 pages).
IDEC Pharmaceuticals Corp., U.S. Securities and Exchange Commission Form S-1 Registration Statement, 1991.
*IDEC Pharmaceuticals v. Corixa Corp.*, Case No. 01-1637-IEG [Doc. Nos. 486, 584] (S.D. Cal.) Oct. 14, 2003. pp. 1-14.
Imrie K. et al. *Curr. Oncol.* 6(4): 228-35, 1999. Use of rituximab in the treatment of lymphoma: an evidence summary.
International Disclosure Staement Form PTO-1449 considered by examiner on May 10, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-31.
International Non-Hodgkin's Lymphoma Prognostic Factors Project, "A Predictive Model for Aggressive Non-Hodgkin's Lymphoma," *N Engl. J Med* 329(14): 987-994 (1993).
Jain R.K. *Sci. Am.* 271(1): 58-65, 1994. Barriers to drug delivery in solid tumors.
James, J.S. and Dubs, G., "FDA approves new kind of lymphoma treatment. Food and Drug Administration" AIDS Treat News, Dec. 5, 1997; (No. 284):2-3 (Abstract only), http://www.ncbi.nlm.nih.gov/pubmed/11364912 (Retrieved Feb. 4, 2013).
Janakiraman N. et al. *Blood* 92(10 Suppl. 1): 337a, abst. No. 1384, Nov. 1998. Rituximab: correlation between effector cells and clinical activity in NHL.
Jazirehi A.R. et al. *Oncogene* 24: 2121-43, 2005. Cellular and molecular signal transduction pathways modulated by rituximab (rituxan, anti-CD20 mAb) in non-Hodgkin's lymphoma: implications in chemosensitization and therapeutic intervention.
Jensen M. et al. *Ann. Hematol.* 77: 89-91, 1998. Rapid tumor lysis in a patient with B-cell chronic lymphocytic leukemia and lymphocytosis treated with an anti-CD20 monoclonal antibody (IDEC-C2B8, rituximab).
Jones et al., "Improved Complete Remission Rates and Survival for Patients with Large Cell Lymphoma Treated with Chemoimmunotherapy", Cancer, 1983, vol. 51, pp. 1083-1090.
Juweid M. et al. *Cancer Res.* 55(23 Suppl.): 5827s-5831s, 1995. Estimates of red marrow. dose by sacral scintigraphy in radioimmunotherapy patients having non-Hodgkin's lymphoma and diffuse bone marrow uptake.
Juweid M. et al. *Cancer Res.* 55(23 Suppl.): 5899s-5907s, 1995. Treatment of non-Hodgkin's lymphoma with radiolabeled murine, chimeric, or humanized LL2, an anti-CD22 monoclonal antibody.
Kaminski M. et al. *Antibody Immunoconj. Radiopharm.* 3(1): abst. No. 83, 1990. Radioimmunotherapy of advanced B-cell lymphoma with non bone marrow ablative doses of 131-I MB-1 antibody.
Kaminski M. et al. *Antibody Immunoconj. Radiopharm.* 4(1): 36, abst. No. 66, 1991. Phase I trial results of 131-1 antibody radioimmunotherapy (RAIT) of B-cell lymphoma.
Kaminski M. et al. *J. Clin. Oncol.* 10(11): 1696-1711, 1992. Imaging, dosimetry , and radioimmunotherapy with iodine 131-labeled anti-CD37 antibody in B-cell lymphoma.
Kaminski M. et al. *Proc. Amer. Soc. Clin. Oncol.* 9: 271, abst. No. 1051, 1990. Radioimmunodetection (RID) and non marrow ablative radioimmunotherapy (RIT) of B-cell lymphoma with 131-I MB-1 antibody.
Kaminski M. et al. Proc. Third Conf. on Radioimmunodetection and Radioimmunotherapy of Cancer, Princeton NJ, Nov. 15-17, 1990 (published at Antibody Immunoconj. Radiopharm. 4: 387, 1991), abst. No. 144. 131-1 anti-B1: Initial clinical evaluation in B-cell lymphoma.
Kaminski M.S. et al. *Antibody Immunoconj. Radiopharm.* 5(3): 345, abst. no. 57, 1992. Initial clinical radioimmunotherapy results with $^{131}$I-anti-B1 (anti-CD20) in refractory B-cell lymphoma.
Kaminski M.S. et al. *Blood* 76(10 Suppl. 1): 355a, abst. No. 1409, 1990. Phase I evaluation of 131-1 MB-1 antibody radioimmunotherapy (RIT) of B-cell lymphoma.
Kaminski M.S. et al. *Blood* 78(10 Suppl. 1): 43a, abst. No. 161, 1992. Radioimmunotherapy (RIT) of refractory B-cell lymphoma with 131-I-anti-B1 (anti-CD20) antibody: promising early results using non-marrow ablative radiation doses.
Kaminski M.S. et al. *J. Clin. Oncol.* 14(7): 1974-81, 1996. Iodine-131-anti-B1 radioimmunotherapy for B-cell lymphoma.
Kaminski M.S. et al. *N Engl. J Med.* 329: 459-65, 1993. Radioimmunotherapy of B-cell lymphoma with [$^{131}$I]anti-B1 (anti-CD20) antibody.
Kaplan EL et al., "Nonparametric estimation from incomplete observations." J Am Stat Assoc, 1958, vol. 53, pp. 457-481.
Keating M. et al. *Semin. Oncol.* 27(6 suppl. 12): 86-90, 2000. High-dose rituximab therapy in chronic lymphocytic leukemia.
Kennedy et al., "Incidence and nature of CD20-negative relapses following rituximab therapy in aggressive B-cell non-Hodgkin's lymphoma: a retrospective review," *Br. J. Haematol.* 119(2): 412-6 (2002).
Khan et al., "A Phase 2 Study of Rituximab in Combination with Recombinant Interleukin-2 for Rituximab-Refractory Indolent Non-Hodgkin's Lymphoma," Clin Cancer Res 12(23):7046-7053 (2006).
Kimby, "Beyond immunochemotherapy: combinations of rituximab with cytokines interferon-alpha2a and granulocyte colony stimulating factor," *Semin. Oncol.* 29(2 Suppl. 6): 7-10 (2002).
King and Younes, "Rituximab: review and clinical applications focusing on non-Hodgkin's lymphoma," *Expert Rev. Anticancer Ther.* 1(2): 177-86 (2001).
Kinoshita T. et al. *J. Clin. Oncol.* 16(12): 3916, Dec. 1998. CD20-negative relapse in B-cell lymphoma after treatment with Rituximab.
Klarnet J.P. et al. *J. Immunol.* 138(11): 4012-17, 1987. Antigen-driven T cell clones can proliferate in vivo, eradicate disseminated leukemia, and provide specific immunologic memory.
Knox S.J. et al. *Clin. Cancer Res.* 2: 457-70, 1996. Yttrium-90-labeled anti-CD20 monoclonal antibody therapy of recurrent B-cell lymphoma.
Knox S.J. et al. *J Immunother.* 16(2): 161, abst. No. 51, 1994. $^{90}$Y-anti-CD20 monoclonal antibody therapy (IDEC-Y2B8) for recurrent B cell lymphoma.
Knox S.J. et al. *I.J. Rad. Oncol. Biol.Phys.* 32: 215, 1995. $^{90}$Y-anti-CD20 monoclonal antibody therapy for recurrent B cell lymphoma.
Kohler and Milstein, "Derivation of Specific Antibody-Producing Tissue culture and Tumor Lines by Cell Fusion", European J. Immunology, 1976, vol. 6, pp. 511-519.
Kuzel T. et al. *Cancer Biother.* 8(1): 3-16, 1993. A phase I escalating-dose safety, dosimetry and efficacy study of radiolabeled monoclonal antibody LYM-1.
Kwak et. al., "Biological response modifiers", The Non-Hodgkin's Lymphomas, 2$^{nd}$ edition, Ch. 32, Ian T. MaGrath, Arnold, 1997, pp. 699-714.
Langmuir V.K. *NucL Med. Biol.* 19(2): 213-55, 1992. Radioimmunotherapy: clinical results and dosimetric considerations.
Larson S.M. et al. *Nucl. Med. Biol.* 16: 153-58, 1989. Comparison of bone marrow dosimetry and toxic effect of high dose $^{131}$I-labeled monoclonal antibodies administered to man.
Lauria F. et al. *Bone Marrow Transplant.* 18(1): 79-85, 1996. Immunologic and clinical modifications following low-dose subcutaneous administration of rIL-2 in non-Hodgkin's lymphoma patients after autologous bone marrow transplantation.
Lazzarino, M. et al., "Immunochemotherapy with rituximab, vincristine and 5-day cyclophosphamide for heavily pretreated follicular lymphoma." Oncology. 2005;68(2-3):146-53.
Lefrak et al., "A clinicopathologic analysis of adriamycin cardiotoxicity" Cancer 32(2) 1973, pp. 302-314 (Abstract only—pp. 1-3).
Leget et al., "Use of rituximab, the new FDA-approved antibody", *Current Opinion in Oncology* 10, 1998, pp. 548-551.
Leichner P.K. et al. *Front. Rad. Ther. Oncol.* 24: 109-20, 1990. Dosimetry and treatment planning in radioimmunotherapy.
Leichner P.K. et al. *Med. Phys.* 20(2): 529-34, 1993. Tumor dosimetry in radioimmunotherapy: methods of calculation for beta particles.

(56) References Cited

OTHER PUBLICATIONS

Leonard et. al., "Monoclonal Antibody Therapy of Lymphoma", American Cancer Society Atlas of Clinical Oncology Malignant Lymphomas, Ch. 18, Michael L. Grossbard, BC Decker Inc. 2002, pp. 301-315.
Levy R. et al. *Fed. Proc.* 42: 2650-56, 1983. Tumor therapy with monoclonal antibodies.
Li Tongdu (chief translator), Clinical Oncology, Anhui Science and Technology Publication, vol. 28-3, pp. 34-45, 1996 and English translation.
Ling N.R. et al. (in) *Leucocyte Typing III: White Cell Differentiation Antigens*, A.J. McMichael et al., eds., Oxford: Oxford Univ. Pr., 1987, pp. 302-335. B-cell and plasma cell antigens: new and previously defined clusters.
Link B.K. et al. *Proc. Amer. Soc. Clin. OncoL* 17: 3a, abst. No. 7, 1998. Phase II pilot study of the safety and efficacy of rituximab in combination with CHOP chemotherapy in patients with previously untreated intermediate- or high-grade NHL.
Link M.P. et al. *I Immunol.* 137(9): 3013-18, 1986. A unique antigen on mature B-cells defined by a monoclonal antibody.
Lipton J.M. et al. *Blood* 60(5 Suppl. 1): 170a, abst. No. 609, 1992. Distribution of B1, CALLA, 02 microglobulin and IA on hematopoiesis supporting cells (HSC) in short and long-term cultures.
Lister, "The management of follicular lymphoma", Annals of Oncology, Supplement 2, vol. 2, pp. 131-135, (1991).
Liu A.Y. et al. *J. Immunol.* 139(10): 3521-26, Nov. 1987. Production of a mouse-human chimeric monoclonal antibody to CD20 with potent Fc-dependent biologic activity.
LoBuglio AF et al., "Mouse/human chimeric monoclonal antibody in man: Kinetics and Immune response." PNAS, 1989, vol. 86, pp. 4220-4224.
Lonberg N. et al. *Nature* 368: 856-59, 1994. Antigen-specific human antibodies from mice comprising four distinct genetic modifications.
Longo DL, "Immunotherapy for Non-Hodgkin's Lymphoma." Curr. Opin. Oncol. 8(5): 353-59 (Sep. 1996).
Lopez-Guillermo A et al., "The molecular breakpoint site of bcl-2 gene has prognostic importance in indolent follicular lymphoma.", Blood, Nov. 1996, vol. 88, No. 10, Suppl 1 Part 1 of 2, Abstract 1162, p. 293a.
Lopez-Guillermo et al. "The clinical significance of molecular response in indolent follicular lymphomas", Blood, Apr. 1998, vol. 91, No. 8, pp. 2955-2960.
Lowman H.B. Slides presented at IBC Antibody Engineering Conference, Dec. 2, 2003. Differential activities in a series of humanized anti-CD20 antibodies.
Lum L.G. et al. *Blood* 69(2): 369-80, 1987. The kinetics of immune reconstitution after human marrow transplantation.
MabThera® EU Marketing Authorization: EU/1/98/067/002; Summary of Product Characteristics; Date of first authorization: Jun. 2, 1998; Date of latest renewal: Jun. 2, 2008, pp. 1-94.
Macey D.J. et al. *Front. Rad. Ther. Oncol.* 24: 123-31, 1990. A treatment planning program for radioimmunotherapy.
Macklis R.M. et al. *Antibody Immunoconj. Radiother.* 5(3): abst. No. 39, 1992. Induction of programmed cell death in malignant lymphomas after radioimmunotherapy.
Macklis R.M. et al. *Cancer* 73(3 Suppl.): 966-73, 1994. Radiobiologic studies of low-doserate $^{90}$Y-lymphoma therapy.
Maddy A.H. et al. *Immunol.* 68(3): 346-52, 1989. The role of cell maturation in the generation of phenotypic heterogeneity in B-cell chronic lymphocytic leukaemia.
Maloney D.C. et al. *Blood* 90(6): 2188-2195, 1997. IDEC-C2B8 (Rituximab) anti-CD20 monoclonal antibody therapy in patients with relapsed low-grade non-Hodgkin's lymphoma.
Maloney D.G. et al. *Blood* 80(6): 1502-1510, 1992. Monoclonal anti-idiotype antibody therapy of B-cell lymphoma: the addition of a short course of chemotherapy does not interfere with the antitumor effect nor prevent the emergence of idiotype-negative variant cells.
Maloney D.G. et al. *Blood* 84(8): 2457-66, 1994. Phase I clinical trial using escalating single-dose infusion of chimeric anti-CD20 monoclonal antibody (IDEC-C2B8) in patients with recurrent B-cell lymphoma.
Maloney D.G. et al. *Blood* 88(10: Suppl. 1): 637a, abst. No. 2635, 1996. The anti-tumor effect of monoclonal anti-CD20 antibody (mAb) therapy includes direct anti-proliferative activity and induction of apoptosis in CD20 positive non-Hodgkin's lymphoma (NHL) cell lines.
Maloney D.G. et al., "IDEC-C2B8: results of a phase 1 multiple-dose trial in patients with relapsed non-Hodgkin's Lymphoma", J Clin Oncol., Oct. 1997, vol. 15, No. 10, pp. 3266-3274.
Maloney et al., "IDEC-C2B8: Results of a Phase I Multiple-Dose Trial in Patients with Relapsed Non-Hodgkin's Lymphoma", Journal of Clinical Oncology, vol. 15, No. 10, Oct. 1977, pp. 3266-3274.
Maloney et al., "Newer Treatments for Non-Hodgkins Lymphoma: Monoclonal Antibodies", Oncology vol. 12, No. 10, Oct. 2, 1998, pp. 1-21 http://www.cancernetwork.com/display/article/10165/72098 (Retrieved 1998) Article also published in: Maloney et al., Oncology 12(Suppl 8):63-76 (1998).
Maloney, D.G., et al., "Chimeric Anti-CD20 (IDEC-C2B8) Monoclonal Antibody Therapy of Low-Grade Lymphoma", Cancer Invest 15(1 Suppl):78-79 (#70), 1997.
Maloney, D.G., et al., "IDEC-C2B8 Anti-CD20 Antibody: Results of Long-Term Follow-Up of Relapsed NHL Phase II Trial Patients", Blood 86(10):54a (#205), Nov. 1995.
Maloney, D.G., et al., "IDEC-C2B8: Final report on a Phase II trial in relapsed non-Hodgkin's lymphoma", Blood 84(10) Supplement 1:169a (#661), 1994.
Maloney, D.G., et al., "Initial Report on a Phase I/II Multiple Dose Clinical Trial of IDEC-C2B8 (Chimeric Anti-CD20) in Relapsed B-Cell Lymphoma", Proc Am Soc Clin Oncol 13:304 (#993) Mar. 1994.
Maloney, D.G., et al., "Phase I Clinical Trial Using Escalating Single Dose Infusion of Chimeric Anti-CD20 Monoclonal Antibody (IDEC-C2B8) in Patients with Recurrent B-Cell Lymphoma)", Blood 82(10 Suppl 1): 445a (#1763), Nov. 1993.
Maloney, D.G., et al., "Phase I/II Clinical Trials of IDEC-C2B8 (Chimeric Anti-CD20 Antibody) in Relapsed B-Cell Lymphoma", *Cancer Investigation*, vol. 13, Suppl 1, pp. 31-32 (#24), 1995.
Mange et al., "Immunotherapy with rituximab following high-dose therapy and autologous stem-cell transplantation for mantle cell lymphoma," Semin. Oncol. 29(1 Suppl. 2): 56-69 (2002).
Marcus et al., "CVP chemotherapy plus rituximab compared with CVP as first-line treatment for advanced follicular lymphoma," *Blood* 105: 1417-1423 (2005).
Mariuzza et al. *Science.* 233: 747-53, 1986. Three-dimensional structure of an antigen-antibody complex at 2.8 A resolution.
Marquez S.D. et al. *I.J. Rad. Oncol. Biol. Phys.* 39: 327, abst. No. 2173, 1997. Hematological toxicity in radioimmunotherapy is predicted both by the computed absorbed whole body dose (cGy) and by the administered dose (mCi).
Marti G.E. et al. *Ann. N.Y. Acad. Sci.* 651: 480-83, 1992. CD20 and CD5 expression in B-chronic lymphocytic leukemia.
Marx J.L. *Science* 229(4712): 455-56, 1985. Antibodies made to order.
Masucci G. et al. *Med. Oncol. Tumor Pharmacother.* 8(3): 207-20, 1991. Chemotherapy and immunotherapy of colorectal cancer.
Mazza P. et al. *Bone Marrow Trans.* 23: 1273-78, 1999. Analysis of feasibility of myeloablative therapy and autologous peripheral stem cell (PBSC) transplantation in the elderly: an interim report.
McLaughlin et al., "Management of Patients with Nodular Lymphoma", UT M.D. Anderson Clinical Conference on Cancer, 1984, vol. 27, pp. 301-312.
McLaughlin et al., *Semin Oncol* 26(5, 14 Suppl):79-87, Oct. 1999 "Rituximab in Indolent Lymphoma: The Single-Agent Pivotal Trial".
McLaughlin p. et al., "Fludarabine phosphate in lymphoma: an important new therapeutic agent" in Advances in Lymphoma Research, Boston, MA, Cabanillas F, Rodriguez, MA, Kluwer Academic Publishers, 1996, pp. 3-14.
McLaughlin P, et al., "A Phase III (PIII) pivotal trial of IDEC-C2B8 in patients (pts) with relapsed low-grade or follicular lymphoma."J Mol Med 75(7):B231 (#257), Jul. 1997.

(56) References Cited

OTHER PUBLICATIONS

McLaughlin P. et al. *Blood* 92(10 Suppl. 1): 414a-415a, abst. No. 1712, Nov. 1998. Efficacy controls and long-term follow-up for relapsed or refractory, low-grade or follicular (R-LG/F) NHL.

McLaughlin P. et al. *J. Clin. Oncol.* 16(8): 2825-33, Aug. 1998. Rituximab chimeric-antiCD20 monoclonal antibody therapy for relapsed indolent lymphoma: half of patients respond to a four-dose treatment program.

McLaughlin P. et al. *J. Clin Oncol.* 16(8): 2825-2833, Aug. 1998. "Rituximab chimeric-anti-CD20 monoclonal antibody therapy for relapsed indolent lymphoma: half of patients respond to a four-dose treatment program" (Previously submitted); with e-mail from publisher Glenn Landis dated Nov. 5, 2012, 1 page, stating the official publication date thereof was Aug. 1, 1998.

McLaughlin P. et al. *Oncology* 12(12): 1763-81, 1998. Clinical status and optimal use of rituximab for B-cell lymphomas.

McLaughlin P. et al., "IDEC-C2B8 (Rituximab): Clinical activity in clinically-chemoresistant (CCRD) low-grade or follicular lymphoma (LG/F NHL) and in patients (pts) relapsing after anthracycline therapy (ANTHRA-RX) or ABMT.", Proc Am Soc Clin Oncol, May 1997, vol. 16, Abstract #55, p. 16a.

McLaughlin P. et al., "IDEC-C2B8 anti-CD20 antibody: Final report on a Phase III pivotal trial in patients (PTS) with relapsed low-grade or follicular lymphoma (LG/F NHL).", Blood 88(10):90a (#349), Nov. 1996.

McLaughlin P. et al., "Pharmacokinetics (PK) and Pharmacodynamics (PD) of the anti-CD20 antibody (MAB) IDEC-C2B8 in patients (PTS) with relapsed low-grade or follicular lymphoma (LG/F NHL)" Blood (Abstract #350) 88(10 Suppl 1, Part 1 of 2):90a (Nov. 1996).

McLaughlin P. et al., "Pivotal Phase III clinical trial (PIII CT) of the chimeric anti-CD20 antibody (MAB) IDEC-C2B8 in patients (PTS) with relapsed low-grade or follicular lymphoma (LG/F NHL;): A preliminary report.", Ann Oncol 7 (3 Suppl):57 (#194), Jun. 1996.

McLaughlin P. et al., "Preliminary report on a Phase III pivotal trial of the anti-CD20 antibody (MAB) IDEC-C2B8 in patients (PTS) with relapsed low-grade or follicular lymphoma." Proc Am Soc Clin Oncol 15:417 (#1281), May 1996.

McLaughlin, P. et al., "Clinical Status and Optimal Use of Rituximab for B-Cell Lymphomas", Dec. 1998, Oncology, 12(12):1763-1781.

McNeil, C. "Non-Hodgkin's Lymphoma Trials in Elderly Look Beyond CHOP", Journal of the National Cancer Institute, Feb. 18, 1998, vol. 90, No. 4, pp. 266-267.

Meeker, T.C. et al., "A clinical trial of anti-idiotype therapy for B cell malignancy", *Blood* 1985; 65: 1349-1363.

Meredith R.F. et al. *J. Nucl. Med.* 33(9): 1648-53, 1992. Dose fractionation of radiolabeled antibodies in patients with metastatic colon cancer.

Meyer, et. al., "Randomized Phase II Comparison of Standard CHOP with Weekly CHOP in Elderly Patients with Non-Hodgkin's Lymphoma", Journal of Clinical Oncology, Sep. 1995, vol. 13, No. 9, pp. 2386-2393.

Miller, R.A. et al., "Treatment of B-Cell Lymphoma with monoclonal anti-idiotype antibody.", N Engl J Med 306(9): 517-522, 1982.

Mishell B.E. et al., eds. *Selected Methods in Cellular Immunology*, San Francisco: Freeman, 1980, p. 287-304. Modification and use of antibodies to label cell surface antigens.

Misset et al., "Dose-finding study of docetaxel and doxorubicin in first-line treatment of patients with metastatic breast cancer", *Annals of Oncology* 10, 1999, pp. 553-560.

Monnereau et al., "L'interféron alpha dans le traitement des lymphomes non hodgkiniens de faible malignité", *Bulletin du Cancer*, vol. 85, No. 10, 1998, pp. 855-65, in French with English translation, pp. 1-19.

Morrison and Peterson, "Combination chemotherapy in the treatment of follicular low-grade lymphoma," *Leuk. Lymphoma* 10 Suppl.: 29-33 (1993).

Morrison S. et al. *Proc. Nat'l Acad. Sci. USA* 81: 6851-54, 1984. Chimeric human antibody molecules: mouse antigen-binding domains with human constant region domains.

Morrison S.L. *Science* 229: 1202-07, 1985. Transfectomas provide novel chimeric antibodies.

Morrison, et al., "Dose intensity of CHOP alone or with rituximab in diffuse large B-cell lymphoma (DLBCL) in patients >60 years of age: an analysis of the intergroup trial (CALGB 9793, ECOG-SWOG 4494)", [Abstract] Ann Oncol 16 (Supp! 5): A-224, v102, 2005.

Morrison, et al., "Maintenance rituximab (MR) compared to observation (OBS) after R-CHOP or CHOP in older patients (pts) with diffuse large B-cell lymphoma (DLBCL): An Intergroup E4494/C9793 update", [Abstract] *J Clin Oncol* 25 (Suppl 18): A-8011, 443s, 2007.

Mueller BM et al., "Enhancement of antibody-dependent cytotoxicity with a chimeric anti-GD2 antibody." J Immunol, 1990, vol. 144, pp. 1382-1386.

Multani P.S. et al. *J. Clin. Oncol.* 16(11): 3691-3710, 1998. Monoclonal antibody-based therapies for hematologic malignancies.

Munro A. *Nature* 312: 597, 1984. Uses of chimeric antibodies.

Murray J.L. et al. *I Biol. Resp. Modifiers* 9(6): 556-63, 1990. Recombinant alpha-interferon enhances tumor targeting of an antimelanoma monoclonal antibody in vivo.

Murray J.L. et al. *J. Nucl. Med.* 26: 3328-29, 1985. The effect of radionuclide dose on imaging with indium-111-labeled anti P-97 monoclonal antibody.

Muzaffar S. et al., "Immunophenotypic analysis of non-Hodgkin's lymphoma", J Pak Med Assoc., Apr. 1997, vol. 47, No. 4, pp. 106-109.

Nadler L.M. et al. *Cancer Res.* 40(9): 3147-54, 1980. Serotherapy of a patient with a monoclonal antibody directed against a human lymphoma-associated antigen.

Nadler L.M. et al. *J. Clin. Invest.* 67: 134-140, 1981. A unique cell surface antigen identifying lymphoid malignancies of B cell origin.

Nadler L.M. et al. *J. Clin. Invest.* 74(2): 332-40, 1984. B cell origin of non-T cell acute lymphoblastic leukemia. A model for discrete stages of neoplastic and normal pre-B cell differentiation.

Nadler L.M. et al. *Lancet* 2(8400): 427-31, 1984. Anti-B1 monoclonal antibody and complement treatment in autologous bone-marrow transplantation for relapsed B-cell non-Hodgkin's lymphoma.

Nakamura K. et al. *Oncology* 50(1): 35-40, 1993. Effect of alpha-interferon on anti-alpha fetoprotein-monoclonal-antibody targeting of hepatoma.

National Cancer Institute: Surveillance, Epidemology, and End Results Program, "SEER Stat Fact Sheets: Non-Hodgkin Lymphoma", http://seer.cancer.gov/statfacts/html/nhl.html, Apr. 2014, pp. 1-9 (retrieved Dec. 2, 2014).

Neuberger M.S. et al. *Nature* 314: 268-70, 1985. A hapten-specific chimaeric IgE antibody with human physiological effector function.

Nguyen D.T. et al., "IDEC-C2B8 anti-CD20 (rituximab) immunotherapy in patients with low-grade non-Hodgkin's lymphoma and lymphoproliferative disorders: evaluation of response on 48 patients", Eur J Haematol., Feb. 1999, vol. 62, No. 2, pp. 76-82.

Nielsen B. et al. *Eur. J Haematol.* 48(3): 146-51, 1992. Interferon-a-induced changes in surface antigens in a hairy-cell leukemia (JOK-1), and a Burkitt's lymphoma cell line (Daudi) during in vitro culture.

Non-Hodgkin's Lymphoma Pathologic Classification Project. *Cancer* 49(10): 2112-35, 1982. National Cancer Institute sponsored study of classifications of non-Hodgkin's lymphomas.

Notice of Allowability dated Jun. 26, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-2.

O'Brien S. *Blood* 92(10 Suppl 1): 105a, abst. No. 431, 1998. Phase I/II study of rituxan in chronic lymphocytic leukemia (CLL).

O'Brien S. et al. *N Engl. J. Med.* 330(5): 319-22, 1994. Lack of effect of 2chlorodeoxyadenosine therapy in patients with chronic lymphocytic leukemia refractory to fludarabine therapy.

O'Brien S.M. et al. *J. Clin. Oncol.* 19: 2165-70, 2001. Rituximab dose-escalation trial in chronic lymphocytic leukemia.

(56) References Cited

OTHER PUBLICATIONS

Oettgen H.C. et al. *Hybridoma* 2(1): 17-28, 1983. Further biochemical studies of the human B-cell differentiation antigens B1 and 132.
Office Action mailed by the USPTO dated Feb. 29, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-12.
Office Restriction Requirement dated Oct. 15, 2009 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 1-5.
Official Action mailed by the USPTO dated May 11, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Onrust et al., "Rituximab" *Drugs* 58(1), 1999, pp. 79-88.
Orura et al., "Therapeutic future direction with new clinical trials for refractory lymphoid malignancies", *Journal of Japan Lymphoreticular System Society*, 1997, 37, 4, 285-296.
Ozato K. et al. *J. Immunol*. 126(1): 317-21, 1981. Monoclonal antibodies to mouse MHC antigens. III. Hybridoma antibodies reacting to antigens of the H-2b haplotype reveal genetic control of isotype expression.
Ozer et al., "Recombinant interferon-alpha therapy in patients with follicular lymphoma," *Cancer* 82(10): 1821-30 (1998).
Palmieri et al., "Maintenance therapy with recombinant interferon alpha-2B (αIFN) in prognostically unfavourable aggressive non-Hodgkin's lymphomas (NHL)" *Oncology Reports* 3: 1996, pp. 733-735.
Panka D.J. et al. *Proc. Nat'l. Acad. Sci*. 85: 3080-84, 1988. Variable region framework differences result in decreased or increased affinity of variant anti-digoxin antibodies.
Parker B.A. et al. *Cancer Res*. 50(3): 1022s-1028s, 1990. Radioimmunotherapy of human 13-cell lymphoma with $^{90}$Y-conjugated antiidiotype monoclonal antibody.
Patent Owner's Updated Mandatory Notices in Petition for Inter Partes Review of U.S. Pat. No. 8,329,172 dated May 11, 2015 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-4.
PDQ—NCI's Comprehensive Cancer Database, http://web.archive.org/web/19980116194104/http://cancernet.nci.nih.gov/pdq.htm (archived Jan. 16, 1998) pp. 1-2 (retrieved Dec. 4, 2014).
Pearson J.W. et al. *Cancer Res*. 49(18): 4990-95, 1989 Enhanced therapeutic efficacy of an immunotoxin in combination with chemotherapy against an intraperitoneal human tumor xenograft in athymic mice.
Peterson et. al., "Cyclophosphamide versus cyclophosphamide plus interferon alfa-2b in follicular low-grade lymphomas: an intergroup phase III trial (CALGB 8691 and EST 7486)", Proceedings of ASCO, May 17-20, 1997, vol. 16, Abstract 48, p. 14a.
Petition for Inter Partes Review of U.S. Pat. No. 8,329,172 (U.S. Appl. No. 11/840,956, Antonio J. Grillo-Lopez, Combination Therapies for B-Cell Lymphomas Comprising Administration of Anti-CD20 Antibody, filed Aug. 18, 2007) dated Dec. 15, 2014 pp. 1-76.
Petitioner's Request for Rehearing on the Institution Decision in Inter Partes Review of U.S. Pat. No. 8,329,172 dated Dec. 15, 2014 (U.S. Appl. No. 11/840,956, Antonio Grillo-Lopez, Combination Therapies for B-Cell Lymphomas Comprising Administration of Anti-CD20 Antibody, filed Aug. 18, 2007) pp. 1-18.
Petryk et.al., "Indolent B-Cell Lymphomas", American Cancer Society Atlas of Clinical Oncology Malignant Lymphomas, Ch. 6, Michael L. Grossbard, BC Decker Inc. 2002, pp. 94-111.
Petryk M. et al. *Oncologist 6*: 317-26, 2001. ASCO 2001: Critical commentaries: Hematologic malignancies.
Pettengell, et. al., "Randomised study of rituximab in patients with relapsed or resistant follicular lymphoma prior to high-dose therapy as in vivo purging and to maintain remission following high-dose therapy", J. Clin. Oncol., 2010, vol. 18, Supp. 10, abstr. 8005 (2 pages).

Pettengell, Ruth (on behalf of the EBMT Lymphoma Working Party), "Randomised study of rituximab (MabThera) in patients with relapsed or resistant follicular lymphoma prior to high dose therapy as in vivo purging and to maintain remission (NCT00005589)", slides presented by the European Group for Blood and Marrow Transplantation at the 2010 ASCO Annual Meeting (20 pages).
Pfreundschuh et al., "CHOP-like chemotherapy plus rituximab versus CHOP-like chemotherapy alone in young patients with good-prognosis diffuse large-B-cell lymphoma: a randomised controlled trial by the MabThera International Trial (MInT) Group", Lancet Oncol 2006; 7:379-91.
Pietersz G.A. et al. *Immunol. Cell. Biol*. 65(2): 111-25, 1987. The use of monoclonal antibody conjugates for the diagnosis and treatment of cancer.
Piro L. et al. *Blood* 90(10 Suppl. 1): 510a, abst. No. 2272, 1997. RITUXAN™ (rituximab, IDEC-C2B8): Interim analysis of a phase II study of once weekly times 8 dosing in patients with relapsed low-grade or follicular non-Hodgkin's lymphoma.
Piro L.D. et al. *Ann. Oncol*. 10: 655-61, 1999. Extended Rituximab (anti-CD20 monoclonal antibody) therapy for relapsed or refractory low-grade or follicular non-Hodgkin's lymphoma.
Piro LD, "Cladribine in the treatment of low-grade non-Hodgkin's lymphoma." Semin Hematol, 1996, vol. 33, No. 1, Suppl 1, pp. 34-39.
Pitini et al. "Interleukin-2 and Lymphokine-Activated Killer Cell Therapy in Patients with Relapsed B-Cell Lymphoma Treated with Rituximab," Clin Cancer Res 13(18):5497 (2007).
Polyak M.J. et al. *Blood* 99: 3256-62, 2002. Alanine-170 and praline-172 are critical determinants for extracellular CD20 epitopes; heterogeneity in the fine specificity of CD20 monoclonal antibodies is defined by additional requirements imposed by both amino acid sequence and quaternary structure.
Portlock, C.S. and Rosenberg, S.A., "Combination chemotherapy with cyclophosphamide, vincristine, and prednisone in advanced non-Hodgkin's lymphomas" *Cancer* 37(3); 1976, pp. 1275-1282.
Pott-Hoeck C. et al., "Purine analogs in the treatment of low-grade lymphomas and chronic lymphocytic leukemias." Ann Oncol, 1995, vol. 6, pp. 421-433.
Poynton CH et al., "Adverse reactions to Campath-1H monoclonal antibody." Lancet , 1993, vol. 341, p. 1037.
Preliminary Amendment filed Oct. 31, 2007 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-5.
Press O.W. *Cancer I Sci. Amer*. 4(Suppl 2): S19-S26, Jul. 1998. Prospects for the management of non-Hodgkin's lymphomas with monoclonal antibodies and immunoconjugates.
Press O.W. et al. *Adv. Exp. Med. Biol*.303: 91-96, 1991. Radiolabeled antibody therapy of human B cell lymphomas.
Press O.W. et al. *Blood* 69(2): 584-91, 1987. Monoclonal antibody 1F5 (anti-CD20) serotherapy of human B cell lymphomas.
Press O.W. et al. *Cancer Res*. 49(17): 4906-12, 1989. Endocytosis and degradation of monoclonal antibodies targeting human B-cell malignancies.
Press O.W. et al. *J. Clin. Oncol*. 7(8): 1027-38, 1989. Treatment of refractory non-Hodgkin's lymphoma with radiolabeled MB-1 (anti-CD37) antibody.
Press O.W. et al. *Lancet* 346(8971): 336-40, 1995. Phase II trial of $^{131}$I-B1 (anti-CD20) antibody therapy with autologous stem cell transplantation for relapsed B cell lymphomas.
Press O.W. et al. *Proc. Amer. Soc. Clin. Oncol*. 17, abst. No. 9, May 1998. A phase I/II trial of high dose iodine-131-anti-B1 (anti-CD20) monoclonal antibody, etoposide, cyclophosphamide, and autologous stem cell transplantation for patients with relapsed B cell lymphomas.
Press O.W. et al. *Proc. Amer. Soc. Clin. Oncol*. 5: 221, abst. No. 864, 1986. Serotherapy of malignant B cell lymphomas with monoclonal antibody 1F5 (anti-CD20).
Press O.W. et al., "Radiolabeled-antibody therapy of B-cell lymphoma with autologous bone marrow support", N Engl J Med., Oct. 1993, vol. 329, No. 17, pp. 1219-1224.
Public Hearing Transcript, Biological Response Modifiers Advisory Committee, Center for Biological Evaluation and Research, Depart-

(56) References Cited

OTHER PUBLICATIONS ment of Health and Human Services—Food and Drug Administration, nineteenth meeting Jul. 25, 1997, pp. 1-201.
Rai K.R. et al. (in) R. Hoffman, R., ed., *Hematology*, 2d. ed., Churchill Livingstone, 1995, Chapter 83, pp. 1308-1319. Chronic lymphocytic leukemia.
Rapoport et al., "Autotransplantation for advanced lymphoma and Hodgkin's disease followed by post-transplant rituxan/GM-CSF or radiotherapy and consolidation chemotherapy," *Bone Marrow Transplant*. 29(4): 303-12 (2002).
Rastetter et al., "Rituximab: expanding role in therapy for lymphomas and autoimmune diseases," Annu. Rev. Med., 55: 477-503 (2004).
Ravaud et al., "Adjuvant Bacillus Calmette-Guerin Therapy in Non-Hodgkin's Malignant Lymphomas: Long-Term Results of a Randomized Trial in a Single Institution", J. Clinical Oncology, 1990, vol. 8, pp. 608-614.
Reff M. et al., "Depletion of B cells in vivo by a chimeric mouse human monoclonal antibody to CD20.", J. Cell. Biochem., 1993, Suppl. 17E: p. 260, abst. No. T103.
Reff M.E. et al. *Blood* 83(2): 435-45, 1994. Depletion of B cells in vivo by a chimeric mouse human monoclonal antibody to CD20.
Reilly R.M. *Clin. Pharm*. 10: 359-75, 1991. Radioimmunotherapy of malignancies.
Rituxan® (Rituximab) Draft Labeling Text, U.S. BL 103705/5230 Amendment: RITUXXAN®(Rituximab)—Genentech, Inc. Sep. 29, 2006, pp. 1-46.
Rituxan® (Rituximab) Labeling Text, U.S. BL 103705 Supplemental Amendment: Rituxan Rheumatoid Arthritis—Genentech , Inc. Feb. 2006, pp. 1-53.
RITUXAN® Rituximab Prescribing Information, Initial US Approval: Nov. 1997; Med Guide Revision Date: Jul. 2012; Prescribing Information Revision Date: Oct. 2012; pp. 1-40.
Ritz Jet al., "Serotherapy of acute lymphoblastic leukemia with monoclonal antibody." Blood, 1981, vol. 58, pp. 141-152.
Robertson M.J. et al. *Blood* 79(9): 2229-36, 1992. Human bone marrow depleted of CD33- positive cells mediates delayed but durable reconstitution of hematopoiesis: Clinical trial of MY9 monoclonal antibody-purged autgrafts for the treatment of acute myeloid leukemia.
Robinson R. et al. *Human Antibody Hybrid* 2: 84-93, 1991. Chimeric mouse-human anti-carcinoma antibodies that mediate different anti-tumor cell biological activities.
Roche press release, Investor Update, Basel, Jun. 7, 2004, "MabThera/Rituxan® maintenance therapy dramatically improves progression-free survival in patients with indolent Non-Hodgkin's Lymphoma (NHL)", http://www.roche.com/investors//r_update/inv-update-2004-06-07d.html; pp. 1-3 (Retrieved Jan. 30, 2013).
Rogers, J., et al., "Analysis of bcl-2 t(14;18) translocation in relapsed B-cell lymphoma patients treated with the chimeric anti-CD20 antibody IDEC-C2B8.", Proc Annu Meet Am Assoc Cancer Res 37:213 (#1456), Mar. 1996.
Rogers, J., et al., "Clearance of bcl-2 (t14;18) from peripheral blood (PB) and bone marrow (BM) in patients (PTS) with relapsed low-grade or follicular (IWF:A-D) lymphoma (NHL) following single-agent therapy with the chimeric anti-CD20 antibody (MAB) IDEC-C2B8.", Ann Oncol 7(3 Suppl):34 (#108), Jun. 1996.
Rohatiner et. al., "Follicular Lymphoma", The Non-Hodgkin's Lymphomas, 2$^{rd}$ edition, Ch. 41, Ian T. MaGrath, Arnold, 1997, pp. 867-895.
Rohatiner et. al., "Meta-Analysis to Evaluate the Role of Interferon in Follicular Lymphoma," J. Clinical Oncology, Apr. 2005, vol. 23, No. 10, pp. 2215-2223.
Rosenberg J., "Pharmacokinetics (PK) of the chimeric anti-CD20 antibody (MAB) IDEC-C2B8: Analysis of serum concentrations in patients (PTS) with relapsed B-cell lymphoma." Br J Haematol 93 (2 Suppl):283 (#1071), May 1996.

Rosenberg, J. et al., "Pharmacokinetic analysis of serum concentrations of the chimeric anti-CD20 antibody IDEC-C2B8 in patients with relapsed B-cell lymphoma." Proc Am Soc Clin Oncol 15:418 (#1282), May 1996.
Rottenburger C. et al. *Br. I Haematol*. 106(2): 545-52, 1999. Clonotypic CD20+ and CD19+ B cells in peripheral blood of patients with multiple myeloma post high-dose therapy and peripheral blood stem cell transplantation.
Rudikoff S. et al. *Proc. Nat'l. Acad.Sci*. 79: 1979-83, 1982. Single amino acid substitution altering antigen-binding specificity.
Sahagan B.G. et al. *J. Immunol*. 137: 1066-74, 1986. A genetically engineered murine/human chimeric antibody retains specificity for human tumor-associated antigen.
Saville, M.W. ,Statement of M. Wayne Saville, M.D., dated Dec. 20, 2007, submitted by applicant in Taiwan (R.O.C.) patent application No. 088119557 (Treatment of hematologic malignancies associated with circulating tumor cells using chimeric anti-CD20 antibody, Grillo-Lopez et al., filed Nov. 9, 1999) pp. 1-3.
Scharff M. *Harvey Lectures* 69: 125-42, 1974. The synthesis, assembly, and secretion of immunoglobulin: a biochemical and genetic approach.
Schein et. al., "Non-Hodgkin's Lymphoma: Patterns of Relapse from Complete Remission After Combination Chemotherapy", Cancer, 1975, vol. 35, pp. 354-357.
Schlom J. et al. *J. Natl. Cancer Inst*. 82(9): 763-71, 1990. Advantage of dose fractionation in monoclonal antibody-targeted radioimmunotherapy.
Schwartz-Albiez R. et al. *J. Immunol*. 140(3): 905-14, 1988. The B cell-associated CD37 antigen (gp40-52). Structure and subcellular expression of an extensively glycosylated glycoprotein.
Seaver S. *Gen. Engr. News*. 19 and 21, 1982. Monoclonal antibodies in industry: more difficult than originally thought.
See-Lasley K. et al. *Manual of Oncology Therapeutics*, St. Louis: C.V. Mosby Co., pp. 44-71, 1981. Hodgkin's disease and non-Hodgkin's lymphoma.
Senter P.D. et al. *Adv. Exp. Med Biol*. 303: 97-105, 1991. Activation of prodrugs by antibody-enzyme conjugates.
Senter P.D. et al. *Cancer Res*. 49: 5789-92, 1989 Enhancement of the in vitro and in vivo antitumor activities of phosphorylated mitomycin C and etoposide derivatives by monoclonal antibody-alkaline phosphatase conjugates.
Senter P.D. *FASEB I* 4: 188-93, 1990. Activation of prodrugs by antibody-enzyme conjugates: a new approach to cancer therapy.
Shan D. et al. *Clin. Cancer Res*. 7(8): 2490-95, 2001. Synergistic effects of the fenretinide (4-HPR) and anti-CD20 monoclonal antibodies on apoptosis induction of malignant human B cells.
Sharkey R.M. et al. *Cancer Res*. 50(3): 964s-969s, 1990. Biological considerations for radioimmunotherapy.
Shipp et al. "The International Non-Hodgkin's Lymphoma Prognostic Factors Project: A predictive model for aggressive non-Hodgkin's lymphoma", N Engl J Med., Sep. 1993, vol. 329, No. 14, pp. 987-994.
Shulman M. et al. *Nature* 276(5685): 269-70, 1978. A better cell line for making hybridomas secreting specific antibodies.
Siddhartha, G. and Vijay, P., "R-CHOP versus R-CVP in the treatment of follicular lymphoma: a meta-analysis and critical appraisal of current literature". *J. Hematology & Oncology* 2:14, pp. 1-7 (Mar. 24, 2009) doi: 10.1186/1756-8722-2-14.
Smalley R.V. et al., "Interferon alfa combined with cytotoxic chemotherapy for patients with non-Hodgkin's lymphoma", N Engl J Med., Nov. 1992, vol. 327, No. 19, pp. 1336-1341.
Smeland E.B. et al., "Activation of human B cells: alternate options for initial triggering and effects of nonmitogenic concentrations of anti-IgM antibodies on resting and activated cells", J Immunol., May 1987, vol. 138, No. 10, pp. 3179-3184.
Soiffer R.J. et al. *Blood* 79(2): 517-26, 1992. Clinical and immunologic effects of prolonged infusion of low-dose recombinant interleukin-2 after autologous and T-cell depleted allogeneic bone marrow transplantation.
Soiffer R.J. et al. *Blood* 84(3): 964-971, 1994. Effect of low-dose interleukin-2 on disease relapse after T-cell-depleted allogeneic bone marrow transplantation.

(56) References Cited

OTHER PUBLICATIONS

Solal-Celigny P. et al., "Doxorubicin-containing regimen with or without interferon alfa-2b for advanced follicular lymphomas: final analysis of survival and toxicity in the Groupe d'Etude des Lymphomes Folliculaires 86 Trial", J Clin Oncol., Jul. 1998, vol. 16, No. 7, pp. 2332-2338.

Sonneveld, et. al., "Comparison of Doxorubicin and Mitoxantrone in the Treatment of Elderly Patients with Advanced Diffuse Non-Hodgkin's Lymphoma Using CHOP Versus CNOP Chemotherapy", Journal of Clinical Oncology, Oct. 1995, vol. 13, No. 10, pp. 2530-2539.

Srivastava S.C. et al. *Nucl. Med. Biol.* (*Li Rad. Appl. Instrum. B*) 18(6): 589-603, 1991. Progress in research on ligands, nuclides and techniques for labeling monoclonal antibodies.

Stashenko P. et al., "Characterization of Human B Lymphocyte-Specific Antigen", J Immunol., Oct. 1980, vol. 125, No. 4 pp. 1678-1685.

Staudt L.M. et al. Manuscript from pubmedcentral at NIH, edited paper published at *Adv. Immunol.* 87: 163-208, 2005. The biology of human lymphoid malignancies revealed by gene expression profiling.

Stenbygaard L.E. et al. *Breast Cancer Res. Treatment* 25: 57-63, 1993. Toremifene and tamoxifen in advanced breast cancer—a double-blind cross-over trial.

Steward et al. "Maintenance Chlorambucil After CVP in the Management of Advanced Stage, Low-Grade Histologic Type Non-Hodgkin's Lymphoma" Cancer 61(3) 1988, pp. 441-447.

Stewart J.S.W. et al. *Int. J. Cancer* Suppl. 3: 71-76, 1988. Intraperitoneal $^{131}$I- and $^{90}$Y-labelled monoclonal antibodies for ovarian cancer: pharmacokinetics and normal tissue dosimetry.

Sun L.K. et al. *Hybridoma* 5(Suppl. 1): S17-20, 1986. Chimeric antibodies with 17-1A-derived variable and human constant regions.

Sweetenham et al., "Cost-minimization analysis of CHOP, fludarabine and rituximab for the treatment of relapsed indolent B-cell non-Hodgkin's lymphoma in the U.K.", *British Journal of Haematology* 106, 1999, pp. 47-54.

Tan L.K. et al. *J. Immunol.* 135: 3564-67, 1985. A human-mouse chimeric immunoglobulin gene with a human variable region is expressed in mouse myeloma cells.

Tedder T.F. et al. *Eur J Immunol.* 16(8): 881-87, 1986. Antibodies reactive with the B1 molecule inhibit cell cycle progression but not activation of human B lymphocytes.

Tedder T.F. et al. *J Immunol.* 141(12): 4388-94, 1988. Cloning of a complementary Dna encoding a new mouse B lymphocyte differentiation antigen, homologous to the human B1 (CD20) antigen, and localization of the gene to chromosome 19.

Tedder T.F. et al. *J Immunol.* 135(2): 973-79, 1985. The B cell surface molecule B1 is functionally linked with B cell activation and differentiation.

Tedder TF et al., "CD20: A regulator of cell-cycle progression of B lymphocytes." Immunol Today, 1994, vol. 15, pp. 450-454.

Teeling J.L. et al. *Blood* 104: 1793-1800, 2004. Characterization of new human CD20 monoclonal antibodies with potent cytolytic activity against non-Hodgkin lymphomas.

Teeling J.L. et al. *J Immunol.* 277: 362-71, 2006. The biological activity of human CD20 monoclonal antibodies is linked to unique epitopes on CD20.

Thompson Reuters Pharma™ "Drug Report: Rituximab", http://thomsonpharma.com; Update date: Mar. 28, 2011; pp. 1-4 (Retrieved 2011).

Tobinai K. et al. *Ann. Oncol.* 9(5): 527-34, 1998. Feasibility and pharmacokinetic study of a chimeric anti-CD20 monoclonal antibody (IDEC-C2B8, rituximab) in relapsed B-cell lymphoma. The IDEC-C2B8 Study Group.

Treon et al., "Interferon-Gamma Induces CD20 Expression on Multiple Myeloma Cells via Induction of Pu.1 and Augments Rituximab Binding to Myeloma Cells," Oncology 14(31): Abstract #521 (2000).

Tsai D.E. et al. *Blood* 92(10 Suppl. 1): 415a, abst. No. 1713, Nov. 1998. Progressive intermediate grade non-Hodgkin's lymphoma after high dose therapy and autologous peripheral stem cell transplantation (PSCT) has a high response rate to rituximab.

Tsai D.E. et al. *Bone Marrow Transplant.* 24(5): 521-26, 1999. Rituximab (anti-CD20 monoclonal antibody) therapy for progressive intermediate-grade non-Hodgkin's lymphoma after high-dose therapy and autologous peripheral stem cell transplantation.

Tsai D.E. et al. *Clin. Lymphoma Myeloma* 1(1): 62-66, 2000. Progressive intermediate-grade non-Hodgkin's lymphoma after high-dose therapy and autologous peripheral stem-cell transplantation: changing the natural history with monoclonal antibody therapy.

Uckun F.M. et al. *Cancer Res.* 45(1): 69-75, 1985. Increased efficiency in selective elimination of leukemia cells by a combination of a stable derivative of cyclophosphamide and a human B-cell-specific immunotoxin containing pokeweed antiviral protein.

Uckun F.M. et al., "Combined ex vivo treatment with immunotoxins and mafosfamid: a novel immunochemotherapeutic approach for elimination of neoplastic T cells from autologous marrow grafts", J Immunol., May 1985, vol. 134, No. 5, pp. 3504-3515.

United States Department of Health and Human Services, Food and Drug Administration, "Guidance for Industry: Distributing Scientific and Medical Publications on Unapproved New Uses—Recommended Practices", Revised Draft Guidance, Feb. 2014, pp. 1-17.

Unterhalt et al., "Significant Prolongation of Disease Free Survival in Advanced Low Grade Non-Hodgkin's Lymphomas (NHL) by Interferon Alpha Maintenance: International Conference on Malignant Lymphoma, Jun. 5-8, 1996, Lugano, Switzerland", Annals of Oncology, 1996, vol. 7, Supplement 3, p. 229.

Unterhalt, et. al., "Long Term Interferon Alpha Maintenance Prolongs Remission Duration in Advanced Low Grade Lymphomas and is Related to the Efficacy of Initial Cytoreductive Chemotherapy", Blood, Nov. 1996, vol. 88, No. 10, Suppl. 1, Abstract 1801, pp. 453a.

Urlaub G. et al. *Som. Cell. Mol Genet.* 12(6): 555-66, 1986. Effect of gamma rays at the dihydrofolate reductase locus: deletions and inversions.

Valentine M.A. et al., "Phosphorylation of the CD20 phosphoprotein in resting B lymphocytes. Regulation by protein kinase C", J Biol Chem., Jul. 1989, vol. 264, No. 19, pp. 11282-11287.

Van Der Kolk et al., "Chimeric Anti-CD20 Monoclonal Antibody (Rituximab) Plus G-CSF in Relapsed B-Cell Lymphoma: A Phase I/II Clinical Trial", British Journal of Haematology, Jul. 1998, vol. 102, No. 1, p. 243.

Van der Kolk L.E. et al. *Blood* 92(10 Suppl. 1): 241b, abst. No. 4037, Nov. 1998. Chimeric anti-CD20 monoclonal antibody (rituximab) plus G-CSF in relapsed B-cell lymphoma: a phase I/II clinical trial.

Van der Kolk L.E. et al. *Blood* 92(10 Suppl. 1): 512a-513a, abst. No. 2284, 1997. Phase I/II clinical trial to evaluate the safety and efficacy of a chimeric anti-CD20 monoclonal antibody (rituximab) and G-CSF given weekly to patients with relapsed B-cell lymphoma.

Van Oers et al., "Rituximab maintenance improves clinical outcome of relapsed/resistant follicular non-Hodgkin lymphoma in patients both with and without rituximab during induction: results of a prospective randomized phase 3 intergroup trial", Blood, 2006, vol. 108, pp. 3295-3301.

Vartholomatos G. et al. *Acta Haematol.* 102: 94-98, 1999. Rituximab (anti-CD20 monoclonal antibody) administration in a young patient with resistant B-prolymphocytic leukemia.

Venugopal P. et al. *Blood* 92(10 Suppl. 1): 247a, abst. No. 1009, Nov. 1998. Upregulation of CD20 expression in chronic lymphocytic leukemia (CLL) cells by in vitro exposure to cytokines.

Verkh L.I. et al. *Proc. Amer. Soc. Clin. Oncol.* 17: abst. No. 154, 1998. Dosimetry results of ONCOLYM™ in the treatment of refractory B cell non-Hodgkin's lymphoma (NHL).

Vey N. et al. *Leuk. Lymphoma* 221(1-2): 107-14, 1996. A pilot study of autologous bone marrow transplantation followed by recombinant interleukin-2 in malignant lymphomas.

Vose et. al., "Diagnosis and Treatment of Non-Hodgkin's Lymphoma of Adults", Neoplastic Diseases of the Blood, $3^{rd}$ edition, Ch. 44, Wiernik, Canellos, Dutcher, & Kyle, Churchill Livingstone, 1996, pp. 907-924.

(56) References Cited

OTHER PUBLICATIONS

Vose J.M. et al. *J Clin. Oncol.* 19(2): 389-97, 2001. Phase II study of rituximab in combination with chop chemotherapy in patients with previously untreated, aggressive non-Hodgkin's lymphoma.
Vose, et. al., "Long-term update of a phase II study of rituximab in combination with previously untreated, aggressive non-Hodgkin's lymphoma", Leukemia & Lymphoma, Nov. 2005, vol. 46, No. 11, pp. 1569-1573.
Voso et al., "In vivo depletion of B cells using a combination of high-dose cytosine arabinoside/mitoxantrone and rituximab for autografting in patients with non-Hodgkin's lymphoma," *Br. J Haematol* 109(4): 729-35 (2000).
Wadler S. et al. *Semin. Oncol.* 19(2 Suppl. 3): 45-48, 1992. Principles in the biomodulation of cytotoxic drugs by interferons.
Wahl R.L. et al. *J Nucl. Med.* 31(5): 852, abst. No. 622, 1990. Radioimmunotherapy of B-cell lymphoma with 1131 MB-1 monoclonal antibody.
Wahl R.L. et al. *Proc. Amer. Soc. Clin. Oncol.* 17: 40a, abst. No. 156, May 1998. Successful retreatment of non-Hodgkin's lymphoma (NHL) with iodine-131 anti-BI antibody.
Weisdorf, Daniel et al., "Survival After Relapse of Low-Grade Non-Hodgkin's Lymphoma: Implications for Marrow Transplantation"; *J. Clin Oncol* 1992; 10(6): pp. 942-947.
Welte K. et al. *Blood* 64: 380-85, 1984. Defective interleukin 2 production in patients after bone marrow transplantation and in vitro restoration of defective T lymphocyte proliferation by highly purified interleukin 2.
Wessels B.W. et al. *Med. Phys.* 11(5): 638-45, 1984. Radionuclide selection and model absorbed dose calculations for radiolabeled tumor associated antibodies.
White C.A. et al. *Ann. Oncol.* 10(3 Suppl): 64, abst. No. 215, 1999. Radioimmunotherapy of relapsed • or refractory non-Hodgkin's lymphoma (NHL): IDEC-Y2B8 phase I/II $^{90}$yttnum trial.
White C.A. et al. *Ann. Rev. Med.* 52: 125-45, 2001. Antibody-targeted immunotherapy for treatment of malignancy.
White C.A. et al. *Blood* 87(9): 3640-49, 1996. Radioimmunotherapy of relapsed B-cell lymphoma with Yttrium 90 anti-idiotype monoclonal antibodies.
White C.A. et al. *Eur. J. Cancer* 35: S57, abst. No. 107, 1999. Zevalin™ radioimmunotherapy of relapsed or refractory non-Hodgkin's lymphoma.
White C.A. et al., "Anti-CD20 Monoclonal Antibodies as Novel Treatments for Non-Hodgkin's Hodgkin's Lymphoma." Pharm. Sci. Tech. Today 2(3): 95-101 (Mar. 1999).
White CA, et al., "Idec-C2b8-Induced B Cell Depletion Is Not Associated With Significant Immune Suppression or Infection." Eur. J. Cancer, Sep. 1997, vol. 33, Suppl. 8, Abstract 1203, p. S266.
White, C.A. et al., "Anti-CD20 antibody (MAB) IDEC-C2B8 in relapsed low-grade/follicular (LG/F) B-cell non-Hodgkin's lymphoma (NHL). Expanded efficacy and safety results.", J Immunother 19(6):458, Nov. 1996.
White, C.A. et al., "IDEC-C2B8: Improved tolerance correlated with pharmacodynamic effects in patients with B-cell NHL.", Proc Annu Meet Am Assoc Cancer Res 36:638 (#3799), Mar. 1995.
White, C.A. et al., "Review of single agent IDEC-C2B8 safety and efficacy results in low-grade or follicular non-Hodgkin's lymphoma.", Eur J Cancer, Jun. 1997, vol. 33, Suppl. 5, Abstract #91, p. S40.
White, Cancer Biother Radiopharm. Aug. 1999;14(4): pp. 241-50, "Rituximab immunotherapy for non-Hodgkin's lymphoma."
Winkler U. et al. *Blood* 92(10 Suppl. 1): 285b, abst. No. 4228, Nov. 1998. Severe side effects in patients with B-cell chronic lymphocytic leukemia (CLL) and lymphocytosis treated with the monoclonal anti-CD20 antibody rituximab.
Winkler U. et al. *Blood* 94: 2217-24, 1999. Cytokine-release syndrome in patients with B-cell chronic lymphocytic leukemia and high lymphocyte counts after treatment with an antiCD20 monoclonal antibody (rituximab, IDEC-C2B8).

Wiseman G. et al. *Blood* 92(10 Suppl. 1): 417a, abst. No. 1721, Nov. 1998. IDEC-Y2B8 radioimmunotherapy: baseline bone marrow involvement and platelet count are better predictors of hematologic toxicity than dosimetry.
Wiseman G. et al. Cancer Biother. Radiopharm. 13(1): 59, abst. No. 22, 1998. Radioimmunotherapy of relapsed non-Hodgkin's lymphoma (NHL) with IDEC-Y2B8 90yttrium anti-CD20 monoclonal antibody.
Wiseman G. et al. *Cancer Biother. Radiopharm.* 13(4): 317, abst. No. 51, 1998. IDECY2B8 radioimmunotherapy of relapsed non-Hodgkin's lymphoma (NHL): interim analysis.
Wiseman G. et al. *Cancer Biother. Radiopharm.* 14(4): 315, abst. No. 2, 1999. 90Yttrium labelled Idec Y2B8 anti-CD20 radioimmunotherapy.
Wiseman G. et al. *Proc. Amer. Soc. Clin. Oncol.* 17, 1998. Radioimmunotherapy of relapsed non-Hodgkin's lymphoma (NHL) with IDEC-Y2B8 $^{90}$yttrium radioimmunotherapy.
Wiseman G. et al., "Radioimmunotherapy of relapsed or refractory non-Hodgkin's Lymphoma (NHL) with IDEC-Y2B8.", I.J Rad. Oncol. Biol. Phys., 1999, vol. 45, Suppl., 10, p. 390, abst. No. 260.
Wiseman G.A. et al. *Blood* 92(10 Suppl. 1): 510a, abst. No. 2273, Nov. 1998. IDEC-Y2B8 ($^{90}$Y conjugated anti-CD20) dosimetry calculated from $^{111}$In anti-CD20 in patients with low and intermediate grade B-cell non-Hodgkin's lymphoma (NHL) emphasis on bone marrow (BM).
Wiseman G.A. et al. *Blood* 94(10 Suppl. 1): 92a, abst. No. 403, 1999. ZEVALIN™ biodistribution and dosimetry estimated normal organ absorbed radiation doses are not affected by prior therapy with rituximab.
Wiseman G.A. et al. *Clin. Cancer Res.* 5(Suppl.): 3281s-3286s, 1999. Radioimmunotherapy of relapsed non-Hodgkin's lymphoma with Zevalin, a 90Y-labeled anti-CD20 monoclonal antibody.
Wiseman G.A. et al. *I.J. Oncol. Biol. Phys.* 42(1 Suppl .): 130, abst. No. 11, 1998. IDECY2B8 ($^{90}$yftrium ibritumomab tiuxetan) radioimmunotherapy safety results in relapsed or chemotherapy refractory non-Hodgkin's lymphoma patients treated at reduced doses because of pre-existing thrombocytopenia.
Wiseman G.A. et al. I.J. Oncol. Biol. Phys. 45(3 Suppl .): 390, abst. No. 2217, 1999. IDECY2B8 (90yttrium(90yttriumibritumomab tiuxetan) radioimmunotherapy safety results in relapsed or chemotherapy refractory non-Hodgkin's lymphoma patients treated at reduced doses because of preexisting thrombocytopenia.
Wiseman G.A. et al. *J Nucl. Med.* 38(5 Suppl.): 251, abst. No. 1062, 1997. Y-90 anti-CD20 monoclonal antibody (IDEC-Y2B8) dosimetry calculated from In-111 anti-CD20 in patients with low and intermediate grade B-cell non-Hodgkin's lymphoma.
Wiseman G.A. et al. *J Nucl. Med.* 39(5 Suppl.): 185P, abst. No. 836, 1998. Whole-body gamma camera image quantification from multiple camera types for radioisotope therapy dosimetry.
Wiseman G.A. et al. *Proc. Amer. Soc. Clin. Oncol.* 18: 4a, abst. No. 13, 1999. Therapeutic index of IDEC-Y2B8 radioimmunotherapy: up to 850 fold greater radiation dose to tumor than normal organs.
Wiseman G.A. et al., "Non-Hodgkin's lymphoma tumor and bone marrow radiation doses from radioimmunotherapy with IDECY2B8 yttrium-90 anti-CD20 monoclonal antibody.", J Nucl Med. 1998, vol. 39, Suppl. 5, p. 69P, abst. No. 267.
Wiseman G.A. et al.. "Final dosimetry results of IDEC-Y2B8 phase I/II 90yttrium radioimmunotherapy trial in non-Hodgkin's lymphoma (NHL).", J Nucl Med., 1999, vol. 40, Suppl. 1, p. 64P, abst. No. 260.
Witherspoon R.P. et al. *Semin. Hematol.* 21(1): 2-10, 1984. Immunologic reconstitution after human marrow grafting.
Witzig T. et al. *Blood* 90(10 Suppl. 1): 586a, abst. No. 2606, 1997. IDEC-Y2B8 $^{90}$yttrium anti-CD20 radioimmunotherapy of relapsed non-Hodgkin's lymphoma (NHL): interim results of a phase I/II trial.
Witzig T. et al. *Blood* 92(10 Suppl. 1): 417a, abst. No. 1722, Nov. 1998. IDEC-Y2B8 radioimmunotherapy: responses in patients with splenomegaly.
Witzig T.E. et al. *Am. J. Clin. Pathol.* 101: 312-17, 1994. Measurement of the intensity of cell surface antigen expression in B-cell chronic lymphocytic leukemia.

(56) References Cited

OTHER PUBLICATIONS

Witzig T.E. et al. *Blood* 94(10 Suppl. 1): 631a, abst. No. 2805, 1999. Prospective randomized controlled study of ZEVALIN™ (IDEC-Y2B8) radioimmunotherapy compared to rituximab immunotherapy for B-cell NHL: report of interim results.
Witzig T.E. et al. *Blood* 94(10 Suppl. 1): 92a, abst. No. 400, 1999. Reduced-dose ZEVALIN™ radioimmunotherapy for relapsed or refractory B-cell non-Hodgkin's lymphoma (NHL) patients with pre-existing thrombocytopenia: report of interim results of a phase II trial.
Witzig T.E. et al. *I Clin. Oncol.* 17(12): 3793-3803, 1999. Phase I/II trial of IDEC-Y2B8 radioimmunotherapy for treatment of relapsed or refractory CD20(+) B-cell non-Hodgkin's lymphoma.
Witzig T.E. et al. *I Immunother.* 21(6): 463, abst. No. 2805, 1998. IDEC-Y2B8 radioimmunotherapy of relapsed or refractory non-Hodgkin's lymphoma.
Witzig T.E. et al. *J. Clin. Oncol.* 20(15): 3262-69, 2002. Treatment with ibritumomab tiuxetan radioimmunotherapy in patients with rituximab-refractory follicular non-Hodgkin's lymphoma.
Witzig T.E. et al. *J. Clin. Oncol.* 20: 2453-63, 2002. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.
Witzig T.E. et al. *Proc. Amer. Soc. Clin. Oncol.* 18: 41a, abst. No. 152, 1999. Commonly used response criteria for non-Hodgkin's lymphoma (NHL) applied to IDEC-Y2B8 radioimmunotherapy trial: importance of "normal" lymph node size.
Yakoub-Agha et al., "Allogeneic bone marrow transplantation in patients with follicular lymphoma: a single center study," *Bone Marrow Transplant* 30(4): 229-34 (2002).
Yang H. et al. *Am. J. Hematol.* 62: 247-50, 1999. Tumor lysis syndrome occurring after the administration of rituximab in lymphoproliferative disorders: high-grade non-Hodgkin's lymphoma and chronic lymphocytic leukemia.
Yokota S. et al. *Cancer Res.* 50: 32-37, 1990. Synergistic potentiation of in vivo antitumor activity of anti-human T-leukemia immunotoxins by recombinant a-interferon and daunorubicin.
Zhou L-J et al., "CD20 Workshop Panel Report" in Schlossman SF. Boumsell L., Gilks W., et al. (eds): *Leucocyte Typing V* (White Cell Differentiation Antigens. Proceedings of the Fifth International Workshop and Conference Held in Boston, USA Nov. 3-7, 1993) Oxford, United Kingdom, Oxford University, 1995, vol. 1, pp. 511-514.
Zhou X. et al., "Application of cytokine therapy in tumor treatment", Chinese Pharm. J., 1995, vol. 30, No. 8, pp. 453-54 (English translation of abstract provided).
Zinzani, et. al., "Elderly Aggressive-Histology Non-Hodgkin's Lymphoma: First-Line VNCOP-B Regimen Experience on 350 patients", Blood, Jul. 1999, Vo. 93, No. pp. 33-38.
Grillo-Lopez, et. al., presentation titled "IDEC-C2B8 Rituxan (rituximab)" presented at Biological Response Modifiers Committee Review in Bethesda, Maryland on Jul. 25, 1997 (77 pages).
McLaughlin, Peter, presentation titled "IDEC-C2B8 Anti-CD20 Antibody: Final Report on a Phase III Pivotal Trial in Patients (PTS) With Relapsed Low-Grade or Follicular Lymphoma (LG/F NHL)" presented at the 38th Annual Meeting of The American Society of Hematology in Orlando, Florida on Dec. 6-10, 1996 (21 pages).
McLaughlin, Peter, presentation titled "Pharmacokinetics (PK) and Pharmacodynamics (PD) of the Anti-CD20 Antibody (MAB) IDEC-C288 in Patients (PTS) With Relapsed Low-Grade or Follicular Lymphoma (LG/F NHL)" presented at the 38th Annual Meeting of the American Society of Hematology in Orlando, Florida on Dec. 6-10, 1996 (21 pages).
Czuczman, Myron, presentation titled "IDEC-C2B8/CHOP Chemoimmunotherapy in Patients With Low-Grade Lymphoma: Clinical and BCL-2 (PCR) Final Results" presented by Dr. Myron Czuczman at the 38th Annual Meeting of the American Society of Hematology in Orlando, Florida on Dec. 6-10, 1996 (15 pages).

"Treatment of intermediate or high-grade malignant NHL," ed. Junliang Ma, *Modern Oncology Manual*, $1^{st}$ ed., Liaoning Science and Technology Press, Jan. 1996, p. 343 (partial English translation included).
Bishop, et al, "A randomized Trial of High Dose Cyclophosphamide, Vincristine ,and Prednisone Plus or Minus Doxorubicin (CVP Versus CAVP) With Long-Term Follow-Up in Advanced Non-Hodgkin's Lymphoma," Leukemia 1987, vol. 1, No. 6, pp. 508-513.
cancer.net, "Understanding Maintenance Therapy," approved Aug. 2015, http://www.cancer.net/navigating-cancer-care/how-cancer-treated/understanding-maintenance-therapy retrieved Jul. 21, 2017 (3 pages).
Canellos et al., "Chemotherapy of the Non-Hodgkin's Lymphomas," Cancer 1987, vol. 42, No. 2, pp. 932-940.
Chen, et al., "Synergistic Anti-proliferative Effect of Metformin and Sorafenib on Growth of Anaplastic Thyroid Cancer Cells and their Stem Cells," Oncology Reports 2014, vol. 33, pp. 1994-2000.
Chinn, et al., "A Y-labeled anti-CD20 monoclonal antibody conjugated to MX-DTPA, a high-affinity chelator for yttrium," Proc. Am. Assn. Cancer Res. 1999, 40: 574, abst. No. 3786 (1 page).
Coiffier et al., "A multicenter, randomized phase II study of rituximab (chimeric anti-CD20 mAb) at two dosages in patients with relapsed or refractory intermediate or high-grade Nhl (IHG-NHL) or in elderly patients in first-line therapy," Blood Nov. 15, 1997, vol. 90, No. 10, pp. 510a, Abstract 2271.
Czuczman et al., "Prolonged Clinical and Molecular Remission in Patients With Low-Grade or Follicular Non-Hodgkin's Lymphoma Treated With Rituximab Plus CHOP Chemotherapy: 9-Year Follow-Up," J. Clin. Oncol. 2004, vol. 22, No. 23, pp. 4711-4716.
Declaration of Dr. Izidore Lossos, dated Mar. 15, 2017 (63 pages) in *Inter Partes Review* No. IPR2017-01093 re: U.S. Pat. No. 8,329,172, Grillo-Lopez, "Combination Therapies for B-Cell Lymphomas Comprising Administration of Anti-CD20 Antibody".
Declaration of Dr. Izidore Lossos, dated Mar. 15, 2017 (62 pages) in *Inter Partes Review* No. IPR2017-01094 re: U.S. Pat. No. 8,557,244, White, et al., "Treatment of Aggressive Non-Hodgkin's Lymphoma with Anti-CD20 Antibody".
Declaration of Dr. Izidore Lossos, dated Mar. 15, 2018 (82 pages) in *Inter Partes Review* No. IPR2017-01095 re: U.S. Pat. No. 9,296,821, Grillo-Lopez, "Combination Therapies for B-Cell Lymphomas Comprising Administration of Anti-CD20 Antibodies".
Declaration of Dr. Walter Longo, dated Mar. 3, 2017 (17 pages) in *Inter Partes Review* No. IPR2017-01093 re: U.S. Pat. No. 8,329,172, Grillo-Lopez, "Combination Therapies for B-Cell Lymphomas Comprising Administration of Anti-CD20 Antibody".
Declaration of Dr. Walter Longo, dated Mar. 3, 2017 (22 pages) in *Inter Partes Review* No. IPR2017-01094 re: U.S. Pat. No. 8,557,244, White, et al., "Treatment of Aggressive Non-Hodgkin's Lymphoma with Anti-CD20 Antibody".
Declaration of Dr. Walter Longo, dated Mar. 3, 2017 (22 pages) in *Inter Partes Review* No. IPR2017-01095 re: U.S. Pat. No. 9,296,821, Grillo-Lopez, "Combination Therapies for B-Cell Lymphomas Comprising Administration of Anti-CD20 Antibodies".
Declaration of Howard Ozer, M.D., Ph.D., dated Apr. 3, 2017 (103 pages) in *Inter Partes Review* No. IPR2017-01166 re: U.S. Pat. No. 8,329,172, Grillo-Lopez, "Combination Therapies for B-Cell Lymphomas Comprising Administration of Anti-CD20 Antibody".
Declaration of Howard Ozer, M.D., Ph.D., dated Apr. 25, 2017 (91 pages) in *Inter Partes Review* No. IPR2017-01167 re: U.S. Pat. No. 8,577,244, White, et al., "Treatment of Aggressive Non-Hodgkin's Lymphoma with Anti-CD20 Antibody".
Declaration of Howard Ozer, M.D., Ph.D., dated Apr. 28, 2017 (95 pages) in *Inter Partes Review* No. IPR2017-01168 re: U.S. Pat. No. 8,821,873, White, et al., "Treatment of Diffuse Large Cell Lymphoma with Anti-CD20 Antibody".
Declaration of Mark "Kip" Benyunes, dated Jun. 2, 2011 (7 pages) in *Inter Partes Review* No. IPR2016-01166 re: U.S. Pat. No. 8,329,172, Grillo-Lopez, "Combination Therapies for B-Cell Lymphomas Comprising Administration of Anti-CD20 Antibody".
Declaration of Scott Bennett, Ph.D., dated Apr. 6, 2017 (70 pages) in *Inter Panes Review* No. IPR2017-01166 re: U.S. Pat. No. 8,329,172, Grillo-Lopez, "Combination Therapies for B-Cell Lymphomas Comprising Administration of Anti-CD20 Antibody".

(56) References Cited

OTHER PUBLICATIONS

Declaration of Scott Bennett, Ph.D., dated Apr. 26, 2017 (169 pages) in *Inter Partes Review* No. IPR2017-01167 re: U.S. Pat. No. 8,577,244, White, et al., "Treatment of Aggressive Non-Hodgkin's Lymphoma with Anti-CD20 Antibody".
Declaration of Scott Bennett, Ph.D., dated Apr. 27, 2017 (196 pages) in *Inter Partes Review* No. IPR2017-01168 re: U.S. Pat. No. 8,821,873, White, et al., "Treatment of Diffuse Large Cell Lymphoma with Anti-CD20 Antibody".
Declaration of Prof Dr. M.H.J Van Oers, in European Patent No. EP 15150112.9, dated Jul. 5, 2017 (5 pages).
DeNardo, et al., "A Revolution in the treatment of Non-Hodgkin's Lymphoma," Cancer Biotherapy and Radiopharmaceuticals 1998, 13(4):213-223.
DeVita et al., "Chapter 44: Hodgkin's Disease and the Non-Hodgkin's Lymphomas," in Cancer: Principles & Practice of Oncology, Second Edition, eds. DeVita, Hellman, and Rosenberg, 1985, pp. 1623-1709.
Dillman, "Monoclonal Antibodies for Treating Cancer," Annals of Internal Medicine 1989, 111:592-603.
Dudeja, et al., "Synergy of Water Soluble Prodrug Triptolide (minnelide) with Gemcitabine and Nab-paclitaxel in Pancreatic Cancer," Journal of Clinical Oncology 2016, vol. 34, No. 4_suppl., p. 259.
E1496 Forms Packet, initially dated Mar. 1993, last revised Jul. 2005 (1 page).
E1496 Protocol Accrual on Study Dates, dated Aug. 23, 2016 (4 pages).
ECOG E4494 Protocol Accrual on Study Dates, dated Aug. 23, 2016 (3 pages).
FDA FOIA Response Letter, dated Aug. 26, 2016 (3 pages).
Randomized Phase III Study in Low Grade Lymphoma Comparing Cyclophosphamide/Fludarabine to Standard Therapy Followed by Maintenance Anti-CD20 Antibody; ECOG E1496; Suggested Patient Consent Form, 1998, (3 pages).
Phase III Trial of CHOP versus CHOP and Chimeric Anti-CD20 Monoclonal Antibody (IDEC-C2B8) in Patients 60 Years of Older with Diffuse Mixed, Diffuse Large Cell and Immunoblastic Large Cell Histology Non-Hodgkin's Lymphoma; ECPG E4494, CALGB 9793; Suggested Patient Consent Form, 1997 (4 pages).
ECOG's Active Protocols: ECOG Protocols Active as of May 19, 1998, Internet Archive, Wayback Machine, http://web.archive.org/web/19980519084342/http://ecog.dfci.harvard.edu/~ecogdba/active_reports/Lymphoma.html; Revised: May 19, 1998; 1 page (Retrieved Mar. 4, 2013).
Electronic Data Gathering, Analysis, and Retrieval (EDGAR): EDGAR filer manual: Guide for electronic filing with the U.S. Securities and Exchange Commission; Release 5.10, Sep. 1996 [excerpts] (21 pages).
Ezdinili, et al., "The Effect of Intensive Intermittent Maintenance Therapy in Advanced Low-Grade Non-Hodgkin's Lymphoma," Cancer 1987, 60:156-16.
Federico, et al., "R-CVP Versus R-CHOP Versus R-FM for the Initial Treatment of Patients with Advanced-Stage Follicular Lymphoma: Results of the FOLL05 Trial Conducted by the Fondazione Italiana Linformi," Journal of Clinical Oncology 2013, 31(12):1506-1513.
Feenstra, et al., "Drug-Induced Heart Failure," Journal of the American College of Cardiology 1999, vol. 33, No. 5, pp. 1152-1162.
Feugier, "A Review of rituximab, the first anti-CD20 monoclonal antibody used in the treatment of B non-Hodgkin's lymphomas," Future Oncology 2015, 11(9):1327-1342.
Gordon, et al., "Comparison of a Second-Generation Combination Chemotherapeutic Regimen (m-BACOD) with a Standard Regimen (CHOP) for Advanced Diffuse Non-Hodgkin's Lymphoma," New Engl. J. Med. 1992, vol. 327, No. 19, pp. 1342-1349.
Haq et al., "Doxorubicin-Induced Congestive Heart Failure in Adults," Cancer 1985, vol. 56, No. 6, pp. 1361-1365.
Haskell, et al., Chapter 89: Intermediate-And High Grade Lymphomas in Cancer Treatment, 4tjh Edition, 1995 pp. 1014-1016.
Hoppe et al., "The Treatment of Advanced Stage Favorable Histology Non-Hodgkin's Lymphoma: A Preliminary Report of a Randomized Trial Comparing Single Agent Chemotherapy, Combination Chemotherapy, and Whole Body Irradiation," Blood 1981, vol. 58, No. 3, pp. 592-598.
Horning S., "Treatment Approaches to the Low-Grade Lymphomas," Blood 1994, vol. 83, No. 4, pp. 881-884.
IDEC Pharmaceuticals Corporation, Form 10-K/A for the Fiscal Year ended Dec. 31, 1997, filed with the U.S. Securities and Exchange Commission (49 pages).
IDEC Pharmaceuticals Filing Details on the EDGAR system, Mar. 3, 1998, retrieved from https://www.sec.gov/Archives/edgar/data/875045/0000936392-98-000361-index.html on Mar. 21, 2017 (1 page).
Kimby et al., "Chlorambucil/prednisone vs. CHOP in symptomatic low-grade non-Hodgkin's lymphomas: A randomized trial from the Lymphoma Group of Central Sweden," Ann. Oncol. 1994, vol. 5, supp. 2, pp. 67-71.
Kremer, "The Changing Face of Therapy for Rheumatoid Arthritis," Rheumatic Disease Clinics of North America 1995, vol. 21, No. 3, pp. 845-852.
Martelli et al., "Current Guidelines for the Management of Aggressive Non-Hodgkin's Lymphoma", Drugs 1997, 53(6): 957-972.
Moreau et al., "Peripheral blood stem cell transplantation as front-line therapy in patients aged 61 to 65 years: a pilot study," Bone Marrow Transplantation 1998, 21:1193-1196.
Patent Owner's Preliminary Response filed in *Inter Partes Review* No. IPR2015-00418 re: U.S. Pat. No. 8,329,172, (Grillo-Lopez, "Combination Therapies for B-Cell Lymphomas Comprising Administration of Anti-CD20 Antibody"), dated Jul. 10, 2017 (69 pages).
Patent Owner's Preliminary Response filed in *Inter Partes Review* No. IPR2015-01093 re: U.S. Pat. No. 8,329,172, (Grillo-Lopez, "Combination Therapies for B-Cell Lymphomas Comprising Administration of Anti-CD20 Antibody"), dated Jul. 10, 2017 (78 pages).
Patent Owner's Preliminary Response filed in *Inter Partes Review* No. IPR2015-01094 re: U.S. Pat. No. 8,557,244, dated Jul. 5, 2017 (73 pages) (White, et al., "Treatment of Aggressive Non-Hodgkin's Lymphoma with Anti-CD20 Antibody").
Patent Owner's Preliminary Response filed in *Inter Partes Review* No. IPR2015-01095 re: U.S. Pat. No. 9,296,821, (Grillo-Lopez, "Combination Therapies for B-Cell Lymphomas Comprising Administration of Anti-CD20 Antibodies"), dated Jul. 10, 2017 (79 pages).
Patent Owner's Preliminary Response filed in *Inter Partes Review* No. IPR2017-01166 re: U.S. Pat. No. 8,329,172, (Grillo-Lopez, "Combination Therapies for B-Cell Lymphomas Comprising Administration of Anti-CD20 Antibody"), dated Aug. 15, 2017 (61 pages).
Patent Owner's Preliminary Response filed in *Inter Partes Review* No. IPR2017-01167 re: U.S. Pat. No. 8,557,244 (White, et al., "Treatment of Aggressive Non-Hodgkin's Lymphoma with Anti-CD20 Antibody"), dated Aug. 8, 2017 (72 pages).
Petition for *Inter Partes Review* of U.S. Pat. No. 8,329,172, IPR2017-01166 (Grillo-Lopez, "Combination Therapies for B-Cell Lymphomas Comprising Administration of Anti-CD20 Antibody"), dated Apr. 21, 2017 by Pfizer, Inc. (67 pages).
Petition for *Inter Partes Review* of U.S. Pat. No. 8,557,244, IPR2017-01167 (White, et al., "Treatment of Aggressive Non-Hodgkin's Lymphoma with Anti-CD20 Antibody"), dated Apr. 27, 2017 by Pfizer, Inc. (63 pages).
Petition for *Inter Partes Review* of U.S. Pat. No. 8,821,873, IPR2017-01168 (White, et al., "Treatment of Diffuse Large Cell Lymphoma with Anti-CD20 Antibody"), dated Apr. 28, 2017 by Pfizer, Inc. (86 pages).
Petition for *Inter Partes Review* U.S. Pat. No. 8,329,172, IPR2017-01093 (Grillo-Lopez, "Combination Therapies for B-Cell Lymphomas Comprising Administration of Anti-CD20 Antibody"), dated Mar. 15, 2017 by Celltrion, Inc. (78 pages).
Petition for *Inter Partes Review* U.S. Pat. No. 8,557,244, IPR2017-01094 (White, et al., "Treatment of Aggressive Non-Hodgkin's Lymphoma with Anti-CD20 Antibody"), dated Mar. 15, 2017 by Celltrion, Inc. (81 pages).

(56) References Cited

OTHER PUBLICATIONS

Petition for *Inter Partes Review* U.S. Pat. No. 9,296,821, IPR2017-01095 (Grillo-Lopez, "Combination Therapies for B-Cell Lymphomas Comprising Administration of Anti-CD20 Antibodies"), dated Mar. 15, 2017 by Celltrion, Inc. (86 pages).
Pickup, "Clinical Pharmacokinetics pf Prednisone and Prednisolone," Clinical Pharmacokinetics 1979, vol. 4, pp. 111-128.
Rosenberg, "Immunotherapy and Gene Therapy of Cancer," Cancer Research 1991, (Suppl.) 51, 5074s-5079s.
Rosenberg, S.A., "The Low-Grade Non-Hodgkin's Lymphomas: Challenges and Opportunities," J. Clin. Oncol. 1985, vol. 3, No. 3, pp. 299-310.
Shipp, et al., "High-Dose CHOP as Initial Therapy for Patients with Poor-Prognosis Aggressive Non-Hodgkin's Lymphoma: A Dose-Finding Pilot Study," Journal of Clinical Oncology 1995, vol. 13, No. 12, pp. 2916-2923.
Ruuls, S.R. et al., "Novel human antibody therapeutics: the age of the Umabs," Biotechnol. J. 2008, vol. 3, pp. 1157-1171.
Smith, M.R., "Rituximab (monoclonal anti-CD20 antibody): mechanism of action and resistance," Oncogene 2003, vol. 22, No. 47, pp. 7359-7368.
Skarin et al., "Non-Hodgkin's Lymphomas: Current Classification and Management," CA Cancer J Clin 1997, 47:351-372.
Sonneveld, et. al., "Comparison of Doxorubicin and Mitoxantrone in the Treatment of Elderly Patients with Advanced Diffuse Non-Hodgkin's Lymphoma Using CHOP Versus CNOP Chemotherapy," Journal of Clinical Oncology, Oct. 1995, vol. 13, No. 10, pp. 2530-2539.
Sriskandan et al., "Aggressive management of doxorubicin-induced cardiomyopathy associated with 'low' doses of doxorubicin," Postgrad. Med. J. 1994, vol. 70, No. 828, pp. 759-761.
Thomas, et al., "Clinical Development Success Rates 2006-2015," BIO Industry Analysis, Jun. 2016 (28 pages).
Wadler, et al., "New Advances in Interferon Therapy of Cancer," The Oncologist 1997, 2:254-267.
Wang, et al., "The Synergistic in Vitro and in Vivo Antitumor Effect of Combination Therapy with Salinomycin and 5-Fluorouracil against Hepatocellular Carcinoma," PLOS One 2014, vol. 9, No. 5, pp. 1-10.
Carlson, R., "Rituximab plus CHOP: a new approach for non-Hodgkin's lymphoma?" Inpharma No. 1116 (Dec. 6, 1997) (2 pages).
Declaration of David Gindler, dated Oct. 24, 2017 (5 pages) in IPR2017-00195 re: U.S. Pat. No. 9,296,821, Grillo-Lopez, "Combination therapies for B-cell lymphomas comprising adminstration of anti-CD20 antibodies".
Declaration of Magan Raymond, dated Feb. 7, 2018 (8 pages) in IPR2017-00195 re: U.S. Pat. No. 9,296,821, Grillo-Lopez, "Combination therapies for B-cell lymphomas comprising adminstration of anti-CD20 antibodies".
Declaration of Peter McLaughlin, M.D., dated Feb. 7, 2018 (104 pages) in IPR2017-00195 re: U.S. Pat. No. 9,296,821, Grillo-Lopez, "Combination therapies for B-cell lymphomas comprising adminstration of anti-CD20 antibodies".
Declaration of Sharon Song, dated Feb. 26, 2018 (3 pages) in IPR2017-01168 re: U.S. Pat. No. 8,821,873 B2, White et al., "Treatment of diffuse large-cell lymphoma wih anti-CD20 antibody".
Declaration of Sharon Song, dated Jul. 10, 2017 (3 pages) in IPR2017-00195 re: U.S. Pat. No. 9,296,821, Grillo-Lopez, "Combination therapies for B-cell lymphomas comprising adminstration of anti-CD20 antibodies".
Deposition Transcript of Petitioner's Eqxpert Dr. Izidore Lossos, (116 pages) IPR 2017-01095 re: U.S. Pat. No. 9,296,821, Grillo-Lopez, "Combination therapies for B-cell lymphomas comprising adminstration of anti-CD20 antibodies".
Fisher et al., "Comparison of a Standard Regimen (CHOP) With Three Intensive Chemotherapy Regimens 1 for Advanced Non-Hodgkin's Lymphoma" New England Journal of Medicine 328(14):1002-1006 (1993).

Hagenbeek et al., "Maintenance of Remission With Human Recombinant Interferon Alfa-2a in Patients With Stages III and IV Low-Grade Malignant Non-Hodgkin's Lymphoma" Journal of Clinical Oncology 16(1):41-47 (1998).
McLaughlin et al., "CHOP-BLEO Plus a-Interferon (IFN) in Stage IV Low Grade Lymphoma (LGL)"American Society of Clinical Oncology (Abstract 1109), 11 (Mar. 1992) (1 page).
Patent Owner Response (POR) filed Feb. 7, 2018 by Biogen in IPR2017-01095 re: U.S. Pat. No. 9,296,821, Grillo-Lopez, "Combination therapies for B-cell lymphomas comprising administration of anti-CD20 antibodies" regarding U.S. Pat. No. 9,296,821 (Feb. 7, 2018) (83 pages).
Peterson et al., "Nodular Mixed Lymphoma (NML): A Composite Trial of Cyclophosphamide (CTX) and Cyclophosphamide, Adriamycin, Vincristine, Prednisone and Bleomycin (CAVPB)" Blood (abstract #749) 166(5 SUPPL1): 216a (Nov. 1985).
Phase II Pilot Study of Rituxan with Chemnotherapy Showed 97% Response Rate in Type of Non-Hodgkin's Lymphoma, May 18, 1998, (downloaded on Apr. 3, 2018), https://www.gene.com/media/press-releases/4781/1998-05-18/phase-ii-pilot-study-of-rituxan-with-che (4 pages).
Raphael et al., "Comparison of Chlorambucil and Prednisone Versus Cyclophosphamide, Vincristine, and Prednisone as Initial Treatment for Chronic Lymphocytic Leukemia: Long-Term Follow-Up of an Eastern Cooperative Oncology Group Randomized Clinical Trial" Journal of Clinical Oncology (5): 770-776 (1991).
Rigacci et al., "The Role of Anthracyclines in Combination Chemotherapy for the Treatment of Follicular Lymphoma: Retrospective Study of the Intergruppo Italiano Linfomi on 761 Cases" Leukemia & Lumphoma, 44(11):1911-1914 (2003).
Transcript Recorded Testimony Thomas Cerny, Oslo District Court, Oslo, Norway regarding Norwegian Patent No. 332893 (Dec. 14, 2017), pp. 1-37.
White, C. "Rituximab Immunotherapy for Non-Hodgkin's Lymphoma" Cancer Biotherapy Radiopharmaceuticals, 14(4): 241-250 (1999) (NRCC).
White, C. "Rituximab Immunotherapy for Non-Hodgkin's Lymphoma" Cancer Biotherapy & Radiopharmaceutical, 14(4): 241-250 (1999)—(Espacenet entry Feb. 24, 2017), p. 1.
Gianni et al., "In Vivo Purging of Circulating CD34+ Progenitor Cells in Low-Grade Lymphoma with Rituximab and High-Dose Chemotherapy" Blood 92(10 Suppl 1):119a (Abstract 481) (1998).
Decision Institution of *Inter Partes* Review (Paper 9), IPR2017-01166 re: U.S. Pat. No. 8,329,172, (Grillo-Lopez, "Combination Therapies for B-Cell Lymphomas Comprising Administration of Anti-CD20 Antibody"), entered Nov. 13, 2017 (30 pages).
Decision Institution of *Inter Partes* Review (Paper 8), IPR2017-01167 re: U.S. Pat. No. 8,557,244 (White, et al., "Treatment of Aggressive Non-Hodgkin's Lymphoma With Anti-CD20 Antibody"), entered Nov. 6, 2017 (14 pages).
Decision Institution of *Inter Partes* Review (Paper 6), IPR2017-01168 re: U.S. Pat. No. 8,821,873 (White, et al., "Treatment of Diffuse Large Cell Lymphoma with Anti-CD20 Antibody"), entered Nov. 6, 2017 (14 pages).
"What is a Stem Cell Transplant (Bone Marrow Transplant)?," Cancer.Net, Jan. 2016 (downloaded on Feb. 14, 2018), from https://www.cancer.net/navigating-cancer-care/howcancer-treated/bone-marrowstem-cell-transplantation/what-stem-cell-transplant-bone-marrow-transplant. (Feb. 14, 2018) (6 pages).
Affidavit of Christopher Butler with Exhibit A dated Sep. 28, 2016 (7 pages).
Al-Ismail et al., "Combination Chemotherapy Including Epirubicin for the Management of Non-Hodgkin's Lymphoma" Eur J Cancer Clin Oncol 23(9):1379-1384 (1987).
Armitage, J., "Treatment of Non-Hodgkin's Lymphoma" The New England Journal of Medicine 328(14):1023-1030 (1993).
Buske et al., "Monoclonal Antibody Therapy for B Cell Non-Hodgkin's Lymphomas: Emerging Concepts of a Tumour-targeted Strategy" European Journal of Cancer 35(4):549-557 (1999).
Carlson, R., "Rituximab plus CHOP: a new approach for non-Hodgkin's lymphoma?" Inpharma No. 1116 Aug. 1, 2016 (Dec. 6, 1997) (2 pages).
Curriculum Vitae of Brad S. Kahl, M.D. (Jan. 9, 2018) (30 pages).

(56) References Cited

OTHER PUBLICATIONS

Decision of Norwegian District Court dated Feb. 7, 2018 regarding Norwegian Patent No. 332893 (45 pages) with English translation thereof (43 pages).
Declaration of Brad S. Kahl, M.D., dated Feb. 26, 2018 (55 pages) in IPR2017-01168 re: U.S. Pat. No. 8,821,873 B2, White, et al., "Treatment of diffuse large-cell lymphoma with anti-CD20 antibody".
Declaration of David Gindler, dated Oct. 24, 2017 (5 pages) in IPR2017-01095 re: U.S. Pat. No. 9,296,821, Grillo-Lopez, "Combination therapies for B-cell lymphomas comprising administration of anti-CD20 antibodies".
Declaration of Megan Raymond, dated Feb. 7, 2018 (8 pages) in IPR2017-01095 re: U.S. Pat. No. 9,296,821, Grillo-Lopez, "Combination therapies for B-cell lymphomas comprising administration of anti-CD20 antibodies".
Declaration of Peter McLaughlin, M.D., dated Feb 7, 2018 (104 pages) in IPR2017-01095 re: U.S. Pat. No. 9,296,821, Grillo-Lopez, "Combination therapies for B-cell lymphomas comprising administration of anti-CD20 antibodies".
Declaration of Sharon Song, dated Feb. 26, 2018 (3 pages) in IPR2017-01168 re: U.S. Pat. No. 8,821,873 B2, White et al., "Treatment of diffuse large-cell lymphoma with anti-CD20 antibody".
Declaration of Sharon Song, dated Jul. 10, 2017 (3 pages) in IPR2017-01095 re: U.S. Pat. No. 9,296,821, Grillo-Lopez, "Combination therapies for B-cell lymphomas comprising administration of anti-CD20 antibodies".
Deposition Transcript of Howard Ozer, M.D., Ph.D., (90 pages) in IPR2017-01168 re: U.S. Pat. No. 8,821,873 B2, White et al., "Treatment of diffuse large-cell lymphoma with anti-CD20 antibody" (Feb. 15, 2018).
Deposition Transcript of Petitioner's Expert Dr. Izidore Lossos, (116 pages) IPR 2017-01095 re: U.S. Pat. No. 9,296,821, Grillo-Lopez, "Combination therapies for B-cell lymphomas comprising administration of anti-CD20 antibodies" (Jan. 25, 2018).
Eastern Cooperative Oncology Group (ECOG) Phase III Trial of Rituxan Maintenance Therapy in Indolent Non-Hodgkin's Lymphoma Reaches Pre-Specified Efficacy Endpoint Early (Nov. 2003) (p. 1).
Embace entry for White, C. "Rituximab Immunotherapy for Non-Hodgkin's Lymphoma" Cancer Biotherapy & Radiopharmaceuticals, 14(4): 241-250 (1999) (1 page).
EP 2990054A1 from Google Patents downloaded May 25, 2017, pp. 1-26.
Ezdinli et al., "Chlorambucil Therapy for Lymphomas and Chronic Lymphocytic Leukemia" Journal of American Medical Association 191(6):444-450 (1965).
Fisher et al., "Comparison of a Standard Regimen (CHOP) With Three Intensive Chemotherapy Regimens for Advanced Non-Hodgkin's Lymphoma" New England Journal of Medicine 328(14):1002-1006 (1993).
Goss, P., "Non-Hodgkin's Lymphomas in Elderly Patients" Leukemia and Lymphoma 10:147-156 (1993).
Gribben et al., "Detection of Residual Lymphoma Cells by Polymerase Chain Reaction in Peripheral Blood is Significantly Less Predictive for Relapse Than Detection in Bone Marrow" Blood 83(12); 3800-3807 (1994).
Gribben et al., "Effectiveness of High-Dose Combination Chemotherapy and Autologous Bone Marrow Transplantation for Patients With Non-Hodgkin's Lymphomas Who Are Still Responsive to Conventional-Dose Therapy" Journal of Clinical Oncology, 7(11):1621-1629 (1989).
Grossbard et al. Malignant Lymphomas "18 Monoclonal Antibody Therapy of Lymphoma" BC Decker Inc., vol. 1:301-315 (2002).
Grossbard et al., "Clinical Status and Optimal use of Rituximab for B-Cell Lymphomas" Oncology (published online www.cancernetwork.com on Dec. 1, 1998 (retrieved Feb. 4, 2013 http://www.cancernetwork.com/print/article/10165/66803?printable=true), 12(12):1-2 (Dec. 1, 1998).

Hagenbeek et al., "Maintenance of Remission With Human Recombinant Inerferon Alfa-2a in Patients With Stages III and IV Low-Grade Malignant Non-Hodgkin's Lymphoma" Journal of Clinical Oncology 16(1):41-47 (1998).
Haioun et al., "Benefit of Autologous Bone Marrow Transplantation Over Sequential Chemotherapy in Poor-Risk Aggressive Non-Hodgkin's Lymphoma: Updated Results of the Prospective Study LNH87-2" Journal of Clinical Oncology 15(3):1131-1137 (1997).
Han et al., "Chlorambucil vs. Combined Chlorambucil-Corticosteroid Therapy in Chronic Lymphocytic Leukemia" Cancer 31(3):501-508 (1973).
Korsmeyer, S., "Bcl-2 Initiates a New Category of Oncogenes: Regulators of Cell Death" Blood 80(4):879-886 (1992).
Lopez-Guillermo et al., "The Clinical Significance of Molecular Response in Indolent Follicular Lymphomas" Blood 91(8):2955-2960 (1998).
McLaughlin et al., "CHOP-BLEO Plus α-Interferon (IFN) in Stage IV Low Grade Lymphoma (LGL)" American Society of Clinical Oncology (Abstract 1109), Mar. 11, 1992 (1 page).
McLaughlin et al., "Stage III Follicular Lymphoma: Durable Remissions with a Combined Chemotherapy-Radiotherapy Regimen" Journal of Clinical Oncology 5(6):867-874 (1987).
Pammolli et al., "The productivity crisis in pharmaceutical R&D" Nature 10:428-438 (2011).
Parlier et al., "Combination Chemotherapy with Cyclophosphamide Vincristine, Prednisone and the Contribution of Adriamycin in the Treatment of Adult Non-Hodgkin's Lymphomas a Report of 131 Cases" Cancer 50:401-409 (1982).
Patent Owner Response (POR) filed Feb. 26, 2018 by Biogen in IPR2017-01168 re: U.S. Pat. No. 8,821,873, White, et al., "Treatment of diffuse large-cell lymphoma with anti-CD20 antibody" (Feb. 26, 2018) (68 pages).
Patent Owner Response (POR) filed Feb. 7, 2018 by Biogen in IPR2017-01095 re: U.S. Pat. No. 9,296,821, Grillo-Lopez, "Combination therapies for B-cell lymphomas comprising adminstration of anti-CD20 antibodies" regarding U.S. Pat. No. 9,296,821 (Feb. 7, 2018) (83 pages).
Peterson et al., "Nodular Mixed Lymphoma (NML): A Composite Trial of Cyclophosphamide (CTX) and Cyclophosphamide, Adriamycin, Vincristine, Prednisone and Bleomycin (CAVPB)" Blood (abstract #749) 66(5 Suppl1): 216a (Nov. 1985).
Phase II Pilot Study of Rituxan with Chemotherapy Showed 97% Response Rate in Type of Non-Hodgkin's Lymphoma, May 18, 1998, (downloaded on Apr. 3, 2018), https://www.gene.com/media/press-releases/4781/1998-05-18/phase-ii-pilot-study-of-rituxan-with-che (4 pages).
Philip et al., "High-Dose Therapy and Autologous Bone Marrow Transplantation After Failure of Conventional Chemotherapy in Adults With Intermediate-Grade or High-Grade Non-Hodgkin's Lymphoma" The New England Journal of Medicine 316(24):1493-1498 (1987).
Raphael et al., "Comparison of Chlorambucil and Prednisone Versus Cyclophosphamide, Vincristine, and Prednisone as Initial Treatment for Chronic Lymphocytic Leukemia: Long-Term Follow-Up of an Eastern Cooperative Oncology Group Randomized Clinical Trial" Journal of Clinical Oncology 9(5): 770-776 (1991).
Rigacci et al., "The Role of Anthracyclines in Combination Chemotherapy for the Treatment of Follicular Lymphoma: Retrospective Study of the Intergruppo Italiano Linfomi on 761 Cases" Leukemia & Lymphoma, 44(11):1911-1917 (2003).
Rituxan® (Rituximab) Prescribing Information dated Apr. 2016 (Apr. 2016), pp. 1-39.
Smalley et al., "Interferon Alfa Combined with Cytotoxic Chemotherapy for Patients with Non-Hodgkin's Lymphoma" New England Journal of Medicine 327(19): 1336-1341 (1992).
Transcript of Recorded Testimony of Nancy Turman (via telephone), Oslo District Court, Oslo, Norway regarding Norwegian Patent No. 332893 (Dec. 12, 2017), pp. 1-13.
Transcript of Recorded Testimony of Prof. Marinus H. J. Van Oers, Oslo District Court, Oslo, Norway regarding Norwegian Patent No. 332893 (Dec. 14, 2017), pp. 1-44.

(56) References Cited

OTHER PUBLICATIONS

Transcript of Recorded Testimony of Professor Walter Longo, MD, Oslo District Court, Oslo, Norway regarding Norwegian Patent No. 332893 (Dec. 13, 2017), pp. 1-26.

Transcript of Recorded Testimony of Thomas Cerny, Oslo District Court, Oslo, Norway regarding Norwegian Patent No. 332893 (Dec. 14, 2017), pp. 1-37.

White, C. "Rituximab Immunotherapy for Non-Hodgkin's Lymphoma" Cancer Biotherapy & Radiopharmaceuticals, 14(4): 241-250 (1999) (NRCC).

White, C. "Rituximab Immunotherapy for Non-Hodgkin's Lymphoma" Cancer Biotherapy & Radiopharmaceuticals, 14(4): 241-250 (1999) (University of Michigan).

White, C. "Rituximab Immunotherapy for Non-Hodgkin's Lymphoma" Cancer Biotherapy & Radiopharmaceuticals, 14(4): 241-250 (1999) (University of Minnesota).

White, C. "Rituximab Immunotherapy for Non-Hodgkin's Lymphoma" Cancer Biotherapy & Radiopharmaceuticals, 14(4): 241-250 (1999)—(Espacenet entry Feb. 24, 2017), p. 1.

"Affidavit of Professor Henry Miles Prince AM" (Unsworn copy; Federal Court of Australia, F. Hoffmann—La Roche AG and another (Applicants); Sandoz Pty Ltd (Respondent); No. NSD 2265 of 2017; 97 pages and 185 pages; Annexures MP-1, MP-2, and MP-12 to MP-18 provided), (Apr. 2018).

Berczi et al. Immune Modulating Agents "Hormones as Immune Modulating Agents" Kresina, T., New York:Marcel Dekker, Inc. ,:75-120 ( 1998).

Bezwoda et al., "Long-term results of a multicentre randomised, comparative phase III trial of CHOP versus CNOP regimens in patients with intermediate- and high-grade non-Hodgkin's lymphomas" Eur J Cancer 31A(6):903-911 ( 1995).

ClinicalTrials.gov, "Combination Chemotherapy With or Without Monoclonal Antibody Therapy in Treating Patients With Stage III or Stage IV Low-Grade Non-Hodgkin's Lymphoma" (ECOG 1496 rituximab; NCT00003204; First Posted Jan. 27, 2003; Last Update Posted Feb. 27, 2013; 9 pages), ( 2017) https://www.clinicaltrials.gov/ct2/show/NCT00003204?term=ECOG+1496&intr=rituximab&rank=1 .

ClinicalTrials.gov, "Combination Chemotherapy With or Without Monoclonal Antibody Therapy in Treating Older Patients With Non-Hodgkin's Lymphoma" (ECOG 4494 rituximab phase 3; NCT00003150; First Posted Feb. 16, 2004; Last Update Posted Jun. 21, 2013; 7 pages), ( 2017) https://www.clinicaltrials.gov/ct2/show/NCT00003150?term=ECOG+4494&intr=rituximab&phase=2&rank=1.

Coiffier et al., "A multicenter, randomized phase II study of rituximab (MABTHERA) at two dosages in patients with relapsed or refractory intermediate grade lymphoma or in elderly patients in first-line therapy" British Journal of Haematology (Abstract P-0950), 102(1):238 (Jul. 1998).

Coiffier et al., "Rituximab in diffuse large B cell and mantle cell lymphomas" Annals of Oncology (Abstract 020), 9( Suppl 3):27 ( 1998).

Coiffier, B., "Mabthera in aggressive lymphoma: An update on its efficacy and toxicity" Annals of Applications in CD20+ malignancies), 10( Suppl 3):213 (Jun. 1, 1999).

Coiffier, B., "Treatment of aggressive non-Hodgkin's lymphoma" Semin Oncol 26(5 Suppl 14):12-20 (Oct. 1999).

Dallegri et al., "Defective antibody-dependent tumour cell lysis by neutrophils from cancer patients" Clin Exp Immunol 77(1):58-61 (Jul. 1989).

"Declaration of Megan Raymond in Support of Patent Owner's Response" (*Pfizer, Inc.* vs. *Biogen, Inc.*; Case IPR2018-00186; U.S. Pat. No. 9,296,821 B2, Grillo-Lopez, Combination Therapies for B-Cell Lymphomas Comprising Administration of Anti-CD20 Antibodies; 5 pages), (Mar. 13, 2018).

"Declaration of Sharon Song" (*Pfizer, Inc.* vs. *Biogen, Inc.*; Case IPR2018-00285; U.S. Pat. No. 8,329,172, Grillo-Lopez, Combination Therapies for B-Cell Lymphomas Comprising Administration of Anti-CD20 Antibodies; 4 pages), (Apr. 11, 2018).

"Declaration of Sharon Song" (*Pfizer, Inc.* vs. *Biogen, Inc*; Case IPR2018-00231; U.S. Pat. No. 9,504,744, White et al., Treatment of Diffuse Large-Cell Lymphoma with Anti-CD20 Antibody; 3 pages), (Mar. 19, 2018).

Definition of myelosuppression—NCI Dictionary of Cancer Terms—National Cancer Institute, 1 page (Retrieved on Mar. 19,2018) https://www.cancer.gov/publications/dictionaries/cancer-terms/def/myelosuppression.

"Final Written Decision 35 U.S.C. 318(a) and 37 C.F.R. 42.73" (*Celltrion, Inc. and Pfizer, Inc.* vs. *Biogen, Inc. and Genentech, Inc.*; Case IPR2016-01614; U.S. Pat. No. 7,820,161, Curd et al., Treatment of Autoimmune Diseases),:1-25 (Feb. 21, 2018).

Flinn et al., "Fludarabine and cycloposphamide as first therapy for indolent lymphoproliferative disorders: response rates and toxicity" Blood (Abstract 2345), 88(10 Suppl 1 (Part 1 of 2)):589a (Nov. 15, 1996).

Flinn et al., "Fludarabine and cyclophosphamide: a highly active and well tolerated regimen for patients with previously untreated indolent lymphomas" Blood (Abstract 1706), 92(10 Suppl 1 (Part 1 of 2)):413a (Nov. 15, 1998).

Freedman et al., "Autologous bone marrow transplantation in 69 patients with a history of low-grade B-cell non-Hodgkin's lymphoma" Blood 77(11):2524-2529 (Jun. 1, 1991).

"Genentech, Inc. and Biogen, Inc.'s Patent Owner Response" (*Celltrion, Inc.* vs. *Genentech,Inc. and Biogen, Inc.*; Case IPR2016-01614; U.S. Pat. No. 7,820,161, Curd et al., Treatment of Autoimmune Diseases; 70 pages (redacted)), (Jun. 2, 2017).

Gutheil et al., "Phase II study of Rituximab (RITUXAN) in Patients With Previously Untreated Low-grade or Follicular Non-Hodgkin's Lymphoma" Annals of Oncology (Abstract 460), 10 (Suppl 3):127 (Jun. 1999).

Hagberg; Case No. 16-206868TVI-OTIR/05; *Celltrion, Inc., Sandoz GmBH, Sandoz A/S* vs. *Biogen, Inc.*; transcription and translation of audio recording of Judge Stole, Hans Hagberg, Ingvild Hanssen-Bauer, and Judge Arne Kolstad; 14 pages; Certification dated Apr. 9, 2018 attached. (Audio Recording Date Dec. 14, 2017).

Hashimoto et al., "Antibody-dependent cell-mediated cytotoxicity against influenza virus-infected cells" J Infect Dis 148(5):785-794 (Nov. 1983).

Hoffman, M., "Cladribine and fludarabine for the treatment of lymphoproliferative disorders" Cancer Investigation (Abstract 2), 14( Suppl 1):2-3 ( 1996).

Khaled et al., "A randomized EPOCH vs. CHOP front-line therapy for aggressive non-Hodgkin's lymphoma patients: long-term results" Ann Oncol 10(12):1489-1492 (Dec. 1999).

Lee et al., "Fatal cyclophosphamide cardiomyopathy: its clinical course and treatment" Bone Marrow Transplantation 18(3):573-577 (Sep. 1996).

Lippman et al., "The prognostic significance of the immunotype in diffuse large-cell lymphoma: a comparative study of the T-cell and B-cell phenotype" Blood 72(2):436-441 (Aug. 1988).

Lowdell et al., "Less is More: The Role of Purging in Hematopoietic Stem Cell Transplantation" The Oncologist 2(4):268-274 ( 1997).

Maloney et al., "Newer treatments for non-hodgkin's lymphoma: monoclonal antibodies" Oncology 12(10 Suppl 8):63-76 (Oct. 1998).

Nakamine et al., "Prognostic significance of clinical and pathologic features in diffuse large B-cell lymphoma" Cancer 71(10):3130-3137 (May 15, 1993).

National Cancer Institute, Cancer Therapy Evaluation Program, Common Toxicity Criteria Manual, Toxicity Criteria, Version 2.0 (32 pages), (Jun. 1, 999).

Nguyen et al., "IDEC-C2B8 anti-CD20 phase II trial: results on bone marrow and peripheral blood tumor response in patients with low grade non-Hodgkin's lymphoma/lymphoproliferative disorders" Blood (Abstract 2277), 90(10 Suppl 1):511a ( 1997).

Niitsu, N., "Non-Hodgkin's lymphoma in the elderly: a guide to drug treatment" Drugs & Aging 14(6):447-457 (Jun. 1999).

"Patent Owner Preliminary Response" (*Pfizer, Inc.* vs. *Biogen, Inc.*; Case IPR2018-00285; U.S. Pat. No. 8,329,172, Grillo-Lopez, Combination Therapies for B-Cell Lymphomas Comprising Adminstration of Anti-CD20 Antibody; 82 pages; Patent Owner's Exhibit List Attached), (Apr. 11, 2018).

(56) References Cited

OTHER PUBLICATIONS

"Patent Owner Preliminary Response" (*Pfizer, Inc.* vs. *Biogen, Inc.*; Case IPR2018-00231; U.S. Pat. No. 9,504,744, White et al., Treatment of Diffuse Large-Cell Lymphoma with Anti-CD20 Antibody; 80 pages; Patent Owner's Exhibit List Attached), (Mar. 19, 2018).
"Patent Owner Preliminary Response Under 37 C.F.R. 42.107" (*Pfizer, Inc.* vs. *Biogen, Inc.*; Case IPR2018-00186; U.S. Pat. No. 9,296,821 B2, Grillo-Lopez, Combination Therapies for B-Cell Lymphomas Comprising Adminstration of Anti-CD20 Antibody; 76 pages, (Mar. 19, 2018).
Physicians' Desk Reference "Adriamycin RDF, Adriamycin PFS" (product information), 52 edition, Montvale, NJ:Medical Economics Company, Inc.,:2237-2239 ( 1998).
Shipp et al., "Patterns of relapse in large-cell lymphoma patients with bulk disease: implications for the use of adjuvant radiation therapy" J Clin Oncol 7(5):613-618 (May 1989).
Solimando et al., "Doxorubicin-induced hypersensitivity reactions" Drug Intell Clin Pharm 18(10):808-811 (Oct. 1984).
Summerhayes, M., "Rituximab: a new modality in lymphoma treatment" European Hospital Pharmacy 5(3):126-133 (Sep. 1999).
Tirelli et al., "CHOP is the standard regimen in patients > or =70 years of age with intermediate-grade and high-grade non-Hodgkin's lymphoma: results of a ramdomized study of the European Organization for Research and Treatment of Cancer Lymphoma Cooperative Study Group" J Clin Oncol 16(1):27-34 (Jan. 1998).
Translation of transcription of Steinar Aamdal Testimony; Oslo District Court; Court case No. 16-206868TVI-OTIR/05, pp. 1-63 (Testimony Date Dec. 13, 2017).
Turgeon, M. Clinical Hematology: Theory and Procedures (re: lymphocytes), 4th edition, Philadelphia:Lippincott Williams & Wilkins,:221 (2005).
Velasquez et al., "Risk classification as the basis for clinical staging of diffuse large-cell lymphoma derived from 10-year survival data" Blood 74(2):551-557 (Aug. 1, 1989).
Vose et al., "Phase II Study of Rituximab in Combination with CHOP Chemotherapy in Patients with Previously Untreated Intermediate- or High-Grade Non Hodgkin's Lymphoma (NHL)" Annals of Oncology (Abstract 195), 10( Suppl 3):58 ( 1999).
Wendum et al., "Follicular large-cell lymphoma treated with intensive chemotherapy: an analysis of 89 cases included in the LNH87 trial and comparison with the outcome of diffuse large B-cell lymphoma Groupe d'Etude des Lymphomes de l'Adulte" J Clin Oncol 15(4):1654-1663 (Apr. 1997).
Whelan et al., "Fludarabine phosphate for the treatment of low grade lymphoid malignancey" Br J Cancer 64(1):120-123 (Jul. 1991).
Yuen, A., "Progress in the non-Hodgkin's lymphomas" Annals of Oncology 10( Suppl 6):S19-S22 (1999).
Coiffier, "Treatment of Non-Follicular Indolent Disseminated Lymphomas" British Journal of Haematology 102(1):271 (Abstract Hif-1088) ( 1998).
Czuczman et al., "Rituximab in Combination with CHOP or Fludarabine in Low-Grade Lymphoma" Seminars in Oncology 29(1 Suppl 2):36-40 ( 2002).
Gianni et al., "In Vivo Purging of Circulating CD34+ Progenitor Cells in Low-Grade and High-Dose Chemotherapy" Blood 92(10 Suppl 1):119a (Abstract 481) ( 1998).
Grillo-Lopez et al., "Pilot Efficacy Studies of Rituximab in Combination with Chemotherapy, Biologicals, or Radioimmunotherapy" Annals of Oncology 10( Suppl 3):179 (Abstract 661) ( 1999).
Howard et al., "Rituximab and CHOP Induction Therapy for Newly Diagnosed Mantle-Cell Lymphoma: Molecular Complete Responses Are Not Predictive of Progression-Free Survival" Journal of Clinical Oncology 20(5):1288-1294 ( 2002).
Lenz et al., "Immunochemotherapy with Rituximab and Cyclophosphamide, Doxorubicin, Vincristine, and Prednisone Significantly Improves Response and Time to Treatment Failure, But Not Long-Term Outcome in Patients with Previously Untreated Mantle Cell Lymphoma: Results of a Prospective Randomized Trial of the German Low Grade Lymphoma Study Group (GLSG)" Journal of Clinical Oncology 23(9):1984-1992 ( 2005).
Maloney, "Advances in Immunotherapy of Hematologic Malignancies" Curr Opin Hematol 5(4):237-243 ( 1998).
Maloney, "Antibody therapy has arrived. Now where does it fit?" Annals of Oncology 10(6):619-621 ( 1999).
Porcu et al., Current Problems in Cancer 22(5):283-368 ( 1998).
Press et al., "Immunotherapy of Non-Hodgkin's Lymphomas" Hematology:221-240 ( 2001).
Von Mehren et al., "Monoclonal Antibody Therapy for Cancer" Annual Review of Medicine 54:343-369 (2003).
Waldmann et al., "Emerging Therapies: Spectrum of Applications of Monoclonal Antibody Therapy" Hematology:394-408 ( 2000).
Zucca et al., "Management of rare forms of lymphoma" Current Opinion in Oncology 10(5):377-384 ( 1998).
Petition for *Inter Partes* Review of U.S. Pat. No. 9,296,821, IPR2018-00186 (Grillo-Lopez, "Combination Therapies for B-Cell Lymphomas Comprising Administration of Anti-CD20 Antibodies"), dated Dec. 1, 2017 by Pfizer, Inc. (74 pages).
Declaration of Howard Ozer, M.D., Ph.D., dated Dec. 1, 2017 (110 pages) in *Inter Partes* Review No. IPR2018-00186 re: U.S. Pat. No. 9,296,821, Grillo-Lopez, "Combination Therapies for B-Cell Lymphomas Comprising Administration of Anti-CD20 Antibodies".
Declaration of Sylvia D. Hall-Ellis, Ph.D., dated Nov. 27, 2017 (124 pages) in *Inter Partes* Review No. IPR2018-00186 re: U.S. Pat. No. 9,296,821, Grillo-Lopez, "Combination Therapies for B-Cell Lymphomas Comprising Administration of Anti-CD20 Antibodies".
Petition for *Inter Partes* Review of U.S. Pat. No. 9,504,744, IPR2018-00231 (White, et al., "Treatment of Diffuse Large-Cell Lymphoma with Anti-CD20 Antibody"), dated Dec. 1, 2017 by Pfizer, Inc. (78 pages).
Declaration of Howard Ozer, M.D., Ph.D., dated Dec. 1, 2017 (114 pages) in *Inter Partes* Review No. IPR2018-00231 re: U.S. Pat. No. 9,504,744, White, et al., "Treatment of Diffuse Large-Cell Lymphoma with Anti-CD20 Antibody".
Declaration of Scott Bennett, Ph.D., dated Nov. 28, 2017 (30 pages) in *Inter Partes* Review No. IPR2018-00231 re: U.S. Pat. No. 9,504,744, White, et al., "Treatment of Diffuse Large-Cell Lymphoma with Anti-CD20 Antibody".
Declaration of Steiner Aamdal, Professor Emeritus in Oslo District Court, case No. 16-206868TVI-OTIR dated Nov. 13, 2017, pp. 1-18.
Expert Report of Professor Marinus H. J. Van Oers in Oslo District Court, Case No. 16-206868TV1-OTIR/05, dated Nov. 27, 2017, pp. 1-17.
2016 RITUXAN (Rituximab) prescribing information; Initial US Approval Nov. 1997; Revised Apr. 2016 (39 pages).
"Combination Chemotherapy with or without Monoclonal Antibody Therapy in Treating Patients with Stage III or Stage IV Low-Grade Non-Hodgkin's Lymphoma," Cancer.gov, dated Mar. 3, 2015, retrieved Sep. 21, 2015 from http://www.cancer.gov/clinicaltrials/search/view?cdrid=653666&version=HealthProfessional&protocolsearchid=13923514, (4 pages).
Anderson D.R. et al. Second IBC Int'l. Conference on Antibody Engineering, San Diego, Dec. 16-18, 1991. Immunoreactivity and effector function associated with a chimeric anti-CD20 antibody (abstract of presentation).
Clinical Review of BLA Reference No. BLA 97-0260 and BLA 97-0244, pp. 1-40 with cover page signed: Nov. 1997; the source is available on the Internet (as of Nov. 28, 2013) at the following (URL): http://www.fda.gov/downloads/Drugs/DevelopmentApprovalProcess/HowDrugsareDevelopedandApproved/ApprovalApplications/TherapeuticBiologicApplications/ucm113330.pdf.
ClinicalTrials.gov, "Combination Chemotherapy With or Without Monoclonal Antibody Therapy in Treating Patients With Stage III or Stage IV Low-Grade Non-Hodgkin's Lymphoma", http://clinicaltrials.gov/show/NCT00003204; Study Start Date: Mar. 1998, Primary Completion Date: May 2006, Last updated: Feb. 26, 2013; Last verified: Feb. 26, 2013; pp. 1-4 (Retrieved Mar. 4, 2013).
Hekman A. et al. *Ann. Rept. Netherlands Cancer Inst.*, Amsterdam, pp. 47-48, 1993. Immunotherapy.

(56) References Cited

OTHER PUBLICATIONS

IDEC Pharmaceuticals Corp., press release dated Dec. 9, 1996. IDEC Pharmaceuticals and Genentech announce positive final results for pivotal phase III trial of IDEC-C2B8 as single agent.
Kimura et al., "VII Medicaments for hematologic diseases 'lymphoid malignancy'; 177. Drug therapies for non-Hodgkin's lymphoma" Medicina vol. 24, No. 10 (1987), pp. 2194-2197 (English translation of Japanese Office Action dated Dec. 25, 2012, filed in corresponding JP Patent Application No. 2000-564662, Antonio J. Grillo-Lopez, Combination Therapies for B-Cell Lymphomas Comprising Administration of Anti-CD20 Antibody).
Decision Institution of *Inter Partes* Review (Paper No. 12), IPR2017-01093 re: U.S. Pat. No. 8,329,172, entered Oct. 6, 2017 (26 pages), Grillo-Lopez, "Combination Therapies for B-Cell Lymphomas Comprising Administration of Anti-CD20 Antibody".
Decision Institution of *Inter Partes* Review (Paper 12), IPR2017-01094 re: U.S. Pat. No. 8,557,244, entered Oct. 2, 2017 (18 pages), White, et al., "Treatment of Aggressive Non-Hodgkin's Lymphoma with Anti-CD20 Antibody".
Decision Institution of *Inter Partes* Review (Paper No. 12), IPR2017-01095 re: U.S. Pat. No. 9,296,821, entered Oct. 6, 2017 (35 pages), Grillo-Lopez, "Combination Therapies for B-Cell Lymphomas Comprising Administration of Anti-CD20 Antibodies".
Title 21 Code of Federal Regulations, Subpart D, section 14.60-14.75, Apr. 1, 1997 ed., pp. 152-154.
62 Federal Register 32, Food and Drug Administration, Advisory Committees; Tentative Schedule of Meetings for 1997, Feb. 18, 1997, pp. 7237-7240.
62 Federal Register 115, Jun. 16, 1997, pp. 32619.
"Cytoxan®, Etophose®, Leukeran®, Mepron®, Oncovin®," Physicians' Desk Reference (52nd ed. 1998), Published by Medical Economics Company, Inc. (11 pages).
"Rituxan™ (Rituximab)" Physicians' Desk Reference (53rd ed. 1999), Published by Medical Economics Company (11 pages).
1999 NCI Cancer Toxicity Criteria Manual, Common Toxicity Criteria, Version 2.1, Jun. 1, 1999, available at https://ctep.cancer.gov/protocoldevelopment/electronic_applications/docs/ctcmanual_v4_10-4-99.pdf (retrieval date unavailable) (32 pages).
Campbell et al., "B-Lymphocyte Responses," Clinical Oncology, Abeloff, et al., Eds., Published by Churchill Livingstone, Inc. 1995, 100-126.
Collins, "The Lunch", https://www.gene.com/stories/the-lunch?topic=hematology, pp. 1-10, retrieved Aug. 7, 2017 (in Aug. 14, 2017 for OA U.S. Appl. No. 13/524,837).
Declaration of Christopher Butler re: ECOG Protocols Active as of May 19, 1998, signed on Oct. 11, 2016 (4 pages), (ECOG's Active Protocols: ECOG Protocols Active as of May 19, 1998, Internet Archive, Wayback Machine, http://web.archive.org/web/19980519084342/http://ecog.dfci.harvard.edu/~ecogdba/active_reports/Lymphoma.html; Revised: May 19, 1998; 1 page (Retrieved Mar. 4, 2013)).
Hochster, et al., "Prolonged Time to Progression (TTP) in Patients With Low Grade Lymphoma (LGL) Treated With Cyclophosphamide (C) and Fludarabine (F) [ECOG 1491]," American Society of Clinical Oncology Program/Proceedings, Thirty Fourth Annual Meeting May 16-19, 1998, Los Angeles, California , vol. 17, Abstract 66, (5 pages).
Rituxan (Rituximab) label (Nov. 1997) (2 pages).
"A randomized, phase III trial to determine the effect of consolidation with rituximab (IDEC C2B8-Mabthera) in patients with CD20+ follicular or mantle lymphoma having received induction therapy with rituximab weekly x4," Minutes Protocol SAKK 35/98, Swiss Group for Clinical Cancer Research, Dec. 18, 1998, Activation Date Jan. 7, 1998, pp. 1-27.
"Phase II Trial of CHOP Followed by Rituximab, a Chimeric Monoclonal Anti-CD20 Antibody, for Treatment of Newly Diagnosed Follicular Non-Hodgkin's Lymphoma: SWOG 9800," Oncology Review Article, Mar. 1, 2002, pp. 1-2.

"Understanding Maintenance Therapy," Approved by the Cancer. Net Editorial Board, Aug. 2015, ASCO Website Printout, retrieved Jul. 1, 2016.
"Vincristine," Wikipedia, the free encyclopedia, retrieved Jul. 23, 2015, https://en.wikipedia.org/wiki/Vincristine (3 pages).
Aguiar-Bujanda, et al., "Critical appraisal of rituximab in the maintenance treatment of advanced follicular lymphoma," Cancer Management and Research, 2015, vol. 7, pp. 319-330.
Arber, et al., "The 2016 revision to the World Health Organization classification of myeloid neoplasms and acute leukemia," Blood, 2016, vol. 127, No. 20, pp. 2391-2405.
Ardeshna, et al., "Long-term effect of a watch and wait policy versus immediate systemic treatment for asymptomatic advanced-stage non-Hodgkin lymphoma: a randomised controlled trial," Lancet, 2003, 362:516-5222.
Aviles, et al., "Long-Term Results in Patients with Low-Grade Nodular Non-Hodgkin's Lymphoma : a randomized trial comparing chemotherapy plus radiotherapy with chemotherapy alone," Acta Oncologica, 1991, vol. 30, No. 3, pp. 329-333.
Bagley, et al., "Advanced Lymphosarcoma: Intensive Cyclical Combination Chemotherapy with Cyclophosphamide, Vincristine, and Prednisone," Annals of Internal Medicine, 1972, 76:227-234.
Bennett, et al., "Cancer Insurance Policies in Japan and the United States," W. J. Med, 1998, 168(1):17-22.
Brice, et al., "Comparison in low-tumor-burden follicular lymphomas between an initial no-treatment policy, prednimustine, or interferon alfa: a randomized study from the Group d'Etude des Lymphomas Folliculaires," J. Clin Oncol., 1997, 15(3): 1110-1117.
Cheson, "Current Approaches to Therapy for Indolent Non-Hodgkin's Lymphoma," Nutritional Outlook, Review Article, Oct. 2, 1998, pp. 1-16.
Chow, et al., "Oncogene-specific formation of chemoresistant murine hepatic cancer stems cells," Hepatology, 2012, 56(4), pp. 1331-1341.
Coleman, "Glucocorticoids in cancer therapy," Biotherapy, 1992, No. 4, pp. 37-44.
Definition of consolidation Therapy, NCI Dictionary of Cancer Terms—National Cancer Institute, http://www.cancer.gov/publicications/dictionaries/cancer-terms?CdrID=45654, retrieved Oct. 9, 2017 (1 page).
Definition of Maintenance Therapy, NCI Dictionary of Cancer Terms—National Cancer Institute, http://www.cancer.gov/publicications/dictionaries/cancer-terms?CdrID=45768, retrieved Nov. 17, 2015 (1 page).
Forstpointner, et al., "Maintenance therapy with rituximab leads to a significant prolongation of response duration after salvage therapy with a combination of rituximab, fludarabine, cyclophosphamide, and mitoxantrone (R-FCM) in patients with recurring and refractory follicular and mantle cell lymphomas: results of a prospective randomized study of the German Low Grade Lymphoma Study Group (GLSG)," Blood, 2006, vol. 108, No. 13, pp. 4003-4008.
Freedman, et al., "High-Dose Therapy and autologous Bone Marrow Transplantation in Patients with Follicular Lymphoma During First Remission," Blood, 1996, vol. 88, No. 7, pp. 2780-2786.
Gallmeier, et al., "Inhibition of Ataxia Telangiectasia- and Rad3-Related Function Abrogates the In Vitro and In Vivo Tumorigencity of Human Colon Cancer Cells Through Depletion of CD133+ Tumor-Initiating Cell Fraction," Stem Cells, 2011, 39:418-429.
Grossbard, et al., "Clinical Status and Optimal Use of Rituximab for B-Cell Lymphomas," Published on Psychiatric Times, www.psychiatrictimes.com, Review Article, Dec. 1, 1998, pp. 1-3.
Hainsworth, et al., "Maximizing Therapeutic Benefit of Rituximab: Maintenance Therapy Versus Re-Treatment at Progression in Patients with Indolent Non-Hodgkin's Lymphoma—A Randomized Phase II Trial of the Minnie Pearl Cancer Research Network," Journal of Clinical Oncology, 2005, vol. 23, No. 6, pp. 1088-1095.
Hall, et al., "Mechanisms of Action of, and Modes of Resistance to, Alkylating Agents Used in the Treatment of Hematological Malignancies," Blood Reviews, 1992, No. 6, pp. 163-173.
Hiddemann, et al., "Frontline therapy with rituximab added to the combination of cyclophosphamide, doxorubicin, vincristine, and prednisone (CHOP) significantly improves the outcome for patients with advanced-stage follicular lymphoma compared with therapy

(56) References Cited

OTHER PUBLICATIONS with CHOP alone: results of a prospective randomized study of the German Low-Grade Lymphoma Study Group," Blood, 2005, vol. 106, No. 12, pp. 3725-3732.
Horning, "Natural History of and Therapy for Indolent Non-Hodgkin's Lymphomas," Seminars in Oncology, 1993, vol. 20, No. 5, Suppl. 5, pp. 75-88.
Horning, et al., "The natural history of initially untreated low-grade non-Hodgkin's lymphomas," N Engl J. Med, 1984, 311(23):1471-1475.
Houts, et al., "Nonmedical Costs to Patients and Their Families Associated with Outpatient Chemotherapy," Cancer 1984, 54:2388-2392.
Howard, et al., "Rituximab and CHOP Induction Therapy for Newly Diagnosed Mantle-Cell Lymphoma: Molecular Complete Responses are not Predictive of Progression-Free Survival," Journal of Clinical Oncology, 2002, vol. 20, No. 5, pp. 1288-1294.
Intron® A, Interferon alfa-2b, recombinant for Injection, Product Information, revised Nov. 1997, pp. 137.
Jaffe, et al., "Introduction and overview of the classification of the lymphoid neoplasms," World Health Organization Classification of Tumors of Haematopoietic and Lymphoid Tissues, Swerdlow, et al., editors, 4th edition, Lyon, France 2008 pp. 158-166.
Johnson, et al., "Patterns of Survival in Patients with Recurrent Follicular Lymphoma: A 20-Year Study from a Single Center," Journal of Clinical Oncology, 1995, vol. 13, No. 1, pp. 140-147.
Jordan, et al., "Comparison of the Effects of Vinblastine, Vincristine, Vindesine, and Vinepidine on Microtubule Dynamics and Cell Proliferation in Vitro," Cancer Research, 1985, vol. 45, pp. 2741-2747.
Kola, et al., "Can the pharmaceutical industry reduce attrition rates?" Nature Review, 2004, vol. 3, pp. 711-715.
Konopleva, et al., "The anti-apoptotic genes Bcl-$X_1$ and Bcl-2 are over-expressed and contribute to chemoresistance of non-proliferating leukemic $CD34^+$ cells," British Journal of Haematology, 2002, 118, pp. 521-534.
Koo, et al., "Methylation-dependent loss of RIP3 expression in cancer represses programmed necrosis in response to chemotherapeutics," Cell Research, 2015, 25-707-725.
Lepage, et al., "Treatment of Low-Grade Non-Hodgkin's Lymphomas: Assessment of Doxorubicin in a Controlled Trial," Hematological Oncology, 1990, vol. 8, pp. 31-39.
Litman, et al., "The multidrug-resistant phenotype associated with overexpression of the new ABC half-transporter, MXR (ABCG2)," Journal of Cell Science, 2000, No. 113, pp. 2011-2021.
Luce, et al., "Combined Cyclophosphamide, Vincristine, and Prednisone Therapy of Malignant Lymphoma," Cancer, 1971, vol. 28, No. 2, pp. 306-317.
Macedo, et al., "Standard CHOP with Reduced Dose of Doxorubicin (mini-CHOP) for Elderly Patients with Intermediate and High Grade Non-Hodgkin's Lymphoma (NHL)," Blood, 1994, 84 (10 Suppl. 1):644a, pp. 1-3.
Madjd, et al., "CD44+ cancer cells express higher levels of the anti-apoptotic protein Bcl-2 in breast tumours," Cancer Immunity, 2009, vol. 9, pp. 1-7.
Maloney, et al., "A Phase II Trial of CHOP Followed by Rituximab Chimeric Monoclonal Anti-CD20 Antibody for Treatment of Newly Diagnosed Follicular Non-Hodgkin's Lymphoma: SWOG 9800," Blood, Annual Meeting Program and Abstracts Issue, Dec. 7-11, 2001, 43rd Annual Meeting, vol. 98, No. 11, abstract #3502, pp. 1-3.
Marcus, et al., "Phase III Study of R-CVP Compared with Cyclophosphamide, Vincristine, and Prednisone Alone in Patients with Previously Untreated Advanced Follicular Lymphoma," Journal of Clinical Oncology, 2008, vol. 26, No. 28, pp. 4579-4586.
McKelvey, et al., "Hydroxyldaunomycin (Adriamycin) Combination Chemotherapy in Malignant Lymphoma," Cancer, 1976, No. 4, pp. 1484-1493.
Miller, et al., "Initial Chemotherapy of Clinically Localized Lymphomas of Unfavorable Histology," Blood, 1983, vol. 62, No. 2, pp. 413-418.
O'Brien, et al., "The natural history of low grade non-Hodgkin's lymphoma and the impact of a no initial treatment policy on survival," Q J. Med, 1991, 80(292):651-660.
Patient Information SAKK protocol 35/98, revised Dec. 18, 1998 with English translation, pp. 1-5.
Pinter-Brown, et al., "Hodgkin and Non-Hodgkin Lymphoma," in Manual of Clinical Oncology, 6th Edition, Lippincott Williams & Wilkins publishing, Dennis A. Cascito, ed., 2009, pp. 431-470.
Portlock, et al., "No initial therapy for stage III and IV non-Hodgkin's lymphomas of favorable histologic types," Ann Intern Med, 1979, 90(1):10-13.
Price, et al., "Interferon Alfa-2b in Addition to Chlorambucil in the Treatment of Follicular Lymphoma: Preliminary Results of a Randomized Trial in Progress," Eur. J. Cancer, 1991, vol. 27, suppl 4, pp. S34-S36.
Rohatiner, et al., "A randomized controlled trial to evaluate the role of interferon as initial and maintenance therapy in patients with follicular lymphoma," British Journal of Cancer, 2001, 85(1), pp. 29-35.
Schmitz, et al., "Clonal selection of CD20-negative non-Hodgkin's lymphoma cells after treatment with anti-CD20 antibody rituximab," Br J Haematol, 1999, 106:571-572.
Sreerma, et al., "Cellular Levels of Class 1 and Class 3 Aldehyde Dehydrogenases and Certain Other Drug-metabolizing Enzymes in Human Breast Malignancies," Clinical Cancer Research, 1997, vol. 3, pp. 1901-1914.
Swenson, et al., "Improved survival of follicular lymphoma patients in the United States," J. Clin Oncol, 2005, 23(22): 5019-5026.
US FDA Guidelines for "Clinical Pharmacology Section of Labeling for Human Prescription Drug and Biological Products—Content and Format," Dec. 2006 Labeling, pp. 1-19.
US FDA Regulations of 2006 (21 CFR Ch. I (Apr. 1, 2006 Edition)), pp. 8-90.
Van Oers, "Rituximab maintenance therapy: a step forward in follicular lymphoma," Haematologica, 2007, 92:826-833.
Van Oers, et al., "Chimeric anti-CD20 monoclonal antibody (MabThera) in remission induction and maintenance treatment of relapsed follicular non-Hodgkin's lymphoma: a phase III randomised clinical trial," Intergroup Collaborative Study (EORTC 20981), Aug. 17, 1998, pp. 1-68.
Van Oers, et al., "Rituximab Maintenance Treatment of Relapsed/Resistant Follicular Non-Hodgkin's Lymphoma: Long-Term Outcome of the EORTC 20981 Phase III Randomized Intergroup Study," Journal of Clinical Oncology, 2010, vol. 28, No. 17, pp. 2853-2858.
Venkatesha, et al., "Sensitization of Pancreatic Cancer Stem Cells to Gemcitabine by Chk1 Inhibition," NeoPlasia, 2012, vol. 14, No. 6, pp. 519-525.
Weiner, "Rituximab: mechanism of action," Semin Hematol., 2010, 47(2), pp. 115-123.
Young, et al., "The treatment of indolent lymphomas: watchful waiting v aggressive combined modality treatment," Semin Hematol, 1988, 25 (2 Suppl 2): 11-16.

\* cited by examiner

```
SEQUENCE LISTING

<160> NUMBER OF SEQ ID NOS: 2

<210> SEQ ID NO 1
<211> LENGTH: 106
<212> TYPE: PRT
<213> ORGANISM: Mus musculus

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 2
<211> LENGTH: 121
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
```

```
                    20                  25                  30
Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
 65              70                  75                  80

Met Gln Leu Ser Ser Leu Thr Ser Glu Asp Ser Ala Val Tyr Tyr Cys
            85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120
```

COMBINATION THERAPIES FOR B-CELL LYMPHOMAS COMPRISING ADMINISTRATION OF ANTI-CD20 ANTIBODY

CROSS-REFERENCE TO RELATED APPLICATIONS

This application is a divisional of U.S. application Ser. No. 13/524,837, filed Jun. 15, 2012, which is a divisional of U.S. application Ser. No. 11/840,956, filed Aug. 18, 2007 (now U.S. Pat. No. 8,329,172 issued Dec. 11, 2012), which is a continuation of U.S. application Ser. No. 10/196,732, filed Jul. 17, 2002 (now abandoned), which is a continuation of U.S. application Ser. No. 09/372,202, filed Aug. 11, 1999 (now U.S. Pat. No. 6,455,043 issued Sep. 24, 2002) which claims priority under 35 U.S.C. Section 119(e) and the benefit of U.S. Provisional Application No. 60/096,180 filed Aug. 11, 1998, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 4, 2014, is named GNE0375R1C2D2D1US.txt and is 2,517 bytes in size.

FIELD OF THE INVENTION

The invention relates to the use of anti-CD20 antibodies or fragments thereof in the treatment of B-cell lymphomas, particularly the use of such antibodies and fragments in combined therapeutic regimens.

BACKGROUND OF THE INVENTION

The use of antibodies to the CD20 antigen as diagnostic and/or therapeutic agents for B-cell lymphoma has previously been reported. CD20 is a useful marker or target for B-cell lymphomas as this antigen is expressed at very high densities on the surface of malignant B-cells, i.e., B-cells wherein unabated proliferation can lead to B-cell lymphomas.

CD20 or Bp35 is a B-lymphocyte-restricted differentiation antigen that is expressed during early pre-B-cell development and remains until plasma cell differentiation. It is believed by some that the CD20 molecule may regulate a step in the B-cell activation process which is required for cell cycle initiation and differentiation. Moreover, as noted, CD20 is usually expressed at very high levels on neoplastic ("tumor") B-cells. The CD20 antigen is appealing for targeted therapy, because it does not shed, modulate, or internalize.

Previous reported therapies involving anti-CD20 antibodies have involved the administration of a therapeutic anti-CD20 antibody either alone or in conjunction with a second radiolabeled anti-CD20 antibody, or a chemotherapeutic agent.

In fact, the Food and Drug Administration has approved the therapeutic use of one such anti-CD20 antibody, RITUXAN®, for use in relapsed and previously treated low-grade non-Hodgkin's lymphoma (NHL). Also, the use of RITUXAN® in combination with a radiolabeled murine anti-CD20 antibody has been suggested for the treatment of B-cell lymphoma.

However, while anti-CD20 antibodies and, in particular, RITUXAN® (U.S.; in Britain, MABTHERA®; in general Rituximab), have been reported to be effective for treatment of B-cell lymphomas, such as non-Hodgkin's lymphoma, the treated patients are often subject to disease relapse. Therefore, it would be beneficial if more effective treatment regimens could be developed. More specifically, it would be advantageous if anti-CD20 antibodies had a beneficial effect in combination with other lymphoma treatments, and if new combined therapeutic regimens could be developed to lessen the likelihood or frequency of relapse. Also, it would be helpful if current treatment protocols for B-cell lymphoma were improved whereby patients with lymphomas which are refractory to other treatment methods could be treated with chimeric or radiolabeled anti-CD20 antibodies. It would also be helpful if treatment with anti-CD20 antibodies, particularly in combination with other treatments, could be used as therapy for other types of lymphoma besides low grade, follicular non-Hodgkin's lymphoma (NHL).

SUMMARY OF THE INVENTION

The present invention discloses combined therapeutic treatments for B-cell lymphomas, and reports the benefits of treating relapsed or refractory B-cell lymphomas with chimeric and radiolabeled anti-CD20 antibodies. In particular, it has been found that treatment with anti-CD20 antibody provides a beneficial synergistic effect when administered in combination with cytokines, radiotherapy, myeloablative therapy, or chemotherapy. Surprisingly, patients who had prior bone marrow or stem cell transplantation had an unexpected increase in the over-all response rate when compared with patients with no prior therapy.

DETAILED DESCRIPTION OF THE INVENTION

Figure 1:
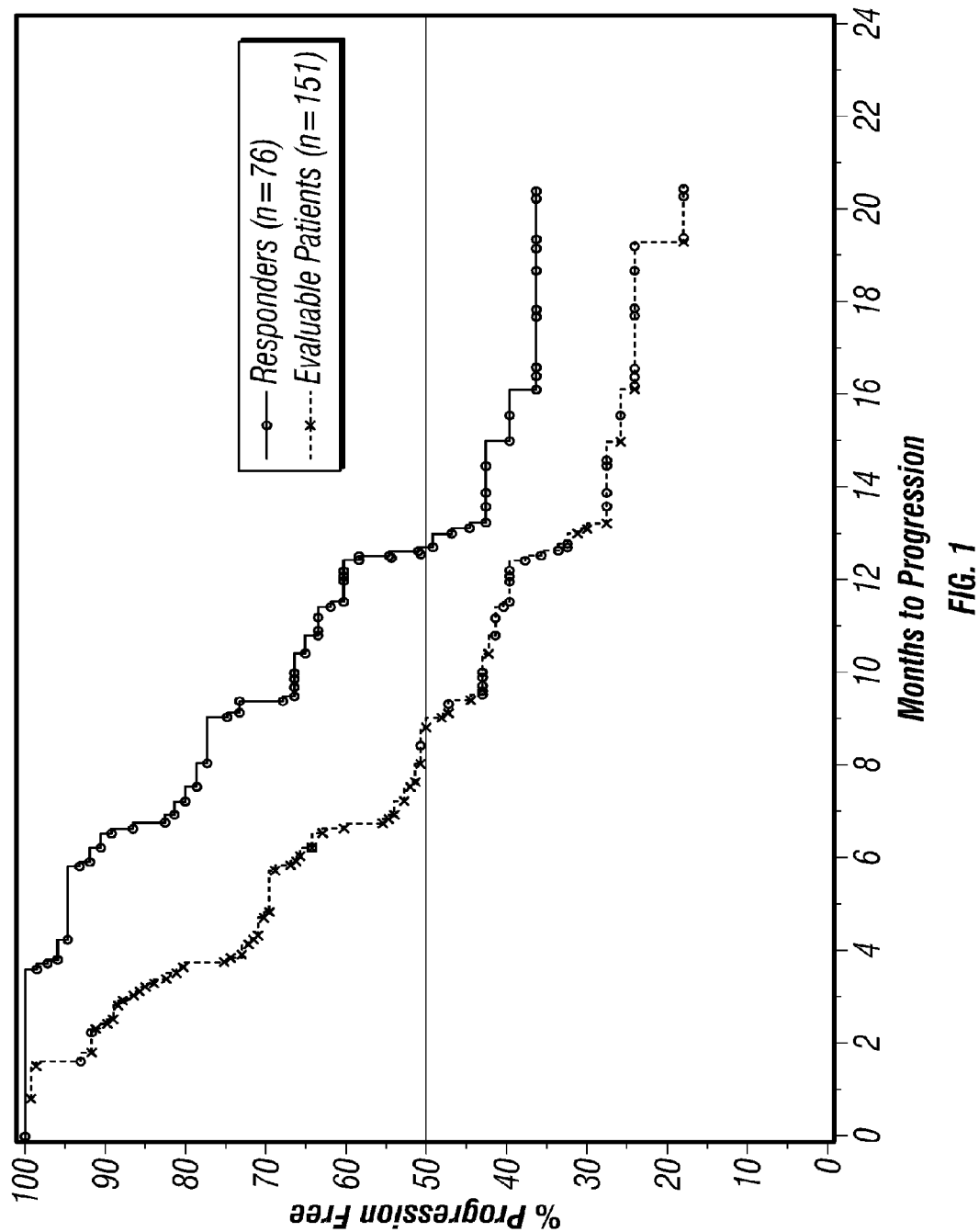
FIG. 1: Time to progression (TTP) for all 151 assessable patients and TTP for 76 responders (CR or PR). Kaplan-Meier projected overall median TTP is 9.0 months (95% confidence interval [CI], 6.7 to 11.4); projected TTP for responders is 12.5 months (95% CI, 11.0 to 16.0).

This invention encompasses combined therapeutic regimens for the treatment of B-cell lymphomas. In general, such methods include a method for treating relapsed B-cell lymphoma, where a patient having prior treatment for lymphoma has relapsed and is administered a therapeutically effective amount of a chimeric anti-CD20 antibody. Such prior treatments can include, for example, previous treatment with anti-CD20 antibodies, treatments which included a bone marrow or stem cell transplantation, radiotherapy and chemotherapy. The previous chemotherapy may be selected from a wide group of chemotherapeutic agents and combination regimens, including CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also included in the methods of the invention are methods for treating a subject having B-cell lymphoma wherein the subject is refractory for other therapeutic treatments, including all those listed above, i.e., treatment with chimeric anti-CD20 antibody, treatments which included a bone marrow or stem cell transplantation, radiotherapy and chemotherapy. In particular, encompassed are methods of treating a patient who has not exhibited appreciable tumor remission or regression after administration of a chimeric anti-CD20 antibody, comprising administering to said patient a radiolabeled anti-CD20 antibody.

In particular, the methods of treating a patient with a radiolabeled antibody after a chimeric antibody are performed whereby the radiolabeled anti-CD20 antibody is administered from about one week to about two years after said administration of said chimeric anti-CD20 antibody. More particularly, the radiolabeled anti-CD20 antibody is administered from about one week to about nine months after said administration of said chimeric anti-CD20 antibody.

While any anti-CD20 antibodies can be used for the methods of the present invention, a preferred chimeric antibody is C2B8 (IDEC Pharmaceuticals, Rituximab). A preferred radiolabeled antibody is Y2B8, which is a murine antibody labeled with yttrium-90 ($^{90}Y$). However, antibodies with other radiolabels may be used, particularly those labeled with a beta or alpha isotope. Anti-CD19 antibodies may also be used.

One of skill in the art would know the parameters for choosing a particular type of anti-CD20 antibody. For instance, chimeric and humanized antibodies are beneficial for decreased immunogenicity, and for facilitating antibody effector mediated immune reactions via the human constant region domains. Murine and other mammalian antibodies, in contrast, are beneficial for delivering a radiolabel to the tumor cell, as such antibodies generally have a decreased half-life in vivo.

Antibody treatments performed initially to which patients are refractory or have relapsed may include initial treatments with chimeric antibodies or mammalian antibodies. Also encompassed are initial treatments with other antibodies, including anti-CD19 antibodies and anti-Lym antibodies, and treatments with antibodies labeled with cytotoxic moieties, such as toxins, and radiolabels, e.g., ONCOLYM® (Techniclone) or BEXXAR® (Coulter).

It should be clear that the combined therapeutic regimens of the present invention can be performed whereby said therapies are given simultaneously, i.e., the anti-CD20 antibody is administered concurrently or within the same time frame (i.e., the therapies are going on concurrently, but the agents are not administered precisely at the same time). The anti-CD20 antibodies of the present invention may also be administered prior to or subsequent to the other therapies. Sequential administration may be performed regardless of whether the patient responds to the first therapy to decrease the possibility of remission or relapse.

The combined therapies of the present invention include a method for treating B-cell lymphoma comprising administering at least one chimeric anti-CD20 antibody and at least one cytokine. In particular, the invention includes a method for treating B-cell lymphoma comprising administering a synergistic therapeutic combination comprising at least one anti-CD20 antibody and at least one cytokine, wherein the therapeutic effect is better than the additive effects of either therapy administered alone. Preferred cytokines are selected from the group consisting of alpha interferon, gamma interferon, IL-2, GM-CSF and G-CSF. Again, the anti-CD20 antibody and the cytokine(s) may be administered sequentially, in either order, or in combination.

Also included in the present invention is a method for treating B-cell lymphoma comprising administering to a patient a therapeutically effective amount of a chimeric anti-CD20 antibody before, during or subsequent to a chemotherapeutic regimen. Such a chemotherapy regimen may be selected from the group consisting of, at the very least, CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also encompassed are methods for treating B-cell lymphoma comprising administering to a patient a therapeutically effective amount of a chimeric anti-CD20 antibody before, during or subsequent to a bone marrow or peripheral stem cell transplant. Such bone marrow transplant may also be accompanied by other therapeutic regimens such as chemotherapy. The antibodies of the present invention may also be used in a method of reducing residual CD20+ tumor cells in bone marrow or stem cells before or after myeloablative therapy by administering to a patient a chimeric anti-CD20 antibody. It may also be possible to use such antibodies in vitro to induce apoptosis of tumor cells and reduce or cure bone marrow or stem cell preparations of residual tumor cells before they are infused back into the patient.

It should be understood that stem cell transplants may be allogeneic or autologous. If the transplant is allogeneic, i.e., from another person, the disclosed therapeutic regimens may include treatments with immunosuppressive drugs before administration of the anti-CD20 antibodies. Coadministration of other drugs designed to enhance acceptance of the transplant and stimulate the production and differentiation of immune cells is also contemplated. For instance, it has been shown that administration of GM-CSF to marrow transplant recipients promotes the development of specific bone marrow cells which in turn produces circulating infection-fighting neutrophils, and increased the survival rate of marrow transplant recipients.

The methods of the present invention may be used to treat a variety of B-cell lymphomas, including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention.

For instance, a recent classification system proposed by European and American pathologists is called the Revised European American Lymphoma (REAL) Classification. This classification system recognizes Mantle cell lymphoma and Marginal cell lymphoma among other peripheral B-cell neoplasms, and separates some classifications into grades based on cytology, i.e., small cell, mixed small and large, large cell. It will be understood that all such classified lymphomas may benefit from the combined therapies of the present invention.

The U.S. National Cancer Institute (NCI) has in turn divided some of the REAL classes into more clinically useful "indolent" or "aggressive" lymphoma designations. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. These lymphomas may also benefit from the combined therapeutic regimens of the present invention.

Non-Hodgkin's lymphoma has also been classified on the basis of "grade" based on other disease characteristics including low-grade, intermediate-grade and high-grade lymphomas. Low-grade lymphoma usually presents as a nodal disease, and is often indolent or slow-growing. Intermediate- and high-grade disease usually presents as a much more aggressive disease with large extranodal bulky tumors. Intermediate- and high-grade disease, as well as low grade NHL, may benefit from the combined therapeutic regimens of the present invention.

The Ann Arbor classification system is also commonly used for patients with NHL. In this system, stages I, II, III, and IV of adult NHL can be classified into A and B categories depending on whether the patient has well-defined generalized symptoms (B) or not (A). The B designation is given to patients with the following symptoms: unexplained loss of more than 10% body weight in the 6 months prior to diagnosis, unexplained fever with temperatures above 38° C. and drenching night sweats. Occasionally, specialized staging systems are used:

Stage I—involvement of a single lymph node region or localized involvement of a single extralymphatic organ or site.
Stage II—involvement of two or more lymph node regions on the same side of the diaphragm or localized involvement of a single associated extralymphatic organ or site and its regional lymph nodes with or without other lymph node regions on the same side of the diaphragm.
Stage III—involvement of lymph node regions on both sides of the diaphragm, possibly accompanying localized involvement of an extralymphatic organ or site, involvement of the spleen, or both.
Stage IV—disseminated (multifocal) involvement of 1 or more extralymphatic sites with or without associated lymph node involvement or isolated extralymphatic organ involvement with distant (non-regional) nodal involvement.
For further details, see The International Non-Hodgkin's Lymphoma Prognostic Factors Project: A predictive model for aggressive non-Hodgkin's lymphoma. *New Eng. J. Med.* 329(14): 987-994 (1993).

Preferred antibodies, dosage regimens and particular combinations of therapy will now be illustrated by way of the following exemplary data.

Rituximab and Y2B8

Non-Hodgkin's lymphoma (NHL) affects approximately 250,000 people in the United States. The majority of patients with NHL are not cured by chemotherapy, radiotherapy, or high-dose treatment with autologous bone marrow (ABMT) or peripheral blood stem cell (PBSC) support.

Approximately 80% of non-Hodgkin's lymphomas are B-cell malignancies and >95% of these express the CD20 antigen on the cell surface. This antigen is an attractive target for immunotherapy because it is found exclusively on B-cells, and not on hematopoietic stem cells, pro-B-cells, normal plasma cells, or other normal tissues. It is not shed from the cell surface and does not modulate upon antibody binding (1).

Rituximab is one of a new generation of monoclonal antibodies developed to overcome limitations encountered with murine antibodies, including short half-life, limited ability to stimulate human effector functions, and immunogenicity (2, 3).

Rituximab is a genetically engineered monoclonal antibody with murine light- and heavy-chain variable regions (SEQ ID NOs: 1 and 2, respectively) and human gamma I heavy-chain and kappa light-chain constant regions. The chimeric antibody is composed of two heavy chains of 451 amino acids and two light chains of 213 amino acids and has an approximate molecular weight of 145 kD. Rituximab is more effective than its murine parent in fixing complement and mediating ADCC, and it mediates CDC in the presence of human complement (4). The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner (5). In humans, the half-life of the antibody is approximately 60 hours after the first infusion and increases with each dose to 174 hours after the fourth infusion. The immunogenicity of the antibody is low; of 355 patients in seven clinical studies, only three (<1%) had a detectable anti-chimeric antibody (HACA) response.

Rituximab was genetically engineered using the murine 2B8 antibody. The 2B8 antibody has also been conjugated to different radiolabels for diagnostic and therapeutic purposes. To this end, copending application Serial Nos. 08/475,813 (now U.S. Pat. No. 6,682,734); Ser. No. 08/475,815 (now U.S. Pat. No. 6,399,061) and Ser. No. 08/478,967 (now U.S. Pat. No. 5,843,439), all herein incorporated by reference in their entirety, disclose radiolabeled anti-CD20 conjugates for diagnostic "imaging" of B-cell lymphoma tumors before administration of therapeutic antibody. "In2B8" conjugate comprises a murine monoclonal antibody, 2B8, specific to human CD20 antigen, that is attached to Indium[111] ($^{111}$In) via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. Nos. 08/475,813, 08/475,815 and 08/478,967 (now U.S. Pat. No. 6,682,734; 6,399,061; and. 5,843,439, respectively) was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in application Ser. Nos. 08/475,813, 08/475,815 and 08/478,967 (now U.S. Pat. Nos. 6,682,734; 6,399,061; and 5,843,439, respectively) are radiolabeled therapeutic antibodies for the targeting and destruction of B-cell lymphomas and tumor cells. In particular, the Y2B8 conjugate comprises the same anti-human CD20 murine monoclonal antibody, 2B8, attached to yttrium-[90] ($^{90}$Y) via the same bifunctional chelator. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Because the $^{90}$Y radionuclide was attached to the 2B8 antibody using the same bifunctional chelator molecule MX-DTPA, the Y2B8 conjugate possesses the same advantages discussed above, e.g., increased retention of radionuclide at a target site (tumor). However, unlike $^{111}$In, it cannot be used for imaging purposes due to the lack of gamma radiation associated therewith. Thus, a diagnostic "imaging" radionuclide, such as $^{111}$In, can be used for determining the location and relative size of a tumor prior to and/or following administration of therapeutic chimeric or $^{90}$Y-labeled antibodies in the combined regimens of the invention. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}$I, $^{125}$I, $^{123}$I, $^{99}$Tc, $^{67}$Ga, as well as $^{111}$In. Antibodies have also been labeled with a variety of radionuclides for potential use in targeted immunotherapy (Peirersz et al. (1987). The use of monoclonal antibody conjugates for the diagnosis and treatment of cancer. *Immunol. Cell Biol.* 65: 111-125). These radionuclides include $^{188}$Re and $^{186}$Re as well as $^{90}$Y, and to a lesser extent $^{199}$Au and $^{67}$Cu. I-(131) has also been used for therapeutic purposes. U.S. Pat. No. 5,460,785 provides a listing of such radioisotopes and is herein incorporated by reference.

As reported in copending application Serial Nos. 08/475, 813, 08/475,815 and 08/478,967 (now U.S. Pat. Nos. 6,682, 734; 6,399,061; and 5,843,439, respectively), administration of the radiolabeled Y2B8 conjugate, as well as unlabeled chimeric anti-CD20 antibody, resulted in significant tumor reduction in mice harboring a B-cell lymphoblastic tumor. Moreover, human clinical trials reported therein showed significant B-cell depletion in lymphoma patients infused with chimeric anti-CD20 antibody. In fact, chimeric 2B8 has recently been heralded the nation's first FDA-approved anti-cancer monoclonal antibody under the name of RITUXAN®. Thus, at least one chimeric anti-CD20 antibody has been shown to demonstrate therapeutic efficacy in the treatment of B-cell lymphoma.

In addition, U.S. application Ser. No. 08/475,813 (now U.S. Pat. No. 6,682,734) herein incorporated by reference, discloses sequential administration of RITUXAN®, a chimeric anti-CD20, with both or either indium-labeled or yttrium-labeled marine monoclonal antibody. Although the radiolabeled antibodies used in these combined therapies are murine antibodies, initial treatment with chimeric anti-CD20 sufficiently depletes the B-cell population such that the HAMA response is decreased, thereby facilitating a combined therapeutic and diagnostic regimen.

Thus, in this context of combined immunotherapy, murine antibodies may find particular utility as diagnostic reagents. Moreover, it was shown in U.S. application Ser. No. 08/475, 813 (now U.S. Pat. No. 6,399,061) that a therapeutically effective dosage of the yttrium-labeled anti-CD20 antibody following administration of RITUXAN® is sufficient to (a) clear any remaining peripheral blood B-cells not cleared by the chimeric anti-CD20 antibody; (b) begin B-cell depletion from lymph nodes; or (c) begin B-cell depletion from other tissues.

Thus, conjugation of radiolabels to cancer therapeutic antibodies provides a valuable clinical tool which may be used to assess the potential therapeutic efficacy of such antibodies, create diagnostic reagents to monitor the progress of treatment, and devise additional therapeutic reagents which may be used to enhance the initial tumor killing potential of the chimeric antibody. Given the proven efficacy of an anti-CD20 antibody in the treatment of non-Hodgkin's lymphoma, and the known sensitivity of lymphocytes to radioactivity, it would be highly advantageous for such chimeric and radiolabeled therapeutic antibodies to find use in combined therapeutic regimens which decrease the frequency of relapsed or refractory non-Hodgkin's lymphoma. In addition, it would be beneficial if such combined therapeutic regimens found use in the treatment of other B-cell lymphomas.

Low-Grade or Follicular NHL
Single-Agent Studies with Relapsed or Refractory NHL FDA approval of Rituximab was based on five single-agent studies primarily in patients with low-grade or follicular NHL. An early Phase I study of single Rituximab infusions ranging from 10-500 mg/m$^2$ demonstrated that the maximum tolerated dose had not been reached; however, the length of infusion time at the highest dose was not considered feasible for outpatient therapy. The ORR in 15 patients was 13% (Table 1)(6).

TABLE 1

Rituximab: Summary of Efficacy Results

| Study Description | Indication | N* | ORR | CR | PR | Median DR (months) | Median TIP (months) | References |
|---|---|---|---|---|---|---|---|---|
| Phase I/II, Single-Dose Single Agent | Relapsed B-Cell Lymphoma | 15 | 2 (13%) | 0 (0%) | 2 (13%) | NA† | 8.1 | 6 |
| Phase I/II, Multiple-Dose Dose-Ranging | Relapsed Low-, Intermediate-, and High-Grade Lymphoma | 34 | 17 (50%) | 3 (9%) | 14 (41%) | 8.6 | 10.2 | 7 |

TABLE 1-continued

Rituximab: Summary of Efficacy Results

| Study Description | Indication | N* | ORR | CR | PR | Median DR (months) | Median TIP (months) | References |
|---|---|---|---|---|---|---|---|---|
| Phase II; Multiple-Dose Combined with CHOP | Newly Diagnosed and Relapsed Low-Grade or Follicular B-Cell Lymphoma | 38 | 38 (100%) | 22 (58%) | 16 (42%) | 35.3+ | 36.7+ | 21, 22 |
| Phase III, Multiple-Dose Single-Agent | Relapsed Low-Grade or Follicular B-Cell Lymphoma | 151 | 76 (50%) | 9 (6%) | 67 (44%) | 11.6 | 13.2 | 8, 9 |
| Phase II, Multiple-Dose Single-Agent | Relapsed Low-Grade or Follicular B-Cell Lymphoma | 35 | 21 (60%) | 5 (14%) | 16 (46%) | 13.4+ | 19.4+ | 13 |
| Phase II, Multiple-Dose, Combined with Interferon | Relapsed Low-Grade or Follicular B-Cell Lymphoma | 38 | 17 (45%) | 4 (11%) | 13 (34%) | 22.3+ | 25.2+ | 29 |
| Phase II, Multiple-Dose, Single-Agent | Relapsed Low-Grade or Follicular B-Cell Lymphoma, Bulky Disease | 28 | 12 (43%) | 1 (4%) | 11 (39%) | 5.9 | 8.1 | 14 |
| Phase II, Multiple-Dose, Single-Agent | Relapsed Low-Grade or Follicular B-Cell Lymphoma, Retreatment | 57 | 23 (40%) | 6 (11%) | 17 (29%) | 15.0+ | 16.7+ | 19, 20 |
| Phase II, Multiple-Dose Combined with CHOP Modality | Previously Untreated Intermediate- or High-Grade Lymphoma | 30 | 29 (96%) | 19 (63%) | 10 (33%) | 1 I+ | 17+ | 34 |
| Phase II, Alternative Multiple Dosing | Intermediate- or High-Grade B-Cell Lymphoma | 54 | 17 (32%) | 5 (9%) | 12 (22%) | NA† | 8.2+ | 33 |

In Phase I of a Phase I/II dose-ranging study, patients received 125-375 mg/m² administered as four weekly infusions. No dose-related toxicities were demonstrated, and 375 mg/m² was chosen as the Phase II dose. Tumor regressions were observed in 17 of 37 (46%) patients who received this dose, including 3 (8%) complete responses (CR) and 14 (38%) partial responses PR (7).

A subsequent single-arm pivotal study of Rituximab infused at 375 mg/m² weekly times four was conducted in 166 patients with relapsed or refractory, low-grade or follicular NHL (International Working Formulation [IWF] Types A-D and REAL classification, small lymphocytic lymphoma, Follicular center, follicular Grades I, II, III(8)). Patients with tumor masses >10 cm or with >5000 lymphocytes/µL in the peripheral blood were excluded from this study. The median age was 58 years (105 men and 61 women) and the median number of prior treatments was three. Bone marrow involvement was present in 56% of 149 patients evaluated. Forty-five percent had >2 extranodal sites and 41% had bulky disease (>5 cm).

Complete response required the regression of all lymph nodes to <1×1 cm² demonstrated on two occasions at least 28 days apart on neck, chest, abdomen, and pelvic CT scans, resolution of all symptoms and signs of lymphoma, and normalization of bone marrow, liver, and spleen. Partial response required a >50% decrease in the sum of the products of perpendicular measurements of lesions without any evidence of progressive disease for at least 28 days. Patients who did not achieve a CR or PR were considered non-responders, even if a net decrease (>50%) of measurable disease was observed. Time to progression was measured from the first infusion until progression.

Rituximab Chimeric Anti-CD20 Monoclonal Antibody Therapy for Relapsed Indolent Lymphoma: Half of Patients Respond to a Four-Dose Treatment Program Purpose: The CD20 antigen is expressed on more than 90% of B-cell lymphomas. It is appealing for targeted therapy, because it does not shed or modulate. A chimeric monoclonal antibody more effectively mediates host effector functions and is itself less immunogenic than are murine antibodies.

Patients and Methods: This was a multiinstitutional trial of the chimeric anti-CD20 antibody, IDEC-C2B8. Patients with relapsed low grade or follicular lymphoma received an outpatient treatment course of IDEC-C2B8 375 mg/m² intravenously weekly for four doses.

Results: From 31 centers, 166 patients were entered. Of this intent-to-treat group, 48% responded. With a median follow-up duration of 11.8 months, the projected median time to progression for responders is 13.0 months. Serum antibody levels were sustained longer after the fourth infusion than after the first, and were higher in responders and in patients with lower tumor burden. The majority of adverse events occurred during the first infusion and were grade 1 or 2; fever and chills were the most common events. Only 12% of patients had grade 3 and 3% grade 4 toxicities. A human antichimeric antibody was detected in only one patient.

Conclusion: The response rate of 48% with IDEC-C2B8 is comparable to results with single-agent cytotoxic chemotherapy. Toxicity was mild. Attention needs to be paid to the rate of antibody infusion, with titration according to toxicity. Further investigation of this agent is warranted, including its use in conjunction with standard chemotherapy.

Approximately 80% of malignant lymphomas are of B-cell origin. (Aisenberg A C: Coherent view of non-Hodgkin's lymphoma. *J Clin Oncol* 13:2656-2675, 1995.) Virtually all patients with low grade or follicular histology will eventually relapse after treatment with currently available standard therapies (Gallagher C J, et al., Follicular lymphoma: Prognostic factors for response and survival. *J Clin Oncol* 4:1470-1480, 1986), as will many with more aggressive histologic categories (Armitage J D: Treatment of non-Hodgkin's lymphoma. *N. Engl J Med* 328:1023-1030 1993). Those who relapse need alternative therapeutic approaches.

The cell-surface antigen CD20 is expressed on more than 90% of B-cell lymphomas and chronic lymphocytic leukemias, and on 50% of pre-B-cell acute lymphocytic leukemia (Stashenko P. et al: Characterization of a human B lymphocyte-specific antigen. *J Immunol* 125:1678-1685, 1980; Anderson K C et al.: Expression of human B cell-associated antigens on leukemias an lymphomas: A model of human B cell differentiation. *Blood* 63:1424-1433, 1984; Zhou L-J, Tedder T F: CD20 Workshop Panel Report, in Schlosspam S F, Boumsell L, Gilks W, et al (eds): Leukocyte Typing V. White Cell Differentiation Antigens, Oxford, United Kingdom, Oxford University, 1995, pp. 511-514). It is expressed on normal B cells from the pre-B-cell stage to the activated B-cell stage, but is not expressed on stem cells, plasma cells, or cells of other lineages (Zhou L-J, et al. supra). It is a transmembrane protein that appears to act as a calcium channel and to play an important role in cell-cycle progression and differentiation (Einfeld D A et al: Molecular cloning of the human B cell CD20 receptor predicts a hydophobic protein with multiple transmembrane domains. *EMBO J* 7:711-717, 1988; Tedder T F, Engel P: CD20: A regulator of cell-cycle progression of B lymphocytes. *Immunol Today* 15:450-454, 1994). Monoclonal antibodies that target the CD20 antigen have been developed, both for diagnostic and therapeutic purposes (Stashenko et al, supra; Press O W et al.: Monoclonal Antibody 1F5 (anti-CD20) serotherapy of human B cell lymphomas. *Blood* 69:584-591, 1987; Kaminski M S et al: Radioimmunotherapy of B-cell lyphoma with [$^{131}$I]anti-B1 (anti-CD20) antibody. *N Engl. J Med* 329:459-465, 1993; Press O W, et al: Radiolabeled antibody therapy of B-cell lymphoma with autologous bone marrow support. *N Engl J. Med* 329:1219-1224, 1993; Knox S J, et al: Yttrium-90-labeled anti-CD20 monoclonal antibody therapy of recurrent B-cell lymphoma. *Clin Cancer Res* 2:457-470, 1996). The CD20 antigen is appealing for targeted therapy, because it does not shed, modulate, or internalize (Einfeld et al, supra).

Therapeutic monoclonal antibodies can be used as a delivery system (eg, for a radioisotope (Press et al, supra) or a toxin (Grossbard M L, et al: Monoclonal antibody-based therapies of leukemia and lymphoma. *Blood* 80:863-878, 1992) or as the actual therapeutic modality. For therapy with an unconjugated antibody, a chimeric (predominantly human) antibody is desirable for the following reasons: (1) the human constant regions mediate normal host effector functional; (2) it has a longer half-life than do murine antibodies; and (3) there is a lower probability of developing a host antibody to the chimeric monoclonal antibody (Liu A Y, et al: Production of a mouse-human chimeric monoclonal antibody to CD20 with potent Fc-dependent biologic activity. *J Immunol* 139:3521-3526, 1987; LoBuglio A F, et al: Mouse/human chimeric monoclonal antibody in man: Kinetics and immune response. *Proc Natl Acad Sci USA* 86:4220-4224, 1989; Mueller B M, et al: Enhancement of antibody-dependent cytotoxicity with a chimeric antiGD2 antibody. *J Immunol* 144:1382-1386, 1990).

The chimeric human-mouse anti-CD20 monoclonal antibody, Rituximab (IDEC-C2B8; IDEC Pharmaceuticals Corp. San Diego, Calif.), is a human immunoglobulin (Ig) G1 kappa antibody, with mouse variable region isolated from a murine anti-CD20 monoclonal antibody, IDEC-2B8 (Reff M E et al: Depletion of B cells in vivo by a chimeric mouse human monoclonal antibody to CD20. *Blood* 83:435-445, 1994). A single-dose phase I trial demonstrated both biologic efficacy in terms of transient B-cell depletion and a good safety profile (Maloney D G et al: Phase I clinical trial using escalating single-dose infusion of chimeric anti-CD20 monoclonal antibody (IDEC-C2B8) in patients with recurrent B-cell lymphoma. *Blood* 84:2457-2466, 1994). Subsequently, a multiple-dose schedule was shown to be feasible and to achieve a 50% response rate in a cohort of 34 patients with relapsed low grade lymphoma (Maloney D G et al: IDEC-C2B8 (Rituximab) anti-CD20 antibody therapy in patients with relapsed low-grade non-Hodgkin's lymphoma. *Blood* 90:2188-2195, 1997).

The current report summarizes results of a multiinstitutional trial of a four-dose course of therapy with this chimeric anti-CD20 antibody.

Patients and Methods

Eligibility

Adult patients with relapsed low grade or follicular B-cell lymphoma, histologically confirmed and positive for CD20, were eligible. Patients with chronic lymphocytic leukemia (lymphocytes $>5\times10^9$/L) were excluded. Patients had to have either not responded to primary therapy or relapsed (not more than four times), have progressive measurable disease, and sign an institutional review board-approved informed consent. They had to be at least 3 weeks beyond prior standard therapy including corticosteroids, and have recovered from significant toxicities from prior therapies. Patients had to have good performance status (Zubrod 0 to 2) and adequate hematologic, renal, and hepatic function. Patients were excluded if they had lesions >10 cm in diameter, CNS lymphoma, AIDS-related lymphoma, pleural effusions or ascites secondary to lymphoma, active opportunistic infection, serious nonmalignant disease, prior investigational therapies including prior anti-CD20 therapy, or recent major surgery.

Therapy

The antibody dose was 375 mg/m$^2$, administered intravenously once weekly for a total of four infusions (days 1, 8, 15, and 22) on an outpatient basis. IDEC-C2B8 was produced and supplied by IDEC Pharmaceuticals Corp. The drug was reconstituted in normal saline to a concentration of 1 mg/mL and given through a 0.22-μm in-line filter. Oral premedication with acetaminophen or diphenhydramine was permitted; corticosteroids were prohibited. The initial infusion rate was 50 mg/h, with subsequent infusion rate increase if no toxicity was seen. Guidelines were specified for interruption of infusion, with resumption once adverse events subsided.

Monitoring

To measure all sites of disease, baseline evaluation included documentation of disease-related signs and symptoms, physical examination, bilateral bone marrow biopsies, and radiographic studies, which included chest x-ray and computed tomography (CT) or magnetic resonance imaging of the neck, chest, abdomen, and pelvis. Laboratory testing included routine hematology, serum chemistries, lymphocyte subset measurement, Igs, serum complement (C3), $\beta_2$-microglobulin, and urinalysis.

Patients were screened for serum anti-CD20 antibody (human antichimeric antibody [HACA] using a sandwich enzyme-linked immunoadsorbent assay (ELISA). Peripheral blood and bone marrow were studied by the polymerase chain reaction (PCR) for bcl-2 gene rearrangement using previously described methodology (Gribben et al: Detection of residual lymphoma cell by polymerase chain reaction in peripheral blood is significantly less predictive for relapse than detection in bone marrow. *Blood* 83:3800-3807, 1994).

Monitoring included frequent hematology and serum chemistry profiles, periodic monitoring of immunoglobulins and lymphocyte subsets, and full tumor restaging evaluations at months 1 and 3 following the fourth infusion, then every 3 months for 2 years, and every 6 months thereafter in responders.

Pharmacokinetic monitoring used microtiter plates coated with polyclonal goat anti-IDEC-C2B8 antibody, to which patient serum was added. The goat anti-C2B8 was produced by immunizing a goat with IDEC-C2B8. The serum was than purified over a human IgG column to remove the antihuman component and was then run over an IDEC-C2B8 column and eluted. The resulting purified antibodies are specific for the C2B8 (idiotype) portion of IDEC-C2B8. Goat antihuman IgG conjugated with horseradish peroxidase was used as a detector. Serum samples were obtained from all patients: before and immediately after the last antibody dose. Additional serum samples were drawn from 14 patients at 24, 48, 72, and 96 hours after the first and fourth infusions. Pharmacokinetic analysis used data for all samples that had detectable antibody (≥0.5 µg/mL). Levels for the first and fourth infusions were analyzed separately for each patient to assess clearance rates, using the PCNONLIN version 4.0 pharmacokinetic software (SCI Software, Lexington, Ky.).

Definition of End Points

Complete response (CR) required the resolution of all symptoms and signs of lymphoma, including bone marrow clearing, for at least 28 days. Partial response (PR) required a ≥50% decrease in the sum of the products of perpendicular measurements of lesions, without any evidence of progressive disease for at least 28 days. Patients who did not achieve a CR or PR were considered nonresponders, even if there was a net decrease (<50%) of measurable disease. Time to progression was measured from the first infusion until progression.

An independent panel of nine radiologists and lymphoma specialists reviewed and verified all CT scans of patients who exhibited a >40% reduction in tumor size as measured by the investigator. This refereed response designation (Horning et al: Response criteria and quality assurance of response in the evaluation of new therapies for patients with low-grade lymphoma. *Proc Am Soc Clin Oncol* 16:18a, 1997 (abstr)) is the one used for this report.

Statistical Methods

Time to progression was analyzed by the Kaplan-Meier method (Kaplan E L et al., Non-parametric estimation from incomplete observations. *J Am Stat Assoc* 53: 457-481, 1958.) Comparisons of clinical response data by individual prognostic variables were performed using Fisher's exact test. Comparison of serum concentration data by clinical response was performed using the Wilcoxon rank-sum test. Kaplan-Meier curves were generated using PROC LIFETEST (SAS/STATS Users Guide, Version 6, SAS Institute, Cary, N.C.). A stepwise logistic regression analysis was performed to identify the most relevant prognostic factors to clinical response (SAS: SAS/STAT User's Guide, Version 6. Cary, N.C., SAS Institute, 1990.)

Results

Patient Features

The 166 patients were enrolled at 31 centers in the United States and Canada between April 1995 and March 1996. The median age was 58 years (range, 22 to 79). There were 105 men and 61 women. There were 33 with small lymphocytic lymphoma (SL), 67 with follicular small cleaved, 53 with follicular mixed, three with other low grade lymphoma variants, and 10 with follicular large cell (The Non-Hodgkin's Lymphoma Pathologic Classification Project: National Cancer Institute sponsored study of classifications of non-Hodgkin's lymphomas. Summary and description of a working formulation for clinical usage. *Cancer* 49:2112-2135, 1982.). The median time since diagnosis was 4.1 years (range, 0.5 to 25).

Prior therapy included chemotherapy in 97%, radiotherapy in 25%, and bone marrow or peripheral-blood stem-cell transplantation regimens in 14%. The median number of prior treatments was three (range one to 10). Twenty-two patients had been resistant to all prior chemotherapy (had never achieved a CR or PR), while 45 were resistant to their most recent chemotherapy before study entry.

Response

The overall response rate for the intent-to-treat group of all 166 patients was 48%, of which 6% were CRs and the remainder PRs.

A detailed analysis of efficacy was also performed on a subset of 151 patients, excluding 15 patients for the following reasons: one never started treatment for personal reasons; eight received one or more doses of corticosteroids during the evaluation period (a protocol violation that was strictly enforced to avoid any confusion about the efficacy of the antibody); one had surgery within 4 weeks of study entry (an exclusion criterion); one lacked measurable lesions; and four did not complete all four doses because of grade 3 or 4 adverse events (they were included in the toxicity analysis).

The response rate for these 151 assessable patients was virtually identical to that of the intent-to-treat group, with a 50% response rate, including 6% CRs. Among those who did not achieve a CR or PR, the majority (56 of 75) nonetheless had a net decrease of measurable disease (mean decrease, 32%). With a median follow-up duration of 11.8 months, the projected median time to progression for responders is 13.0 months for the intent-to-treat group and 12.5 months for the assessable group (FIG. 1); 53 of 76 responders have not yet relapsed. To date, only nine patients have died, all of progressive lymphoma.

Table 1 lists response according to clinical features. Significantly lower response rates were noted for patients with the following: SL lymphoma compared with other cell types; positive bone marrow; ≥two extranodal sites; and, among the subset of 118 patients with follicular lymphomas, those without detectable bcl-2 gene rearrangement by PCR in the peripheral blood or bone marrow. Unexpectedly, the 23 patients whose prior therapy had included high-dose regimens with stem-cell or bone marrow transplantation had a significantly higher response rate than those who had not received transplant regimens (78% v 43%, P<0.01). Patients who had achieved a CR or PR with their last prior chemotherapy course had a nonsignificant but somewhat better response to the antibody than those who were resistant to chemotherapy (53% v 36%, P=0.06). Notable pretreatment features that did not have a significant impact on response in the univariate analysis were elevated lactate dehydrogenase (LDH) level, $\beta_2$-microglobulin, bulky disease, and older age.

By logistic regression analysis (Table 2), SL histologic type, resistance to the last course of chemotherapy, and baseline peripheral-blood bcl-2 negativity by PCR emerged as factors that were significantly correlated with lower response to treatment with IDEC-C2B8.

TABLE 1

Patient Features and Response

| Feature | No. of Patients | % CR + PR | P |
|---|---|---|---|
| All patients | 166 | 48 | — |
| Assessable patients* | 151 | 50 | — |
| Age ≥ 60 years | 67 | 51 | NS |
| Sex: male | 95 | 48 | NS |

TABLE 1-continued

Patient Features and Response

| Feature | No. of Patients | % CR + PR | P |
|---|---|---|---|
| Histology | | | |
| Small lymphocytic | 30 | 13 | <.01† |
| Follicular small cleaved | 60 | 60 | |
| Follicular mixed | 48 | 60 | |
| Follicular large cell | 10 | 60 | |
| Other ‡ | 3 | 33 | |
| Elevated LDH§ | 46 | 43 | NS |
| Elevated $\beta_2$- microglobulin§ | 41 | 56 | NS |
| Bulk§ | | | |
| <5 cm | 88 | 56 | NS |
| >5 cm | 61 | 43 | |
| Marrow§ | | | |
| Negative | 66 | 61 | .03 |
| Positive | 83 | 42 | |
| bcl-2 in peripheral blood¶ | | | |
| Negative | 62 | 52 | .04 |
| Positive | 55 | 71 | |
| bcl-2 in bone marrow¶ | | | |
| Negative | 60 | 52 | .05 |
| Positive | 52 | 71 | |
| >2 extranodal site | 75 | 39 | .01 |

Abbreviations:
LDH, lactate dehydrogenase;
NS, not significant.
*Subset analyses conducted on the assessable group of 151 patients (see text); results for the intent-to-treat group were virtually identical.
†Comparison of SL versus follicular histologies.
‡One each with: mucosa-associated lymphoid tissue (MALT); low-grade B-cell lymphoma, not otherwise specified; and marginal-zone lymphoma.
§Data available for LDH on 143, $\beta_2$-microglobulin on 148, bulk on 149, and marrow status on 149.
¶For follicular lymphoma only.

TABLE 2

Prognostic Factors for Clinical Response: Stepwise Logistic Regression Analysis

| Prognostic Factor* | $\chi^2$ | P |
|---|---|---|
| Histological type (FSC, FM, FL v SL) | 22.29 | <.001 |
| bcl-2 at baseline (peripheral blood) (positive v negative by PCR) | 5.55 | .018 |
| Resistance to last chemotherapy (no v yes)† | 5.12 | .024 |
| Bulky disease (less v more) | 2.49 | .115 |
| ABMT history (yes v no) | 2.73 | .098 |
| Age (younger v older) | 1.43 | .232 |

Abbreviations:
FSC, follicular small cleaved;
FM, follicular mixed;
FLC, follicular large cell;
ABMT, autologous bone marrow transplant.
*Favorable feature listed first.
†Resistance = failure to achieve CR or PR.

Adverse Events

Figure 2:
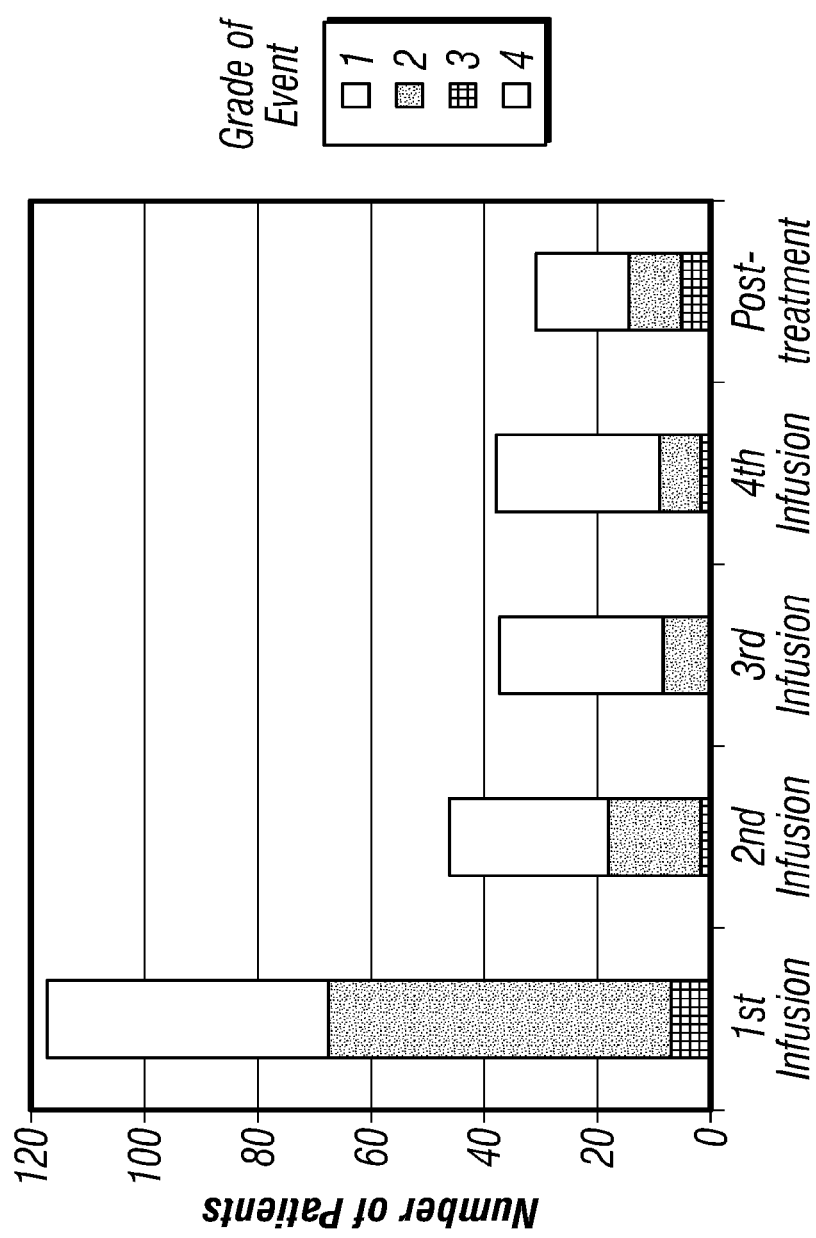
FIG. 2: Adverse events attributed to antibody, or cause unknown, stratified by infusion number. As depicted by solid and white shading, 96% of events were grade 1 or 2.

Adverse events generally occurred during therapy or within the first 30 days following therapy (Table 3). The majority were observed during the first infusion (FIG. 2) and were grade 1 or 2. After the first infusion, most patients (55%) had no toxicity for the remainder of treatment.

Adverse events were typically brief. The median duration of nausea was 1 hour, fever 3 hours, bronchospasm less than 30 minutes, hypotension 1.6 hours, and rash and pruritus 2 hours. The antibody infusion rate was titrated according to adverse events. The mean duration of the first dose was 5.2 hours (range, 2.5 to 20); 33% of patients had interruptions. During the second, third, and fourth doses, the frequency of interruptions decreased to 6%, 2%, and 1%, respectively, and the mean durations of the infusions were 3.5, 3.3, and 3.3 hours, respectively.

TABLE 3

Adverse Events During Therapy

| | NCI Grade | | | % of |
|---|---|---|---|---|
| Event | 1-2 | 3 | 4 | Patients |
| Any | 599 | 18 | 2 | 84 |
| General | | | | |
| Fever | 84 | — | — | 43 |
| Chills | 51 | 2 | — | 28 |
| Headache | 26 | 1 | — | 14 |
| Asthenia | 25 | — | — | 13 |
| Pain | 22 | — | — | 11 |
| Pruritus | 21 | 1 | — | 13 |
| Rash | 16 | — | — | 10 |
| Urticaria | 9 | 1 | — | 6 |
| Angioedema | 27 | 1 | — | 14 |
| Dizziness | 11 | — | — | 6 |
| Digestive | | | | |
| Nausea | 34 | 1 | — | 18 |
| Vomiting | 13 | 1 | — | 8 |
| Diarrhea | 10 | — | — | 4 |
| Respiratory | | | | |
| Bronchospasm | 15 | 1 | — | 8 |
| Dyspnea | 1 | 1 | — | 1 |
| Rhinitis | 14 | 1 | — | 7 |
| Cough increase | 4 | 1 | — | 3 |
| Cardiovascular | | | | |
| Hypotension | 18 | 1 | — | 10 |
| Arrhythmia | 5 | 2 | 1 | 2 |
| Hematologic | | | | |
| Anemia | 1 | 1 | — | 1 |
| Thrombocytopenia | 5 | 1 | — | 3 |
| Leukopenia | 12 | 1 | — | 7 |
| Neutropenia | 6 | — | 1 | 4 |

NOTE.
Includes all grade 3 or 4 events that were considered related to the antibody, and most frequent (>10 occurrences) other events, for all patients (N = 165 since 1 patient withdrew before receiving any antibody).
"During Therapy" includes from day 1 to 30 days after the fourth infusion; for later events, see text.
Abbreviation:
NCI, National Cancer Institute.

Thirteen patients had hemoglobin levels decrease to as low as 8 to 10 g/dL, and four had levels of 7.6 to 7.9; recovery occurred in a median of 7 days. Three patients with pretreatment platelet counts of 76,000 to 85,000×10⁹/L had counts decrease to 63,000 to 72,000 at a median of 19 days, with recovery by a median of 7 days; one patient with a pretreatment platelet count of 90,000 had a count of 27,000 at day 23, with recovery to 86,000 in 6 days. Fourteen patients had granulocytes decrease to a level of 1 to 1.5× 10⁹/L at median of 41 days, with recovery by a median of 8 days; two patients had granulocytes decrease to 0.5 to 0.9 at day 9 and day 23, with recovery to greater than 2.0 by 6 to 7 days; one had a granulocyte count of 0.1 at day 51, with recovery by 4 days. The remainder of patients, 86% of the population, had no cytopenias. Thus, the median (±SE) values for hemoglobin, platelets, leukocytes, and granulocytes remained within normal limits throughout the treatment period.

Infections that occurred either during therapy or for up to a year thereafter were predominantly bacterial (37 of 68), and the vast majority were minor (61 of 68 grade 1 or 2;

none grade 4). The respiratory tract was the source in 19 and the urinary tract in three; gastroenteritis occurred in three. There were three episodes of bacteremia, one with *Listeria* detected before the third infusion, one staphylococcal, and one polymicrobial, which was felt to be catheter-related; all resolved with antibiotics. Viral infections included herpes simplex in 10 and herpes zoster in five.

After therapy and during the first year of follow-up evaluation, a total of 98 related adverse events were reported in 45 patients, of which 81% were grade 1 or 2. The most common late (from 31 days to 1 year after the last antibody infusion) adverse events were hematologic: 13 neutropenia (five grade 3, one grade 4), 10 leukopenia (one grade 3, no grade 4), and one RBC aplasia.

Monitoring of B-Cell and Immunologic Parameters

Figure 3:
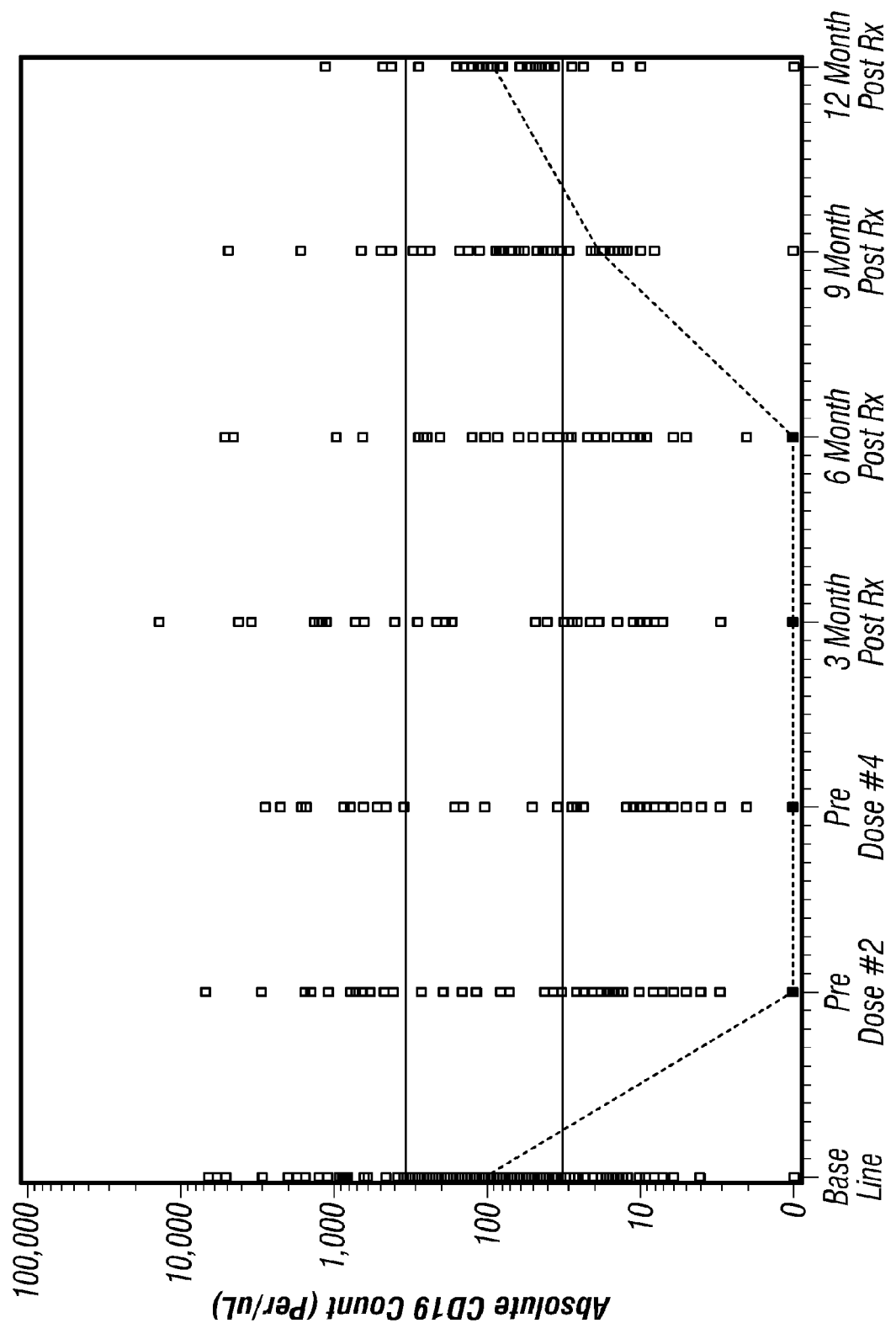
FIG. 3: Median CD19$^+$ lymphocyte counts ( . . . ) were depleted after 1 antibody infusion and recovered by 9 to 12 months. A minority of patients (n=16) did not deplete circulating B cells. These were predominantly SL patients (n=13) and nonresponders (n=15).

The median absolute B-cell count in peripheral blood at baseline was 97.5 cells/mL (normal range, 32 to 341). As illustrated in FIG. 3, the median B-cell count declined with treatment, to undetectable levels after the first dose for the majority. A minority of patients (n=16) did not deplete circulating B cells. These were predominantly SL patients (n=13) and nonresponders (n=15). Recovery of B cells started between 6 and 9 months, with recovery to normal between 9 and 12 months.

Mean serum IgG and IgA levels remainder within normal limits throughout the study. The mean serum IgM level had decreased to 41.5 mg/dL (normal range, 45 to 145 mg/dL) at 6 months posttreatment and had recovered to 65.1 mg/dL at the 8-month follow-up point. Twenty-three patients had reductions in Ig levels by ≥50% to subnormal levels.

HACA was detected in only one patient, at day 50, and was not associated with any clinical or laboratory abnormalities.

Median absolute T-cell counts in peripheral blood, using CD3, CD4, and CD8, as well as natural-killer cell counts, remained stable throughout the study. A >20% decrease from baseline in serum complement (C3) was noted in 18 patients.

Cells with bcl-2 gene rearrangement were detected pretreatment by PCR in the peripheral blood of 55 patients and in the bone marrow of 52 patients. For those who had serial monitoring, reversion to negative status (no detectable rearranged cells by PCR) occurred in the peripheral blood in 19% following the first infusion (10 of 52 patients). 50% (26 of 52) before the fourth infusion, and 62% (26 of 45) by 3 months. In the bone marrow, reversion to negative was seen in 56% (nine of 16) at 3 months.

Pharmacokinetics

Figure 4A:
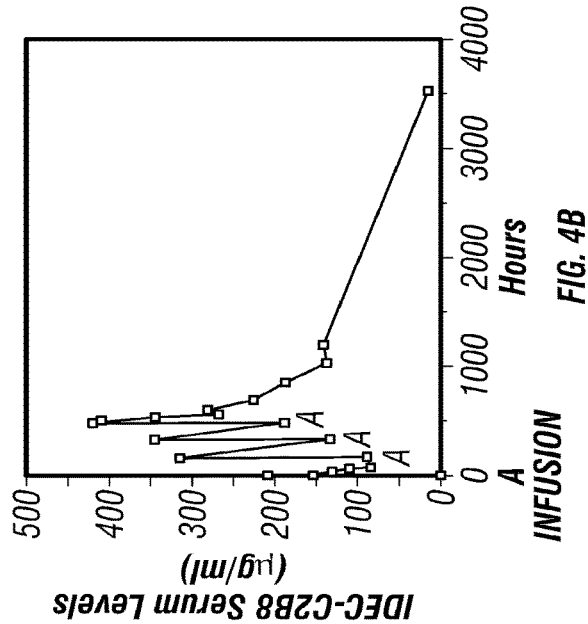
FIGS. 4A, 4B, 4C: Patients with (A) complete response (CR) or (B) partial response (PR) show accumulation of antibody, whereas (C) nonresponder shows rapid clearance.
Figure 4B:
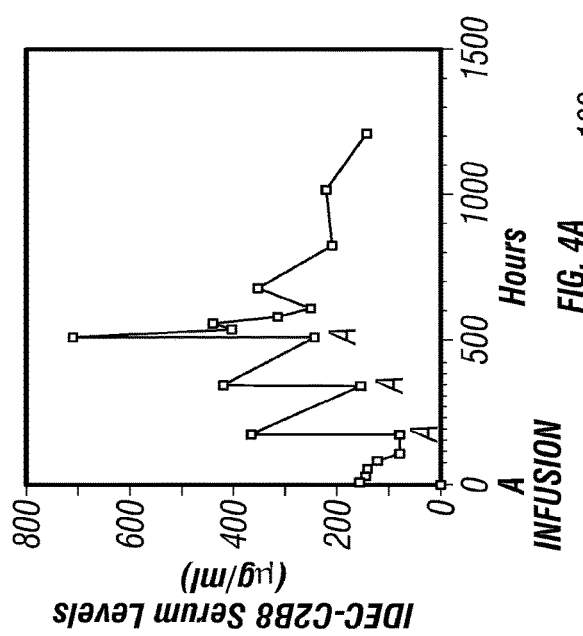
Figure 4C:
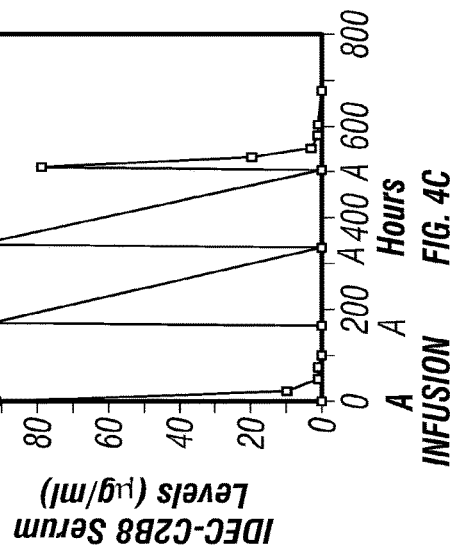

Median serum antibody levels were higher for responders than nonresponders (Table 4 and FIG. 4). Attainable serum antibody concentrations correlated negatively with the number of circulating B cells, with the size of the largest measurable tumor pretreatment, and with the baseline sum of the products of the diameters of the six largest lesions. Serum levels were significantly lower in patients with SL than other histologic types at the following time points: before the second and fourth infusions; and at 1 week, 1 month, and 3 months posttreatment.

For patients who has detailed pharmacokinetic monitoring, the mean serum half-life after the first infusion was 76.3 hours (range, 31.5 to 152.6), while after the fourth infusion it was 205.8 hours (range, 83.9 to 407.0). The maximum observed concentration was higher after the fourth than after the first infusion (mean, 464.7 v 205.6 μg/mL, respectively), the clearance was slower (0.0092 v 0.0382 L/h), and the area under the curve was greater (86,125 v 16,320 μg-h/mL). A significant correlation was found between the number of circulating B cells at baseline and rapidity of antibody clearance after the first infusion (P=0.01).

Discussion

The response rate was 50% with this outpatient four-dose course of therapy with IDEC-C2B8 for patients with relapsed low grade or follicular lymphoma. Most of the responses were partial (6% complete), which is typical of single-agent therapy in the setting of relapsed lymphoma. These results are comparable to some of the most encouraging recent chemotherapy results for relapsed indolent lymphoma, such as with fludarabine or 2-chlorodeoxyadenosine (Pott-Hoeck C. et al., Purine analogs in the treatment of low-grade lymphomas and chronic lymphocytic leukemias. *Ann Oncol* 6: 421-433, 1995; Piro L D, Cladribine in the treatment of low-grade non-Hodgkin's lymphoma. *Semin Hematol* 33: 34-39, 1996 (suppl 1); McLaughlin P et al., Fludarabine phosphate in lymphoma: an important new therapeutic agent in Cabanillas F, Rodriguez, M A (eds): *Advances in Lymphoma Research*, Boston, Mass., Kluwer Academic, 1996, pp 3-14.)

Earlier experiences with unconjugated murine monoclonal antibodies noted a low percentage of brief responses, and identified several problems, including rapid antibody clearance, the development of a human antimouse antibody (HAMA) response, (Nadler et al., Serotherapy of a patient with a monoclonal antibody directed against a human lymphoma-associated antigen. Cancer Res 40:3147-3154, 1980) and antigenic modulation (Ritz J et al., Serotherapy of acute lymphoblastic leukemia with monoclonal antibody. *Blood* 58: 141-152, 1981; Foon K A et al., Effects of monoclonal antibody therapy in patients with chronic lymphocytic leukemia. *Blood* 64: 1085-1093, 1984; Dillman R O et al., Therapy of chronic lymphocytic leukemia and cutaneous T-cell lymphoma with T101 monoclonal antibody. *J Clin Oncol* 2: 881-891, 1984.) The use of a chimeric (predominantly human) antibody and the targeting of a surface antigen that does not shed or modulate are key innovations that contributed to the success of the current trial. Murine anti-CD20 antibodies have been used in other successful monoclonal antibody trials, especially recent radioimmunotherapy (RIT) trials with iodine 131 and yttrium 90 (Kaminski M S et al. supra; Press O W et al, supra; Knox S J et al., supra.) Unlike the current trial, RIT programs using $^{131}$I involve the additional complexities of patient isolation and radiation safety precautions, as well as, in the myeloablative Seattle approach, (Press O W et al., supra) the need for bone marrow or peripheral-blood stem-cell transplantation.

The toxicity of the current program was notably mild, particularly with respect to myelosuppressive toxicities that are typical of standard chemotherapy or RIT. Adverse events occurred mainly with the first infusion, in a constellation that typically included modest (grade 1 or 2) and brief (minutes to hours) fever, chills, and aches. By the second and subsequent infusions, the majority of patients experienced no further infusion-related toxicities. By virtue of the modest toxicities of this agent, which do not overlap with the toxicities of standard chemotherapy, this agent lends itself to integration with chemotherapy programs. There is already some early experience with this antibody in conjunction with chemotherapy with cyclophosphamide, doxorubicin, vincristine, and prednisone (CHOP); the toxicity of CHOP plus Rituximab appeared comparable to that of CHOP alone, so the combination seems feasible. The response rate (73% CRs and 27% PRs) (Czuczman M S et al., Chemoimmunotherapy of low-grade lymphoma with the anti-CD20 antibody IDEC-C2B8 in combination with CHOP chemotherapy. *Cancer Invest* 14:59-61, 1996 (suppl 1)) was respectable, although in the range of what might be achieved with CHOP alone. Further experience with chemotherapy plus Rituximab programs seems warranted.

Only one patient in this trial developed an antichimeric antibody response. Even though chimeric antibodies have murine variable regions, it appears from this trial and others (Clendeninn N J et al., Phase I/II trials of CAMPATH-1H, a humanized anti-lymphocyte monoclonal antibody, in non-Hodgkin's lymphoma and chronic lymphocytic leukemia. *Blood* 80: 158a, 1992 (suppl 1, abstr)) that chimeric or humanized antibodies largely circumvent the problem of HAMA. Since this agent depletes normal B cells, it is al notable that the infections that occurred in this trial were both modest and fairly ordinary, in contrast to the experience with the CAMPATH-1H antibody, which depletes both B and T cells and was associated with a substantial number of opportunistic infections. (Poynton C H et al., Adverse reactions to Campath-1H monoclonal antibody. *Lancet* 341: 1037, 1993 (letter))

The high response rate with this antibody was encouraging, including its efficacy in patients with adverse prognostic features, such as high LDH or $\beta$2-microglobulin levels, and in patients who often tolerate standard therapies poorly, such as the elderly and those who had undergone prior marrow transplantation. Observations in patient subsets with low response rates were also informative. A rapid clearance of the antibody, which may be related, in part, to high tumor burden ("antigen sink"), correlated with a lower response rate. Conceivably, higher doses or more protracted dosing schedules might overcome this problem. The lower response rate with SL lymphoma, compared with follicular lymphoma, may relate to the lower density of CD20 antigen expression on SL cells. (Almasri N M et al., Reduced expression of CD20 antigen as a characteristic marker for chronic lymphocytic leukemia. *Am J Hematol* 40:259-263, 1992) However, patients with SL in this trial also typically had higher circulating B-cells counts and consequently a more rapid clearance of the agent than other patients, so the lower response rate in SL lymphoma may also be related to their lower measurable antibody levels.

It appears paradoxical that bone marrow involvement had an overall correlation with lower response rate, yet bone marrow bcl-2 positivity correlated with a higher response rate. This is partly explained by the lower response rate in SL patients, many of whom had marrow involvement but were bcl-2-negative. There is also come evidence that, among follicular lymphoma patients, those without detectable MBR or mcr bcl-2 gene rearrangement may be less responsive to chemotherapy. (López-Guillermo A et al., The molecular breakpoint site of bcl-2 gene has prognostic importance in indolent follicular lymphoma. *Blood* 88: 293a, 1996 (suppl 1, abstr)). Breakpoint-site analysis was not performed in the current trial.

Many additional issues about this agent remain to be explored. Based on early evidence of synergism between this agent and some chemotherapeutic agents (Demidem A et al., Chimeric anti-CD20 antibody (IDEC-C2B8) is apoptotic and sensitizes drug resistant human B cell lymphomas and AIDS related lymphomas to the cytotoxic effect of CDDP, VP-16 and toxins. *FASEB J* 9:A206, 1995 (abstr)) more investigation of combination therapy is planned. With its established efficacy in the setting of measurable disease, the use of this agent in a minimal or subclinical disease setting is a consideration; for such use, an unconjugated antibody such as this one (or an immunotoxin) may be preferable to the RIT approach because of concerns with RIT of toxicity to the mechanisms of action of this agent is needed. Besides its mediation of complement fixation and antibody-dependent cell-mediated cytotoxicity, there is evidence that the CD20 antigen-antibody interaction induces intracellular signaling that can affect cell-cycle entry and proliferation (Tedder T F et al., supra; Maloney D G et al., The anti-tumor effect of monoclonal anti-CD20 antibody therapy includes direct anti-proliferation activity and induction of apoptosis in CD20 positive non-Hodgkin's lymphoma cell lines. *Blood* 88:637a, 1996 (suppl 1, abstr)). On the basis of the 50% response rate in this trial, using this well tolerated, outpatient treatment schedule that is completed in 22 days, further trials with this agent are warranted.

The overall response rate (ORR) was 48% with a 6% CR and a 42% PR rate (8). The median time to progression (TTP) for responders was 13.2 months and the median duration of response (DR) was 11.6 months. Twenty-two of 80 (28%) responders remain in ongoing remission at 20.9+ to 32.9+ months (9).

Administration of Rituximab resulted in a rapid and sustained depletion of B-cells. Circulating B-cells were depleted within the first three doses with sustained depletion for up to six to nine months post-treatment in 83% of patients. Median B-cell levels returned to normal by 12 months following treatment. Although median NK cell counts remained unchanged, a positive correlation was observed between higher absolute NK cell counts at baseline and response to Rituximab (10).

Several baseline prognostic factors were analyzed to determine their correlation to response. Significantly, in 23 patients relapsed after ABMT or PBSC, the ORR was 78% versus 43% in patients who did not undergo prior high-dose therapy (p<0.01). In a multivariate analysis, the ORR was higher in patients with follicular NHL as compared with small lymphocytic lymphoma (58% vs. 12%, p<0.01), and higher in patients with chemosensitive relapse as compared with chemoresistant relapse (53% vs. 36%, p=0.06). No effect on response rate was associated with: age >60 years, extranodal disease, prior anthracycline therapy, or bone marrow involvement.

A statistically significant correlation was found between the median serum antibody concentration and response at multiple time points during treatment and follow up (11).

Serum levels of antibody were higher in patients with follicular NHL compared with small lymphocytic lymphoma. Mean serum antibody was also inversely correlated with measurements of tumor bulk and with the number of circulating B-cells at baseline. The association of lower serum antibody concentrations with higher numbers of circulating NHL cells and with higher tumor bulk suggest that the main mode of antibody clearance is to tumor cells. The association of high serum antibody concentrations with response and lower tumor bulk or circulating cells suggests that higher or more doses of Rituximab may be necessary to induce responses in some subsets of patients, such as those with bulky disease.

Nevertheless, responses were seen with Rituximab in 43% of patients with tumors >5 cm and in 35% of patients with tumors >7 cm, suggesting that treatment of patients with bulky disease with Rituximab is feasible. This is surprising considering it was long thought that antibody therapy is not conducive to treating bulky disease due to the compact nature of the tumors.

In a study conducted in Japan (12), patients with relapsed B-cell lymphoma were treated with either 250 mg/m$^2$ (N=4) or 375 mg/m$^2$ (N=8) of Rituximab weekly times four. Of 11 evaluable patients, 8 had follicular NHL, 2 had diffuse large-cell NHL, and one had mantle-cell lymphoma. Two of the 11 had a CR and 5 had a PR for an ORR of 64%; all responders had follicular histology.

Because Rituximab serum levels and response were positively correlated in previous studies, a Phase II study of eight weekly doses of 375 mg/m² Rituximab was conducted in low-grade or follicular NHL patients. The ORR was 60% in evaluable patients, with a 14% CR and a 46% PR rate. Median values for TTP in responders and DR were 13.4+ months and 19.4+ months, respectively (13). Though it is difficult to compare across studies, it appears that TTP and DR may be improved by using more doses.

Contrary to early assumptions about antibody therapy being useful only in micrometastatic disease, Rituximab is quite active in high bulk disease. In a separate study, 31 patients with relapsed or refractory, bulky low-grade NHL (single lesion of >10 cm in diameter) received 375 mg/m² Rituximab as four weekly infusions. Twelve of 28 evaluable patients (43%) demonstrated a CR (1, 4%) or PR (11, 39%)(14).

Waldenstrom's Macroglobulinemia

Waldenstrom's Macroglobulinemia (WM) is a malignancy wherein B lymphocytes secrete excessive amounts of IgM antibodies. WM usually occurs in people over sixty, but has been detected in adults in their early thirties. WM therapy is considered a rare incurable indolent malignancy, which has in the past been treated by plasmaphoresis to reduce serum viscosity. Chemotherapeutic drugs such as an alkylating agent and a corticosteroid are often prescribed. The most recommended drug for WM has been Leustatin (2CdA).

A report on seven patients with Waldenstrom's macroglobulinemia where the patients were treated with Rituximab (375 mg/m² weekly times 4) (15) noted responses in 4 (57%) of patients. Median progression-free survival was 8 months (range 3-27+ months). Thus, Rituximab should be useful in combined therapeutic protocols, particularly with chemotherapeutic reagents such as 2CdA.

Chronic Lymphocytic Leukemia (CLL)

CLL is the liquid (leukemic) equivalent of small lymphocytic lymphoma (SLL). Patients with SLL had lower serum levels and a lower response rate when treated with the standard dose of Rituximab than patients with other low-grade NHL subtypes. This is probably due to the very high levels of circulating tumor cells in patients with CLL, and because malignant cells involved in CLL are thought to have reduced levels of expression of CD20 on the cell surface.

Nevertheless, the present inventors have discovered that hematologic malignancies such as CLL may be treated with Rituximab. A recent clinical study evaluated treatment of CLL patients at higher doses of Rituximab (16). All patients receive a first dose of 375 mg/m³ to minimize infusion-relapsed side effects. Subsequent weekly dosages (3) remained the same but were given at an increased dose level. Sixteen patients have been treated at dosages of 500-1500 mg/m³. Medium age was 66 years (range, 25-78). Eighty-one percent had end-stage III-IV disease. Medium white blood cell count was $40 \times 10^9$/L (range, 4-200), Hgb 11.6 g/dl (range, 7.7-14.7), platelets $75 \times 10^9$/L, (range, 16-160), median $\beta_2$ immunoglobulin was 4.5 mg/L (range, 3.1-9.2). Median numbers of prior therapies was 2.5 (range 1-9). Sixty percent of patients were refractory to treatment. Two patients developed severe hypertension with the first dose (375 mg/m²); another one received further therapy. Toxicity at subsequent escalated dosages has been mild although no patient at the 1500 mg/m² dose level has been fully evaluated. Eight patients have completed therapy (4 at 500 mg/m², 3 at 650 mg/m², 1 at 825 mg/m²). One patient treated at 560 mg/m² achieved full remission. One patient has progressive lymphocytosis on treatment and all other patients had reduction in peripheral blood lymphocytosis but less effect on lymph nodes. Dose escalation studies are ongoing.

Another approach to improving response in CLL patients is to upregulate the CD20 antigen using cytokines. In an in vitro study, mononuclear cells from CLL patients were incubated for 24 hours with various cytokines. Flow cytometry results showed significant up-regulation by IL-4, GM-CSF, and TNF-alpha (17). In fact, recent data suggests that the upregulation of CD20 observed on CLL cells may be limited to tumor cells (Venogopal et al. Poster-PanPacific Lymphoma meeting, June 1999. Cytokine-induced upregulation of CD20 antigen expression in chronic lymphocytic leukemia (CLL) cells may be limited to tumor cells). Preliminary data also suggest that interferon alpha also upregulates CD20 on CLL cells after only 24 hours when applied at a concentration of 500 to 1000 U/ml.

Thus, by administering certain cytokines to CLL patients prior to or concurrently with administration of Rituximab, the expression of CD20 on the surface of malignant B-cells may be upregulated, thereby rendering CD20, as well as other cell surface markers such as CD19, a more attractive target for immunotherapy. A collaborative study has been initiated to test for optimal cytokine doses for CD20 upregulation in vivo. The study protocol involves treating ten patients initially with GM-CSF at 250 mcg/m² SQ QD×3, ten patients with IL-4 mcg/kg SQ QD×3, and ten patients with G-CSF at 5 mcg/kg SQ QD×3. Mononuclear cells will be separated by Ficon Hypaque centrifugation for apoptotic studies to determine if upregulation of CD20 translates to enhanced killing of tumor cells by Rituximab.

Antibody treatment of CLL can be combined with other conventional chemotherapeutic treatments known to be useful for the treatment of CLL. The most frequently used single agent for CLL is chlorambucil (LEUKERAN®), given either as 0.1 mg/kg daily or 0.4 to 1.0 mg/kg every 4 weeks. Chlorambucil is often combined with oral prednisone (30 to 100 mg/m²/d), which is useful in the management of autoimmune cytopenias. Cyclophosphamide is an alternative to chlorambucil, the usual dose being 1-2 g/m² every 3-4 weeks together with vincristine and steroids (e.g., COP regimen).

Various drug combinations have been used for CLL, including COP (cyclophosphamide, ONCOVIN®, and prednisone), and CHOP (these three drugs plus doxorubicin). Fludarabine has shown an effect in the treatment of CLL, and gave an ORR of 50% in a group of patients treated with 25-30 mg/m²/d every 3-4 weeks. http://www.cancernetwork.com. Although some patients have been shown to be refractory for fludarabine. Such patients may also be resistant to 2-CdA because often, patients who are refractory to fludarabine are also refractory to 2-CDA (O'Brien et al. *N. Engl. J. Med.* 330: 319-322 (1994)).

Hence, anti-CD20 antibody therapy will be particularly useful for patients who are refractory or who have relapsed after treatment with chemotherapeutic drugs. Rituximab therapy may also be combined with radiotherapy in these patients. TBI with a low fraction size of 15 cGy to total doses of 75 to 150 cGy has been shown to be effective in about one-third of patients.

A Phase II trial is currently being conducted by CALGB in CLL patients. Rituximab and fludarabine are administered concurrently, followed by Rituximab consolidation versus fludarabine induction followed by Rituximab.

Rituximab with Myeloablative Therapy

Myeloablative therapy has yielded responses in indolent lymphomas; however, residual tumor cells may remain despite high-dose therapy and the PBSC reinfused may contain tumor cells. Rituximab is being used before stem cell mobilization and after transplant to reduce residual CD20+ tumor cells and contamination of the bone marrow or stem cells harvested. Interim results demonstrated that no CD20+ cells were detectable in harvested cells. Eighteen of 24 patients achieved engraftment and the treatment was well tolerated. PCR testing is ongoing to evaluate residual tumor cells (18).

Retreatment of Relapsed Low-Grade NHL with Rituximab

A trial evaluating retreatment of 53 patients who had responded to Rituximab and later relapsed has been reported (19). Seven of 56 evaluable patients (13%) obtained a CR and 16 a PR (29%), for an ORR of 42%. Four patients who had a second response received a third treatment; 3 of these responded.

After treatment with two courses of Rituximab, one patient's tumor, initially classified as follicular, small cleaved cell NHL, no longer expressed the CD20 antigen and was unresponsive to Rituximab at the time of transformation to diffuse, large-cell NHL (20).

Thus, while retreatment with Rituximab is effective for treating patients who have relapsed after prior treatment with Rituximab, there may be an increased incidence of CD20− tumor cells after secondary treatment. This observation supports the utility of the combined therapeutic treatment regimens described herein.

Combination of Rituximab and CHOP Chemotherapy for Low-Grade NHL

Chemotherapy with cyclophosphamide, doxorubicin, vincristine, and prednisone (CHOP) is an effective first-line therapy for low-grade or follicular NHL. Though initial response rates are high, relapse eventually occurs and subsequent chemotherapy regimens produce remissions with shorter durations. A Phase II trial was initiated to evaluate the combination of CHOP and Rituximab (21) in newly diagnosed and relapsed low-grade or follicular NHL because their mechanisms of action are not cross-resistant, and Rituximab is synergistic with certain cytotoxic drugs, including doxorubicin (5).

Twenty-nine of 38 patients received no prior anticancer therapy. CHOP was administered at standard doses every three weeks for six cycles with six infusions of Rituximab (375 mg/m$^2$). Rituximab infusions 1 and 2 were administered on Days 1 and 6 before the first CHOP cycle, which started on Day 8. Rituximab infusions 3 and 4 were given 2 days before the third and fifth CHOP cycles, respectively, and infusions 5 and 6 were given on Days 134 and 141, respectively, after the sixth CHOP cycle.

In this combination study, 100% of the 38 patients treated responded (CR, 58%; PR, 42%). Of 35 evaluable patients who completed treatment, there were 63% CR, and 37% PR (21). Median DR is 35.3+ months with median progression-free survival not reached after a median observation time of 36.7+ months. Twenty patients are still in remission after 36+ months to 53.4+ months (22). This DR is impressive even for first-line treatment, and 24% of this trial population had relapsed after chemotherapy.

In a study to be conducted by CALGB, 40 patients with low-grade NHL will receive Rituximab weekly times 8 and oral cyclophosphamide daily starting on Day 8. Twenty patients will receive Rituximab alone for 8 weekly doses.

A Phase III study conducted by ECOG in patients with low-grade NHL is comparing the combination of cyclophosphamide and fludarabine (Arm A) with standard CVP therapy (Arm B). In the randomization to Arm A or Arm B, patients are stratified by age, tumor burden, histology, and B symptoms. Responders in both arms will undergo a second randomization to Rituximab maintenance therapy (375 mg/m$^2$ weekly times 4 every 6 months for 2 years (Arm C) or to observation (Arm D).

Combination of Rituximab with Cytokines

Rituximab Plus Interferon Alpha

Interferon is a cytokine involved in modulating the immune system (23). Mechanisms by which interferon may increase the effectiveness of antibodies include the potentiation of antigen expression (24), increased targeting of antibodies into tumors (25, 26), and enhanced cytotoxicity of immunotoxins (27).

In a combination trial, interferon-alpha (Roferon-A), a cytokine with a single-agent clinical activity in NHL (28), and Rituximab were given to patients with relapsed low-grade or follicular NHL. Interferon-alpha (2.5 or 5 MIU) was administered subcutaneously, three times weekly for 12 weeks. Rituximab was administered by IV infusion weekly for four doses (375 mg/m$^2$) starting on the fifth week of treatment. The ORR was 45% (17/38 patients); 11% had a CR and 34% had a PR. Kaplan-Meier estimates of the median DR and TTP in responders were 22.3+ and 25.2+ months, respectively (29). Previous combination studies of interferon-alpha and chemotherapeutic regimens containing anthracyclines yielded prolonged time to progression, but did not consistently increase response or survival rates (30-32). These early results suggest that the combination of Rituximab and interferon-alpha may prolong the time to progression relative to Rituximab alone.

Rituximab Plus G-CSF

In a separate study, Rituximab and G-CSF are being evaluated in relapsed low-grade NHL. It has been demonstrated in vitro as well as in vivo in healthy volunteers that G-CSF, via its effect on myeloid precursor cells, induces FcRI-positive neutrophils that are capable of functioning as effector cells in ADCC. Therefore, a Phase II study was initiated to evaluate the toxicity and efficacy of the combined treatment.

Both in Phase I and Phase II, patients were administered a standard dose of G-CSF (5 μg/kg/day) administered for three days, starting 2 days before administration of Rituximab. Phase I consisted of a dose escalation of Rituximab (125, 250, or 375 mg/m$^2$ weekly×4). Early results in 9 patients evaluated so far yielded an ORR of 67% (44% CR, 22% PR) with minor toxicity in 8 of the 9 patients (33). The most frequent adverse events were fever (4/8 patients), rhinitis (4/8), chills (3/8) and headaches (3/8), which were comparable to the adverse events observed previously in administration of Rituximab alone. The Phase II part of the study has been initiated, which will examine the efficacy of the combination of G-CSF and 375 mg/m$^2$ Rituximab×4.

Rituximab Plus IL-2

High-dose therapy with autologous peripheral blood stem cells (PBSC) or bone marrow (BM) rescue has been used to treat NHL, however success remains limited by the high risk of relapse, which is 50-80%. In an effort to improve durable remissions post-transplant, immunotherapy including high dose and low dose therapy with IL-2 has been studied in a number of treatment centers. Such studies have suggested that IL-2 therapy does demonstrate early post-transplant anti-Tumor activity.

Initially following autologous transplant, patients display delayed immune reconstitution which potentially results in diminished immune-mediated tumor eradication (43, 44). Indeed, it has been shown that both CD4+ T cells and cytotoxic CD8+ T cells are depressed (45-49). In vitro assays have demonstrated a profound suppression of T cell cytolytic and proliferative responses as well as decreased production of IL-2 in response to mitogens and soluble antigens. However, soluble IL-2 is able to restore these immune responses suggesting that immune cells in patients after autologous transplant are capable of responding to exogenous IL-2 (47). Peripheral blood NK activity also remains lower following BMT than control values and the NK activity is also augmented by addition of exogenous IL-2 (49). These data suggest that administration of IL-2 to patients shortly after stem cell transplant may enhance immune responsiveness at a critical period when tumor burden is minimal and when immune responsiveness in the absence of IL-2 is lacking.

For instance, Caligiuru et al. have shown that IL-2 (Hoffman-LaRoche) administered at $0.45 \times 10^6$ $U/M^2/day$ by 24 hour CIV for 12 weeks was able to expand the absolute number of CD56 bright NK cells (50-52). This regimen was administered to non-transplant patients in the outpatient setting with little toxicity.

Animal models have shown that non-LAK inducing low doses of IL-2 dramatically enhances anti-tumor activity when administered with tumor-specific T effector cells (53). In addition, Soiffer et al. (54) administered low doses of IL-2 to 13 autologous BMT or T cell depleted allogeneic BMT recipients undergoing treatment for relapsed leukemia or lymphoma. Enhanced immunological responsiveness was demonstrated in the laboratory with a 5- to 40-fold increase in circulating CD56 bright CD16+ CD3− NK cells. Moreover, this low dose regimen of IL-2 resulted in augmented in vitro killing of the NK targets K562. When Soiffer et al. (55) updated the outcome of 29 allogeneic BMT patients who received low dose IL-2, they found superior survival for these patients (70%) compared to histological controls (30%, p=0.41).

Lauria et al. (56) treated 11 patients with high grade NHL at a median of 42 days after ABMT with IL-2 at a dose of $2 \times 10^6$ $IU/m^2$ god for two weeks and then $3 \times 10^6$ $IU/m^2$ twice a week for a year. Phenotypic analysis showed a persistent and significant (p=0.001) increase in the proportion and absolute number of total lymphocytes and especially of both CD16 and CD56 NK cells after 6 months of therapy. None of the patients progressed with a median follow-up of twenty-two months (range 10-42 months) after starting therapy. In addition, two patients with residual disease after ABMT, one in the liver and second in the lymph nodes, obtained a complete response after 7 and 10 months of IL-2 therapy.

Vey et al. (57) treated 25 patients with refractory or relapsed HD (11 patients) and NHL (14 patients) with low dose IL-2. 48% of the patients had resistant disease at transplant and 84% achieved CR after ABMT. IL-2 was started at a mean of 54 days after transplant and consisted of a first cycle of 5 days followed by 4 cycles of 2 days every other week. Patients received a mean of $160 \times 10^6$ $IU/m^2$ of IL-2. After a five year follow-up, the probability of survival and DFS is 72% (HD 73% and NHL 70%) and 45% (HD 36% and NHL 48%).

A group at the Fred Hutchinson Cancer Research Center (FHCRC) has recently found that low dose IL-2 therapy was well-tolerated in the outpatient setting, and that remissions in patients treated with low dose IL-2 tended to be longer than without IL-2 treatment. IL-2 therapy was associated with an increase in the number of certain populations of immune cells, including CD8+ CD69+ cells; CD16+ CD8+ cells; CD16+ CD69+ cells; CD16+ CD56+ cells; CD16+ CD122+ cells; CD16+ Dr+ cells; and CD8+CD56+ cells. There was also an increase in the expression of lytic activity against the tumor targets K562 and Daudi, with a median of 5.9-fold and 6.5-fold increase, respectively. Relapses, when they occurred, occurred at a median of 17.8 months after transplant, and therefor remissions were reported to be characteristically longer than what was historically seen in transplant recipients without IL-2 therapy.

Given the encouraging data gathered from single therapy studies with IL-2 on ABMT transplant recipients, it seemed reasonable to combine IL-2 therapy with Rituximab post transplant, given that Rituximab's biological activity appears to be mediated through ADCC and complement-mediated lytic activity. Thus, a Phase I trial has been initiated in collaboration with the FHCRC to evaluate the safety and potential efficacy of a combined therapeutic regimen.

A separate Phase II study is also being performed to evaluate the efficacy and the incidence of HACA formation in patients receiving low-dose IL-2 and Rituximab. A specific objective of this study is to assess whether ADCC is enhanced by in vivo exposure to IL-2 and whether ADCC activity correlates with clinical response. Inclusion criteria for patients are histologically confirmed stage II-IV low-grade, follicular B-cell or mantle cell lymphoma. Mantle cell lymphoma, for the purposes of this clinical study, is defined as CD5+, CD23− (if available) and/or bcl-1+ by immunohistochemistry. Patients who did not respond to or have relapsed following their first treatment with a standard therapy, i.e., chemotherapy, radiotherapy, ABMT and/or immunotherapy, are eligible.

Rituximab Plus GM-CSF for the Treatment of Relapsed Low Grade or Follicular B-Cell Lymphoma Two separate Phase II trials have also been initiated to test the efficacy of combined treatment with Rituximab and GM-CSF. One study involves 40 patients with relapsed low grade B-cell lymphoma, and comprises administering Rituximab at 375 mg/m² weekly×4 (d. 1, 8, 15, 22) and GM-CSF (LEUKINE®, Immunex) at 250 mcg sc three times weekly for 8 weeks, starting one hour before the first dose of Rituximab. This study will be used to evaluate the clinical efficacy (overall response rate (ORR), overall complete response rate, time to progression and failure-free survival) of the combined therapeutic regimen, to characterize the safety (qualitative, quantitative, duration and reversibility of adverse events) of the combined therapy, and to determine the effects of the combined therapy on relevant lymphocyte subsets and cytokines. The second study plans to also monitor immunologic parameters to assess the mechanism of killing (complement C3 and C4, CH50, flow cytometry for CD3, CD4, CD8, CD16, CD19 and CD56 and ADCC assay).

Rituximab Plus Gamma-Interferon

Gamma-interferon may also be useful in combined therapy with Rituximab for treating patients with low-grade or higher-grade lymphomas. It is has recently been found that gamma-interferon upregulates CD20 expression on multiple myeloma (MM) patient plasma cells, patient B-cells, as well as on normal donor B-cells (Treon et al., Lugano, 1999). In fact, Treon and colleagues have shown that gamma-interferon augments binding of these cells to Rituximab. Induction of CD20 expression on plasma cells occurred in a dose dependent manner, with upregulation seen with as little as 1 U/ml of interferon gamma. A plateau occurred at 100 U/ml at 48 hours. Thus, gamma-interferon may also be beneficial when administered in combination with Rituximab.

Intermediate-Grade and High-Grade NHL

Single-Agent Studies

In a study conducted in Europe and Australia, alternative dosing schedules were evaluated in 54 relapsed or refractory intermediate- or high-grade NHL patients (34). Rituximab was infused at 375 mg/m$^2$ weekly for 8 doses or at 375 mg/m$^2$ once followed by 500 mg/m$^2$ weekly for 7 doses. The ORR was 31%; (CR 9%, PR 22%) no significant difference between the dosing regimens was observed. Patients with diffuse large-cell lymphoma (N=30) had an ORR of 37% and those with mantle-cell lymphoma (N=12) had an ORR of 33%.

Combination of Rituximab and CHOP Chemotherapy

In another study, 31 patients with intermediate- or high-grade NHL (19 females, 12 males, median age 49) received Rituximab on Day 1 of each of six 21-day cycles of CHOP (35). Of 30 evaluable patients, there were 19 CR (63%) and 10 PR (33%), for an ORR of 96%. This regimen was considered well tolerated and may result in higher response rates than with Rituximab or CHOP alone.

The NCI Division of Cancer Treatment and Diagnosis is collaborating with IDEC Pharmaceuticals Corporation to explore Rituximab treatment in other indications. A Phase II trial of CHOP versus CHOP and Rituximab is being conducted by ECOG, CALGB, and SWOG in older patients (>60 years) with mixed, diffuse large cell, and immunoblastic large cell histology NHL (N=630 planned). This study includes a secondary randomization to maintenance with Rituximab versus non-maintenance.

A Phase III trial of Rituximab and CHOP in 40 patients with previously untreated mantle-cell lymphoma is also ongoing at the Dana Farber Institute. Rituximab is administered on Day 1 and CHOP is given on Days 1-3 every 21 days for 6 cycles. Accrual for this study has been completed. A Phase II trial of CHOP followed by Rituximab in newly diagnosed follicular lymphoma conducted by SWOG has also been completed. Results of these two trials are being analyzed.

A Phase II trial of CHOP and Rituximab versus CHOP alone in HIV-related NHL conducted by the AIDS Malignancy Consortium is ongoing; 120 patients are planned.

Rituximab after Myeloablative Therapy Relapse

Rituximab has shown promising early results in patients with relapsed intermediate-grade NHL after high-dose therapy with autologous PBSC support. Six of seven patients responded (1 CR and 5 PR) and one patient had stable disease; therapy was well tolerated (36).

Safety Experience

Adverse events and clinical laboratory data from 315 patients in the five single-agent U.S. studies were combined to provide a safety profile of Rituximab in patients with low-grade or follicular NHL. The majority of adverse events were infusion-related and occurred with decreasing frequency after the first infusion. The most common infusion-related events were fever (49%), chills (32%), nausea (18%), fatigue (16%), headache (14%), angioedema (13%), pruritus (10%), and occasionally, hypotension (10%) and bronchospasm (8%). During the treatment period (up to 30 days following the last dose), 10% of patients experienced Grade 3 or 4 adverse events, which were primarily infusion-related or hematologic. Thrombocytopenia (<50,000 platelets/mm$^3$) occurred in 1.3% of patients, neutropenia (<1000/mm$^3$) occurred in 1.9%, and anemia (<8 gm/dL) occurred in 1.0%. Although Rituximab induced B-cell depletion in 70%-80% of patients, abnormally decreased serum immunoglobulins were observed in a minority of patients and the incidence of infection did not appear to be increased.

Hypotension requiring interruption of the Rituximab infusion occurred in 10% of patients and was Grade 3 or 4 in 1%. Angioedema was reported in 13% of patients and was considered serious in one patient. Bronchospasm occurred in 8% of patients; 2% were treated with bronchodilators. A single report of bronchiolitis obliterans was noted. Most patients experienced no further infusion-related toxicities by the second and subsequent infusions. The percentage of patients reporting adverse events upon retreatment was similar to that reported following the first course (14).

Four patients developed arrhythmias during Rituximab infusion. One of the four discontinued treatment because of ventricular tachycardia and supraventricular tachycardias. The other three patients experienced trigeminy (N=1) and irregular pulse (N=2) and did not require discontinuation of therapy. Angina was reported during infusion and myocardial infarction occurred four days post-infusion in one subject with a prior history of myocardial infarction.

The overall incidence of adverse events and Grade 3 and 4 adverse events was higher in patients with bulky disease than in patients with non-bulky disease. The incidence of dizziness, neutropenia, thrombocytopenia, myalgia, anemia, and chest pain was higher in patients with lesions >10 cm. The incidence of Grade 3 or 4 neutropenia, anemia, hypotension, and dyspnea was also higher in patients with bulky disease compared with patients with lesions <10 cm (19).

Since FDA approval of Rituximab for treatment of relapsed or refractory low-grade or follicular NHL in 1997, an estimated 17,000 patients have been treated. In May, 1998, descriptions of eight post-marketing reports of severe infusion-related adverse events associated with the use of Rituximab that resulted in fatal outcomes were summarized. In seven of the eight fatalities, severe symptoms occurred during the first Rituximab infusion. The cause of death was not reported or remains unknown for two of the eight cases. Severe respiratory events, including hypoxia, pulmonary infiltrates, or adult respiratory distress syndrome contributed to six of the eight reported deaths. One patient had a pretreatment lymphocyte count of 600,000/mm$^3$; another, a creatinine of 8; a third, a respiratory rate of 40; and a fourth, pancytopenia. Patients with a high tumor burden or with a high number of circulating malignant cells may be at higher risk and these patients should be monitored closely throughout each infusion.

Most of the adverse events recently described were previously observed in Rituximab clinical studies. One notable exception is an infusion-related syndrome associated with rapid tumor lysis, that was reported in six patients with high numbers of circulating tumor cells (37, 38). This syndrome was characterized by fever, rigors, bronchospasm with associated hypoxemia, a rapid decline in peripheral lymphocytes, laboratory evidence of tumor destruction, and transient, severe thrombocytopenia. These patients had diagnoses of B-prolymphocytic leukemia (N=2), chronic lymphocytic leukemia (N=2), mantle-cell lymphoma (N=1), or transformed NHL (N=1); all had elevated circulating lymphocytes, bulky adenopathy, and organomegaly. Although five of these six patients required hospitalization, symptoms resolved and subsequent Rituximab treatments were well tolerated; the last patient refused further therapy and died of progressive disease two weeks later.

In a separate report of seven patients with CLL and one patient with mantle-cell lymphoma, tumor lysis syndrome was observed after the first Rituximab infusion in those patients with lymphocyte counts >10×10$^9$L, (39).

Radioimmunotherapy with $^{90}$Yttrium-Labeled Anti-CD20 Antibody in Combination with Rituximab Another therapeutic approach to NHL under evaluation is a radiolabeled anti-CD20 antibody (IDEC-Y2B8) in combination with Rituximab. IDEC-Y2B8 ($^{90}$Y-ibritumomab tiuxetan) is a murine IgG$_1$ kappa anti-CD20 antibody conjugated to $^{90}$Y via a chelator, MX-DTPA, which is covalently bound to the antibody. Rituximab (250 mg/m$^2$) is administered prior to IDEC-Y2B8 to deplete peripheral B lymphocytes and improve biodistribution of the radiolabeled antibody.

In a recently reported Phase I/II study (40-42), patients with low-grade NHL (N=34), intermediate-grade NHL (N=14), or mantle-cell lymphoma (N=3) were treated with IDEC-Y2B8. The median age was 60, 71% were male, and 96% were Caucasian. Of 51 patients with relapsed or refractory NHL, 34 (67%) responded to single doses of 0.2, 0.3, or 0.4 mCi/kg of IDEC-Y2B8. The ORR was 82% (28/34) for patients with low-grade or follicular NHL and was 43% (6/14) for patients with intermediate-grade lymphoma. No patients with mantle-cell disease responded.

A Phase III randomized study comparing IDEC-Y2B8 with Rituximab (375 mg/m$^2$ weekly times 4) for treatment of low-grade follicular or transformed NHL patients is ongoing. Another Phase III trial is also being conducted in patients with relapsed NHL who are refractory to Rituximab.

Summary

In the absence of curative therapy for NHL, the objective of treatment is to achieve control of the disease for a meaningful duration and provide relief of tumor-related symptoms without undue toxicity. Treatment with Rituximab is a brief, 22-day outpatient therapy with limited adverse events in most patients. In clinical studies, 50% of evaluable relapsed or chemotherapy refractory low-grade or follicular NHL patients achieved complete or partial responses. These responses were durable without maintenance therapy; the median TTP for responders was 13.2 months and the median DR was 11.6 months in the pivotal study.

Rituximab is approved as a safe and effective treatment for patients with relapsed low-grade or follicular B-cell NHL. It has significant clinical activity, a novel mechanism of action, and compares favorably with alternative therapies in response rate and response duration. Completion of ongoing studies will verify the role of alternative Rituximab regimens and Rituximab in the treatment of other CD20+ B-lymphocyte malignancies.

REFERENCES

1. Press O, Appelbaum F, Ledbetter J, Martin P, Zarling J, Kidd P, Thomas E. Monoclonal antibody 1F5 (anti-CD20) serotherapy of human B-cell lymphomas. *Blood* 1987; 69:584-591.
2. Dillman R. Antibodies as cytotoxic therapy. *J. Clin. Oncol.* 1994; 12:1497-1515.
3. Grossbard M, Press O, Appelbaum F, Bernstein I, Nadler L. Monoclonal antibody-based therapies of leukemia and lymphoma. *Blood* 1992; 80:863-878.
4. Reff M, Carner K, Chambers K, Chinn P, Leonard J, Raab R, Newman R, Hanna N, Anderson D. Depletion of B cells in vivo by a chimeric mouse human monoclonal antibody to CD20. *Blood* 1994; 83:435-445.
5. Demidem A, Lam T, Alas S, Hariharan K, Hanna N, Bonavida B. Chimeric anti-CD20 (IDEC-C2B8) monoclonal antibody sensitizes a B cell lymphoma cell line to cell killing by cytotoxic drugs. *Cancer Biotherapy & Radiopharmaceuticals* 1997; 12:177-186.
6. Maloney D, Liles T, Czerwinski D, Waldichuk C, Rosenberg J, Grillo-López A, Levy R. Phase I clinical trial using escalating single-dose infusion of chimeric anti-CD20 monoclonal antibody (IDEC-C2B8) in patients with recurrent B-cell lymphoma. *Blood* 1994; 84:2457-2466.
7. Maloney D, Grillo-López A, White C, Bodkin D, Schilder R, Neidhart J, Janakiraman N, Foon K, Liles T-M, Dallaire B, Wey K, Royston I, Davis T, Levy R. IDEC-C2B8 (Rituximab) anti-CD20 monoclonal antibody therapy in patients with relapsed low-grade non-Hodgkin's lymphoma. *Blood* 1997; 90: 2188-2195.
8. McLaughlin P, Grillo-López A, Link B, Levy R, Czuczman M, Williams M, Heyman M, Bence-Bruckler I, White C, Cabanillas F, Jain V, Ho A, Lister J, Wey K, Shen D, Dallaire B. Rituximab chimeric anti-CD20 monoclonal antibody therapy for relapsed indolent lymphoma: half of patients respond to a 4-dose treatment program. *J. Clin Oncol.* 1998; 16:2825-2833.
9. McLaughlin P, Grillo-López A, Maloney D, Link B, Levy R, Czuczman M, Cabanillas F, Dallaire B, White C. Efficacy controls in long-term follow-up of patients treated with rituximab for relapsed or refractory, low-grade or follicular NHL. *Blood* 1998; 92:414a-415a.
10. Janakiraman N, McLaughlin P, White C, Maloney D, Shen D, Grillo-López A. Rituximab: Correlation between effector cells and clinical activity in NHL. *Blood* 1998; 92 (10 Suppl 1):337a.
11. Berinstein N, Grillo-López A, White C, Bence-Bruckler I, Maloney D, Czuczman M, Green D, Rosenberg J, McLaughlin P, Shen D. Association of serum Rituximab (IDEC-C2B8) concentration and anti-tumor response in the treatment of recurrent low-grade or follicular non-Hodgkin's lymphoma. *Annals of Oncology* 1998; 9:995-1001.
12. Tobinai K, Kobayashi Y, Narabayashi M, Ogura M, Kagami Y, Morishima Y, Ohtsu T, Igarashi T, Sasaki Y, Kinoshita T, Murate T. Feasibility and pharmacokinetic study of a chimeric anti-CD20 monoclonal antibody (IDEC-C2B8, rituximab) in relapsed B-cell lymphoma. *Annals of Oncology* 1998; 9:527-534.
13. Piro L, White C, Grillo-López A, Janakiraman N, Saven A, Beck T, Varns C, Shuey S, Czuczman M, Lynch J, Kolitz J, Jain V. Extended RITUXAN® (anti-CD20 monoclonal antibody) therapy for relapsed or refractory low-grade or follicular non-Hodgkin's lymphoma. 1999; Submitted
14. Davis T, White C, Grillo-López A, Velasquez W, Link B, Maloney D, Dillman R, Williams M, Mohrbacher A, Weaver R, Dowden S, Levy R. Rituximab: First report of a Phase II (PII) trial in NHL patients (pts) with bulky disease. *Blood* 1998; 92 (10 Suppl 1):414a.
15. Byrd J, White C, Thomas S, Veldsquez W, Rosenberg J, Grillo-López A. Rituximab therapy in previously treated Waldenstrom's Macroglobulinemia: Preliminary evidence of activity. *Blood* 1998; 92 (TO Suppl 1): 106(a).
16. O'Brien S, Freireich E, Andreeff M, Lerner S, Keating M. Phase I/III Study of Rituxan in chronic lymphocytic leukemia (CLL). *Blood* 1998; 92:105a, #431.
17. Venugopal P, Sivararnan S, Huang X, Chopra H, O'Brien T, Jajeh A, Preisler H. Upregulation of CD20 expression in chronic lymphocytic leukemia (CLL) cells by in vitro exposure to cytokines. *Blood* 1998; 10:247a.
18. Flinn I, O'Donnell P, Noga S, Vogelsang G, Greyer M, Goodrich A, Abrams R, Marcellus D, Miller C, Jones R., Ambinder R. In vivo purging and adjuvant immunotherapy with Rituximab PBSC transplant for NHL. *Blood* 1998; 92:648a, #2673.
19. Davis T, Levy R, White C, Czuczman M, McLaughlin P, Link B, Varns C, Weaver R, Grillo-López A. Rituximab: Phase II (PII) retreatment (ReRx) study in patients (pts) with low-grade or follicular (LG/F) NHL. *Blood* 1998; 92 (10 Suppl 1):414a.
20. Davis T, Czerwinski D, Levy R. Therapy of B cell lymphoma with anti-CD20 antibodies can result in the loss of CD20 antigen expression. *Clinical Cancer Research* 1999; 5: In press.
21. Czuczman M, Grillo-López A, White C, Saleh M, Gordon L, LoBuglio F, Jonas C, Klippenstein D, Dallaire B, Varns C. Treatment of patients with low-grade B-cell lymphoma with the combination of chimeric anti-CD20 monoclonal antibody and CHOP chemotherapy. *Journal of Clinical Oncology* 1999; 17:268-276.
22. White C, Czuczman M, Grillo-López A, White C, Saleh M, Gordon L, LoBuglio A, Jonas C, Alkuzweny B, Dowen S. Rituximab/CHOP chemoimmunotherapy in patients (pts) with low grade lymphoma (LG/F NHL): Progression free survival (PFS) after three years (median) follow-up. *Proceedings of ASCO* 1999, In press.
23. Wadler S, Schwartz E. Principles in the biomodulation of cytotoxic drugs by interferons. *Seminars in Oncology* 1992; 19:45-48.
24. Nakamura K, Kubo A, Hosokawa S, Nagaike K, Hashimoto S. Effect of alpha-interferon on anti-alpha-fetoprotein-monoclonal-antibody targeting of hepatoma. *Oncology* 1993; 50:35-40.
25. Greiner J, Guadagni F, Noguchi P, Pestka S, Colcher D, Fisher P, Schlom J. Recombinant interferon enhances monoclonal antibody-targeting of carcinoma lesions in vivo. *Science* 1987; 235:895-898.
26. Murray J, Zukiwski A, Mujoo K, Rosenblum M. Recombinant alpha-interferon enhances tumor targeting of an antimelanoma monoclonal antibody in vivo. *Journal of Biological Response Modifiers* 1990; 9:556-563.
27. Yokota S, Hara H, Luo Y, Seon B. Synergistic potentiation of in vivo antitumor activity of anti-human T-leukemia immunotoxins by recombinant alpha-interferon and daunorubicin. *Cancer Research* 1990; 50:32-37.
28. Grillo-López A, Dallaire B, Shen C, Varns C, McClure A, Caralli V. Treatment options for patients with relapsed low-grade or follicular lymphoma: The role of IDEC-C2B8. *Antibody Immunoconjugates & Radiopharmaceuticals* 1995; 8:60.
29. Davis T, Maloney D, White C, Grillo-López A, Williams M, Weiner G, Sklenar T, Levy R. Combination immunotherapy of low grade or follicular (LG/F) non-Hodgkin's lymphoma (NHL) with Rituximab and alpha interferon: Interim analysis. *Proceedings of the American Society of Clinical Oncology* 1998; 17:11a.
30. Smalley R, Andersen J, Hawkins M, Bhide V, O'Connell M, Oken M, Borden E. Interferon alfa combined with cytotoxic chemotherapy for patients with non-Hodgkin's lymphoma. *New England Journal of Medicine* 1992; 327: 1336-1341.
31. Hagenbeek A, Carde P, Meerwaldt J H, Somers R, Thomas J, De Bock R, Raemaekers J M, van Hoof A, De Wolf-Peeters C, van Glabbeke M. Maintenance of remission with human recombinant interferon alfa-2a in patients with stages In and IV low-grade malignant non-Hodgkin's lymphoma. European Organization for Research and Treatment of Cancer Lymphoma Cooperative Group. *Journal of Clinical Oncology* 1998; 16:41-47.
32. Solal-Céligny P, Lepage E, Brousse N, Tendler C, Brice P, Haioun C, Gabarre J, Pignon B, Tertian G, Bouabdallah R, Rossi J-F, Doyen C, Coiffier B. Doxorubicin-containing regimen with or without interferon alfa-2b for advanced follicular lymphomas: Final analysis of survival and toxicity in the groupe d'etude des lymphomes folliculaires 86 trial. *Journal of Clinical Oncology* 1998; 16:2332-2338.
33. van der Kolk L, Grillo-López A, Gerritsen W, Jonkhoff A, Baars J, van Oers M. Chimeric anti-CD20 monoclonal antibody (rituximab) plus G-CSF in relapsed B-cell lymphoma: A phase I/II clinical trial. *Blood* 1998; 92:241b, #4037.
34. Coiffier B, Haioun C, Ketterer N, Engert A, Tilly H, Ma D, Johnson P, Lister A, Feuring-Buske M, Radford J A, Capdeville R, Diehl V, Reyes F. Rituximab (anti-CD20 monoclonal antibody) for the treatment of patients with relapsing or refractory aggressive lymphoma: a multicenter phase H study. *Blood* 1998; 92:1927-1932.
35. Link B, Grossbard M, Fisher R, Czuczman M, Gilman P, Lowe A, Vose J. Phase II pilot study of the safety and efficacy of rituximab in combination with CHOP chemotherapy in patients with previously untreated- or high-grade NHL. *Proceedings of the American Society of Clinical Oncology* 1998; 17:3a.
36. Tsai, D, Moore H, Porter D, Vaughn D, Luger S, Loh R, Schuster S, Stadtmauer E. Progressive intermediate grade non-Hodgkin's lymphoma after high dose therapy and autologous peripheral stem cell transplantation (PSCT) has a high response rate to Rituximab. *Blood* 1998; 92:415a, #1713.
37. Byrd J, Waselenko J, Maneatis T, Murphy T, Weickrum R, Ward F, White C. Rituximab therapy in hematologic malignancy patients with circulating blood tumor cells: Association with increased infusion-related side effects and rapid tumor lysis. *Blood* 1998; 92 (10 Suppl 1): 106a.
38. Jensen M, Winkler U, Manzke O, Diehl V, Engert A. Rapid tumor lysis in a patient with B-cell chronic lymphocytic leukemia and lymphocytosis treated with an anti-CD20 monoclonal antibody (IDEC-C2B8, rituximab). *Annals of Hematology* 1998; 77:89-91.
39. Winkler U, Jensen M, Manzke O, Tesch H, Bohlen H, Diehl V, Engert A. Severe side effects in patients with B-cell chronic lymphocytic leukemia (CLL) and lymphocytosis treated with the monoclonal antibody Rituximab. *Blood* 1998; 92:285b, #4228.
40. Witzig T, White C, Wiseman G, Gordon L, Emmanouilides C, Raubitschek A, Janakiraman N, Gutheil J, Spies S, Silverman D, Parker E, Grillo-López A. Phase I/II trial of IDEC-Y2B8 radioimmunotherapy for treatment of relapsed or refractory CD20 positive B-cell non-Hodgkin's lymphoma. *Journal of Clinical Oncology* 1999; Submitted.
41. Wiseman G, White C, Witzig T, Gordon L, Emmanouilides C, Raubitschek A, Janakiraman N, Spies S, Silverman D, Gutheil J, Schilder R, Parker E, Rosenberg J, Grillo-López A. IDEC-Y2B8 radioimmunotherapy: Baseline bone marrow involvement and platelet count are better predictors of hematologic toxicity than dosimetry. *Blood* 1998; 92:417a.
42. Witzig T, White C, Wiseman G, Gordon L, Emmanouilides C, Raubitschek A, Janakiraman N, Spies S, Silverman D, Gutheil J, Schilder R, Ding E, Shen D, Grillo-López A. IDEC-Y2B8 Radioimmunotherapy: Responses in patients with splenomegaly. *Blood* 1998; 92:417(a).

43. Witherspoon R P, Lum L G, Storb R. Immunologic reconstitution after bone marrow grafting. *Semin Hematol* 21:2, 1984.
44. Anderson, K C et al. Hematological engraftment and immune reconstitution posttransplant with anti-B1 purged autologous bone marrow. *Blood* 69:597, 1987.
45. Lum LG. Kinetics of immune reconstitution after human marrow transplantation. *Blood* 69:369, 1987.
46. Azogui O., Gluckman E., Fradelizi, D., Inhibition of IL-2 production after human allogeneic bone marrow transplantation. *J. Immunol.* 131:1205, 1983
47. Welte, K. et al, Defective Interleukin-2 production in patients after bone marrow transplantation and in vitro restoration of defective T lymphocyte proliferation by highly purified Interleukin. *Blood* 64:380, 1984.
48. Cayeau, S. et al., T-cell ontogeny after bone marrow transplantation: failure to synthesize Interleukin-2 (IL-2) and lack of CD2- and CD3-mediated proliferation by both CDE4+ and CD8+ cells even in the presence of exogenous IL-2. *Blood* 74:2270, 1989.
49. Bosley, A. et al., Interleukin-2 as consolidative immunotherapy against minimal residual disease. *Nouv Rev Fr Hematol* 32:13, 1990.
50. Caligiuri, M. A. et al, Extended continuous infusion low-dose recombinant Interleukin-2 in advanced cancer. Prolonged immunomodulation without significant toxicity. *J Clin Oncol* 9:2110, 1991.
51. Caligiuri, M. A. et al, Selective immune modulation of NK cells following prolonged infusions of low dose recombinant IL-2. *J Clin Invest* 91:123, 1993.
52. Caligiuri, M. A., Low-dose recombinant Interleukin-2 therapy: rationale and potential clinical applications. *Sem in Oncol* 20:3, 1993.
53. Klarnet, J. P. et al, Antigen-driven T cell clones can proliferate in vivo, eradicate disseminated leukemia and provide specific immunologic memory. *J. Immunol.* 138:4012, 1987.
54. Soiffer, R. J. et al, Clinical and immunologic effects of prolonged infusion of low-dose recombinant Interleukin-2 after autologous and T cell-depleted allogeneic bone marrow transplantation. *Blood* 79:517, 1992.
55. Soiffer, R. J. et al, Effect of low-dose Interleukin-2 on disease relapse after T-cell depleted allogeneic bone marrow transplantation. *Blood* 84:964, 1994.
56. Lauria, F. et al, Immunologic and clinical modifications following low-dose subcutaneous administration of rIL-2 in non-Hodgkin's lymphoma patients after autologous bone marrow transplantation. *BMT* 18:79, 1996.
57. Vey, N. et al, A pilot study of autologous bone marrow transplantation followed by recombinant Interleukin-2 in malignant lymphomas. *Leukemia & Lymphoma* 21:107, 1996.
58. Venugopal, P. et al, Upregulation of CD20 expression in CLL cells by cytokines. Submitted to ASH Meeting, December 1998.

What is claimed is:

1. A method for treating low grade or follicular non-Hodgkin's lymphoma (NHL) comprising administering to a patient 375 mg/m² of rituximab during a cyclophosphamide, doxorubicin, vincristine, and prednisone (CHOP) chemotherapeutic regimen, wherein the CHOP chemotherapy and rituximab are administered to the patient on Day 1 of each CHOP chemotherapy cycle.

2. The method of claim 1 wherein the method provides a beneficial synergistic effect in the patient.

3. The method of claim 1 wherein 375 mg/m² of rituximab is administered to the patient once every 3 weeks.

4. A method for treating low grade or follicular non-Hodgkin's lymphoma (NHL) comprising administering to a patient 375 mg/m² of an anti-CD20 antibody during a cyclophosphamide, doxorubicin, vincristine, and prednisone (CHOP) chemotherapeutic regimen, wherein the CHOP chemotherapy and the antibody are administered to the patient on Day 1 of each CHOP chemotherapy cycle, and wherein the antibody comprises a light chain variable region comprising the amino acid sequence in SEQ ID NO: 1 and a heavy chain variable region comprising the amino acid sequence in SEQ ID NO: 2, and comprises human gamma 1 heavy-chain and kappa light-chain constant region amino acid sequences.

5. The method of claim 4 wherein the method provides a beneficial synergistic effect in the patient.

6. The method of claim 4 wherein 375 mg/m² of the antibody is administered to the patient once every 3 weeks.

7. A method for treating low grade or follicular non-Hodgkin's lymphoma (NHL) comprising administering to a patient 375 mg/m² of rituximab once every three weeks during cyclophosphamide, doxorubicin, vincristine, and prednisone (CHOP) chemotherapy, wherein the CHOP chemotherapy and rituximab are administered to the patient on Day 1 of each CHOP chemotherapy cycle.

8. The method of claim 7 wherein the method provides a beneficial synergistic effect in the patient.

* * * * *